US007268209B2

(12) United States Patent
Ishima et al.

(10) Patent No.: US 7,268,209 B2
(45) Date of Patent: Sep. 11, 2007

(54) PEPTIDES, DERIVATES THEREOF, PROCESS FOR PRODUCING THE SAME, NOVEL STRAIN PRODUCING THE SAME, AND ANTIVIRAL AGENT COMPRISING THE SAME AS ACTIVE INGREDIENT

(75) Inventors: Masahiro Ishima, Funabashi (JP); Tsutomu Yoshida, Sagamihara (JP); Takayuki Yamazaki, Noda (JP); Fumio Sugawara, Niiza (JP); Kiyoshige Hatta, Ebetsu (JP); Manabu Shimojoe, Saitama (JP); Kazuyoshi Masaki, Sakado (JP)

(73) Assignee: Toyo Suisan Kaisha, Ltd., Tokyo (JP)

( * ) Notice: Subject to any disclaimer, the term of this patent is extended or adjusted under 35 U.S.C. 154(b) by 565 days.

(21) Appl. No.: 10/632,949

(22) Filed: Jul. 31, 2003

(65) Prior Publication Data

US 2004/0102605 A1 May 27, 2004

Related U.S. Application Data

(63) Continuation of application No. PCT/JP02/01039, filed on Feb. 7, 2002.

(30) Foreign Application Priority Data

Feb. 8, 2001 (JP) .............................. 2001-032729

(51) Int. Cl.
*C07K 5/00* (2006.01)
(52) U.S. Cl. ..................................... 530/300; 424/260.1
(58) Field of Classification Search .................... None
See application file for complete search history.

(56) References Cited

U.S. PATENT DOCUMENTS 5,258,493 A * 11/1993 Adams et al. .............. 530/317

FOREIGN PATENT DOCUMENTS

| JP | 1-95792 | 4/1989 |
| WO | WO92/05191 A1 | 4/1992 |
| WO | WO99/20792 A1 | 4/1999 |
| WO | WO 00/63240 A1 | 10/2000 |

OTHER PUBLICATIONS

Nielsen et al. Viscosinamide, a cyclic depsipeptide with surfactant and anitfungal properties produces by *Pseudomonas fluorescence* DR54. 1999, Journal of Applied Microbiology. vol. 87, p. 80-90. Cited in the IDS.*

Minoru Hiramoto et al., "The Revised Structure of Viscosin, A Peptide Antibiotic", *Tetrahedron Letters*, No. 13, pp. 1087-1090 (1970).

"Kaiyo Biseibutu no Seibutsukassei Busshitsu" (Biologically Active Substances of Ocean Microorganisms), supervised by The Japanese Society of Fisheries Science and published by Koseisha Koseikaku Co., Ltd. on Apr. 15, 1990.

Christopher Prowse, "Kill and Cure, The Hope and Reality of Virus Inactivation", *Vox Sanguinis*, 67 Suppl. 3, 191-196 (1994).

Neilsen, T.H. et al., "Structure, production characteristics and fungal antagonism of tensin—a new antifungal cyclic lipopeptide from *Pseudomonas fluorescens* strain 96.578," *Journal of Applied Microbiology*, Dec. 2000, vol. 89, No. 6, pp. 992-1001.

Mereyala H. B. et al., "Transformation of D-glucose to 1-deoxy-1-[4'-methoxyphenyl]- 2R,3R,4R-pentitol template: synthesis of Karalicin analogues," *Tetrahedron Asymmetry*, Mar. 13, 1998, vol. 9, No. 5, pp. 827-833.

Nielsen T.H. et al., "Viscosinamide, a new cyclic depsipeptide with surfactant and antifungal properties produced by *Pseudomonas fluorescens* DR54," *Journal of Applied Mircobiology*, Jul. 1999, vol. 87, No. 1, pp. 80-90.

Kamei Y. et al., "Screening of Bacteria with Antiviral Activity from Freshwater Salmonid Hatcheries," *Microbiology and Immunology*, vol. 32, No. 1, pp. 67-74, Database Biosis Online! Biosciences Information Service, Philadelphia, PA, US, 1988, Database accession No. PREV198885080354.

* cited by examiner

*Primary Examiner*—Bruce R. Campell
*Assistant Examiner*—Agnieszka Boesen
(74) *Attorney, Agent, or Firm*—Frishauf, Holtz, Goodman & Chick, P.C.

(57) ABSTRACT

Peptides having, as constitutive amino acids, (1) 4 glutamine residues, 1 glutamic acid residue, 1 serine residue, 2 valine residues, 1 isoleucine residue and 5 leucine residues, and having a 3-hydroxydecanoyl group bonded, via an amide linkage, to the N-terminal leucine residue thereof; (2) 4 glutamine residues, 1 glutamic acid residue, 1 serine residue, 3 valine residues, and 5 leucine residues, and having a 3-hydroxydecanoyl group bonded, via an amide linkage, to the N-terminal leucine residue thereof; or (3) 4 glutamine residues, 1 glutamic acid residue, 1 serine residue, 2 valine residues, 1 isoleucine residue and 5 leucine residues, and having a 3-hydroxydodec-5-enoyl group bonded, via an amide linkage, to the N-terminal leucine residue thereof. The peptides have an antiviral activity. A strain capable of producing the above peptides and belonging to a new species of genus *Pseudomonas*.

21 Claims, 42 Drawing Sheets

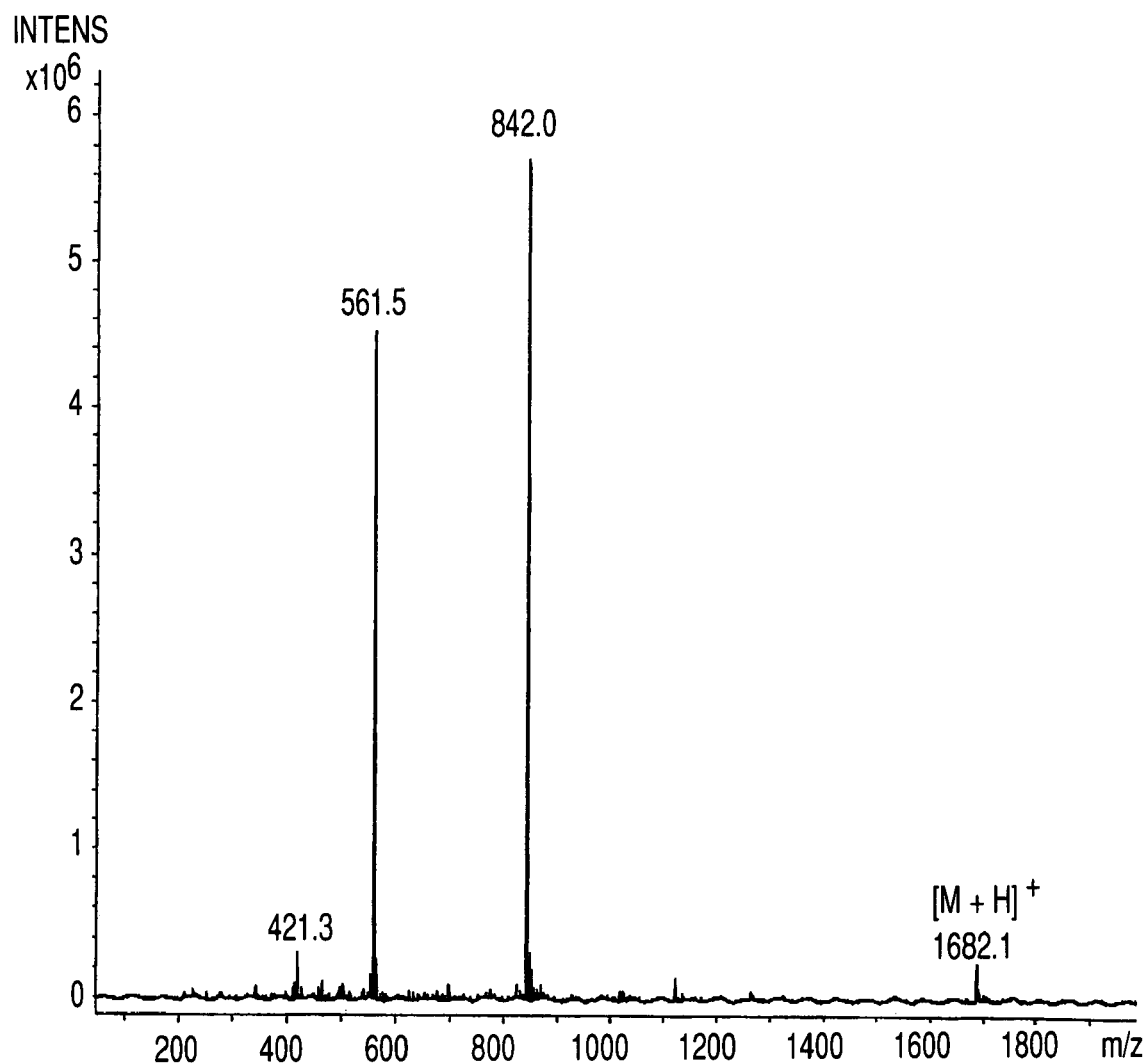
F I G. 15

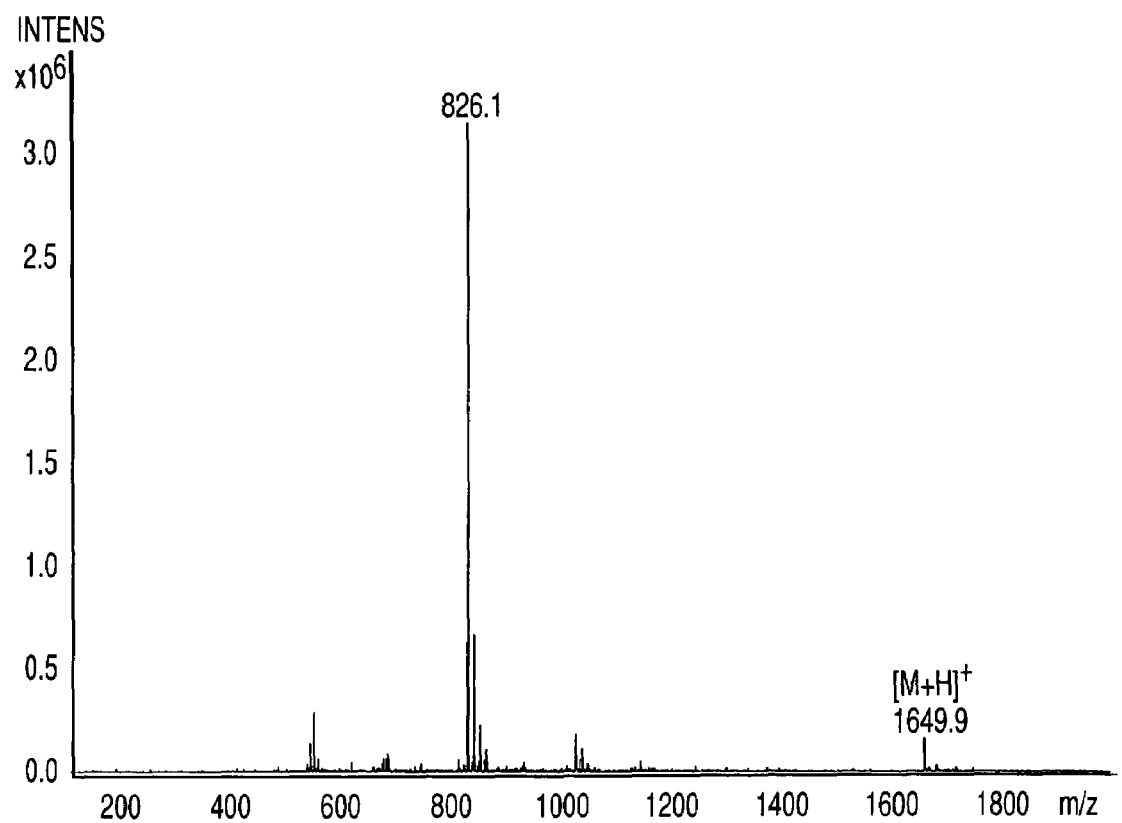
F I G. 22

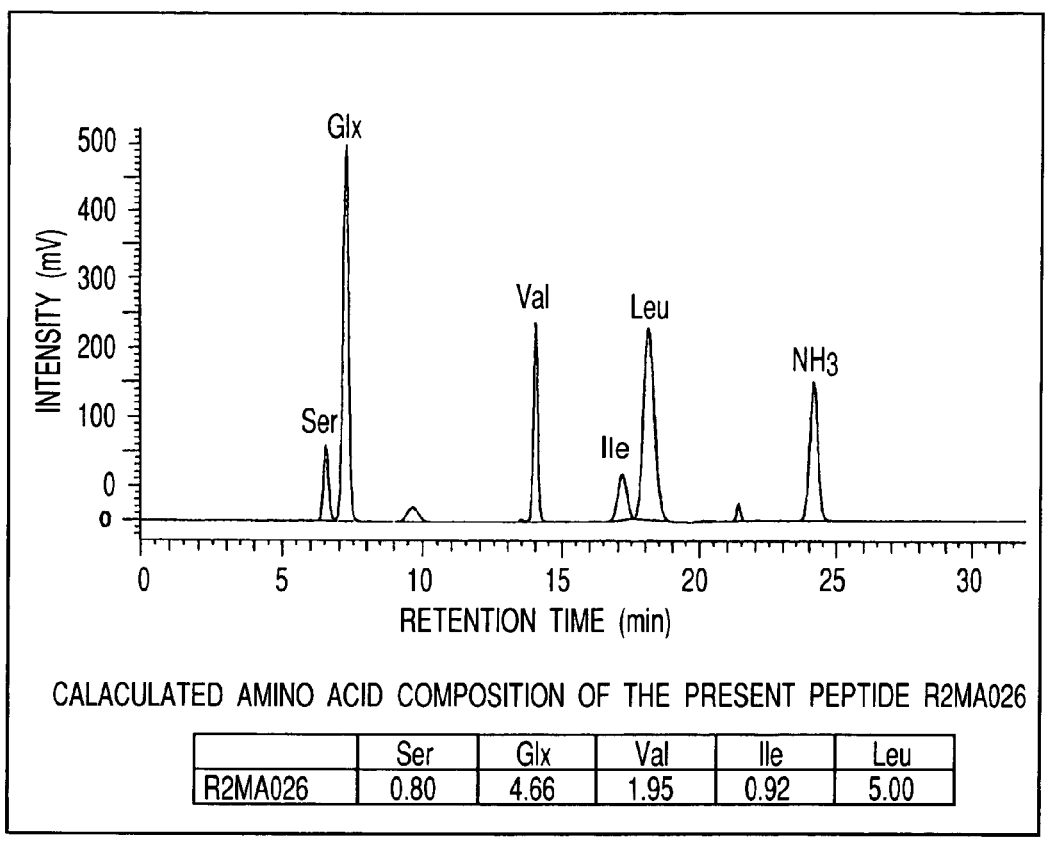
F I G. 24

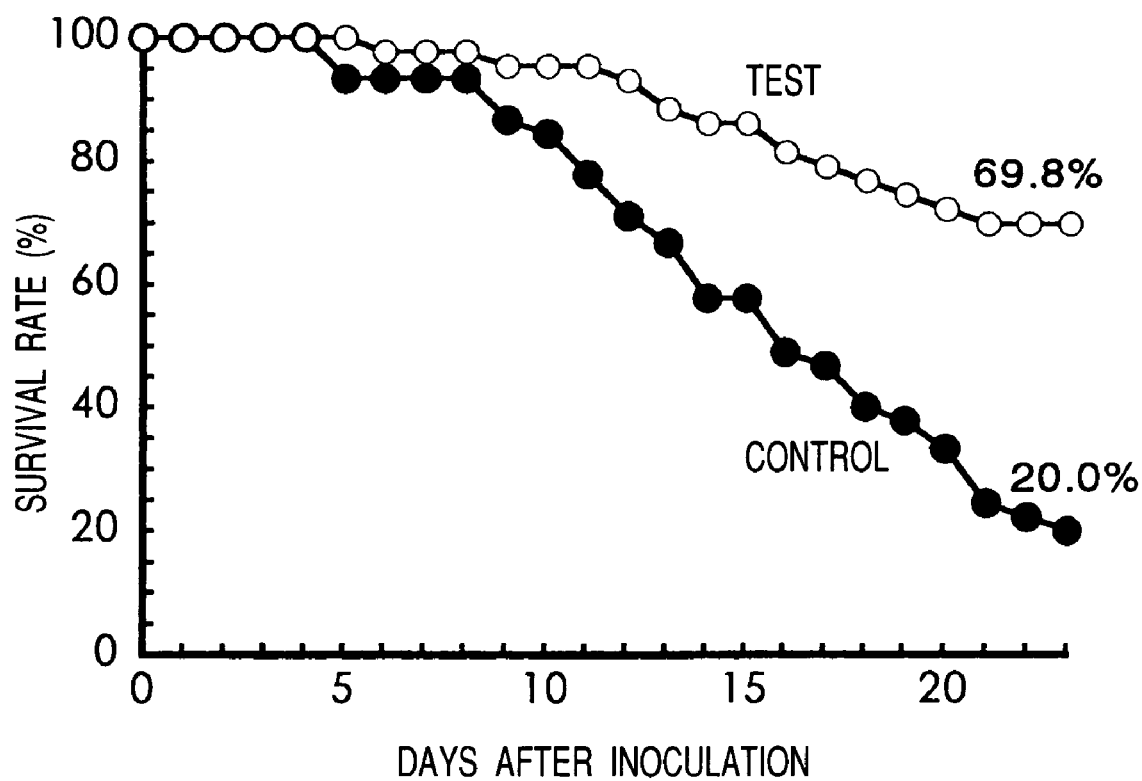
F I G. 34

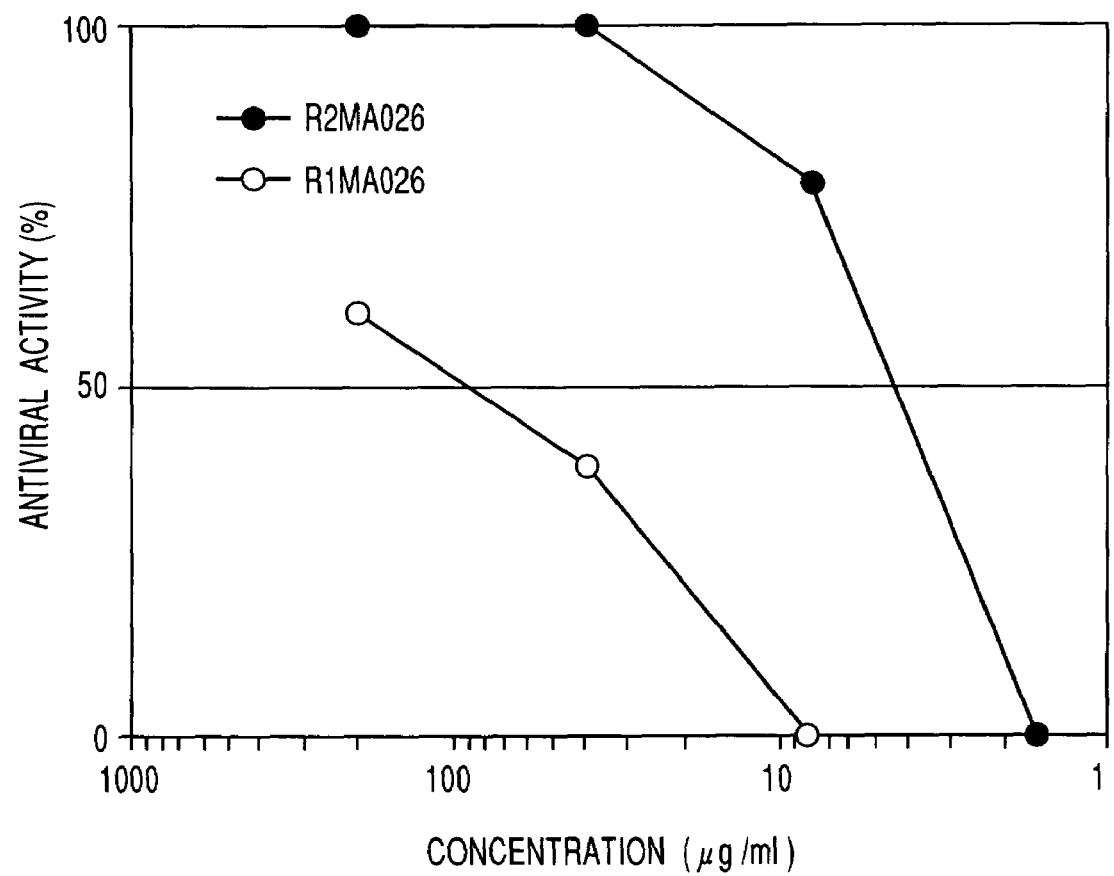
F I G. 36

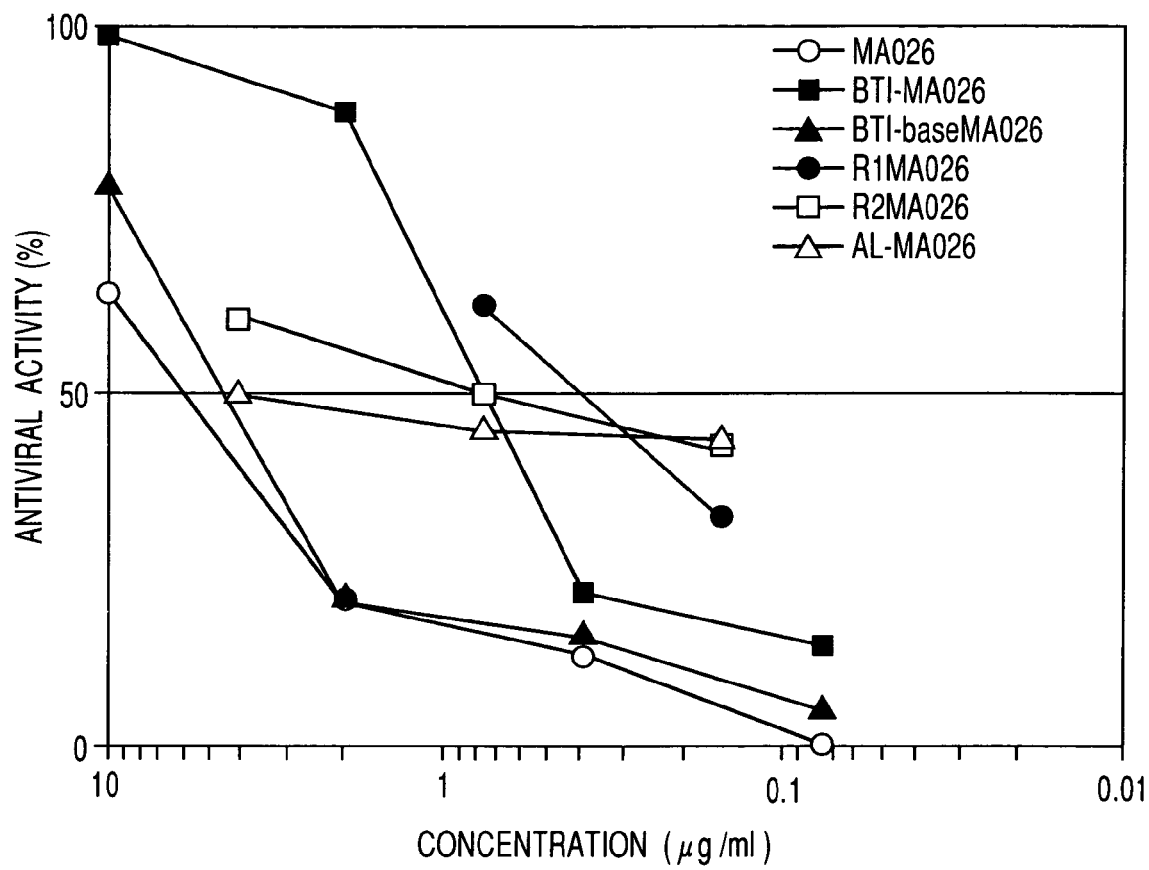
F I G. 38

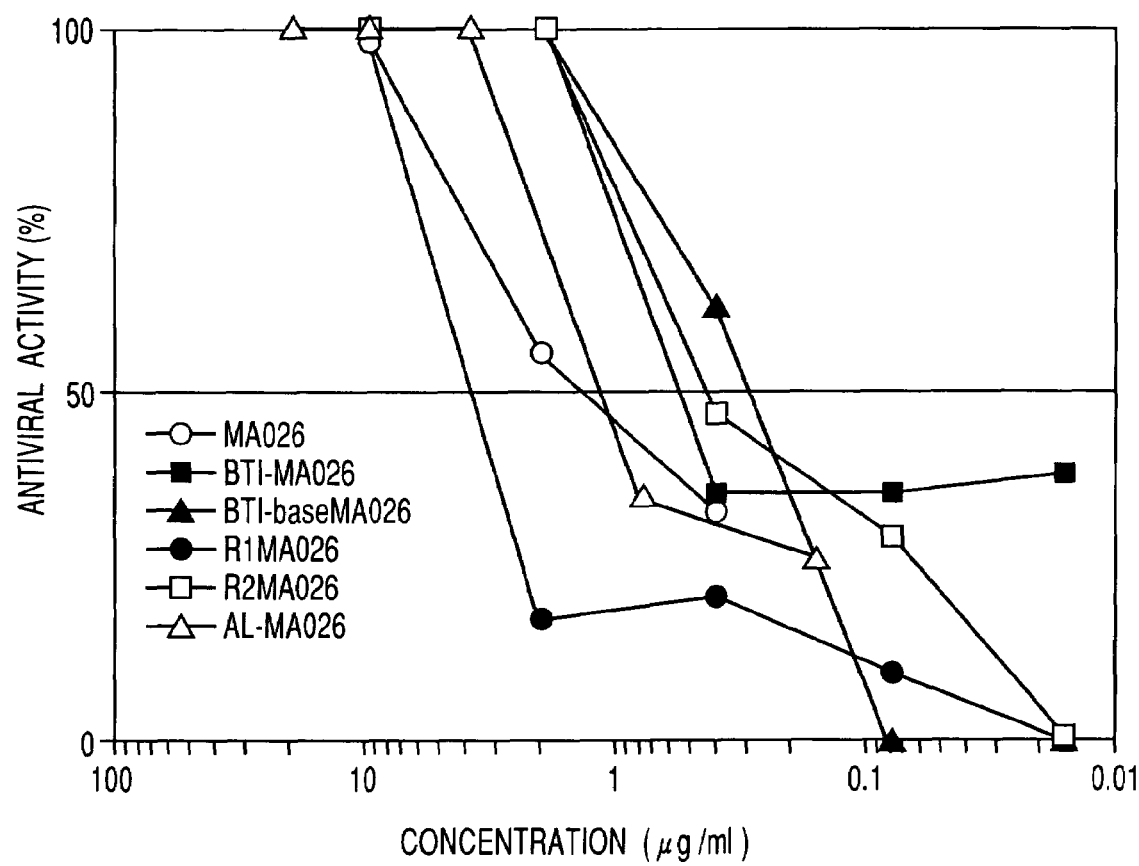
F I G. 40

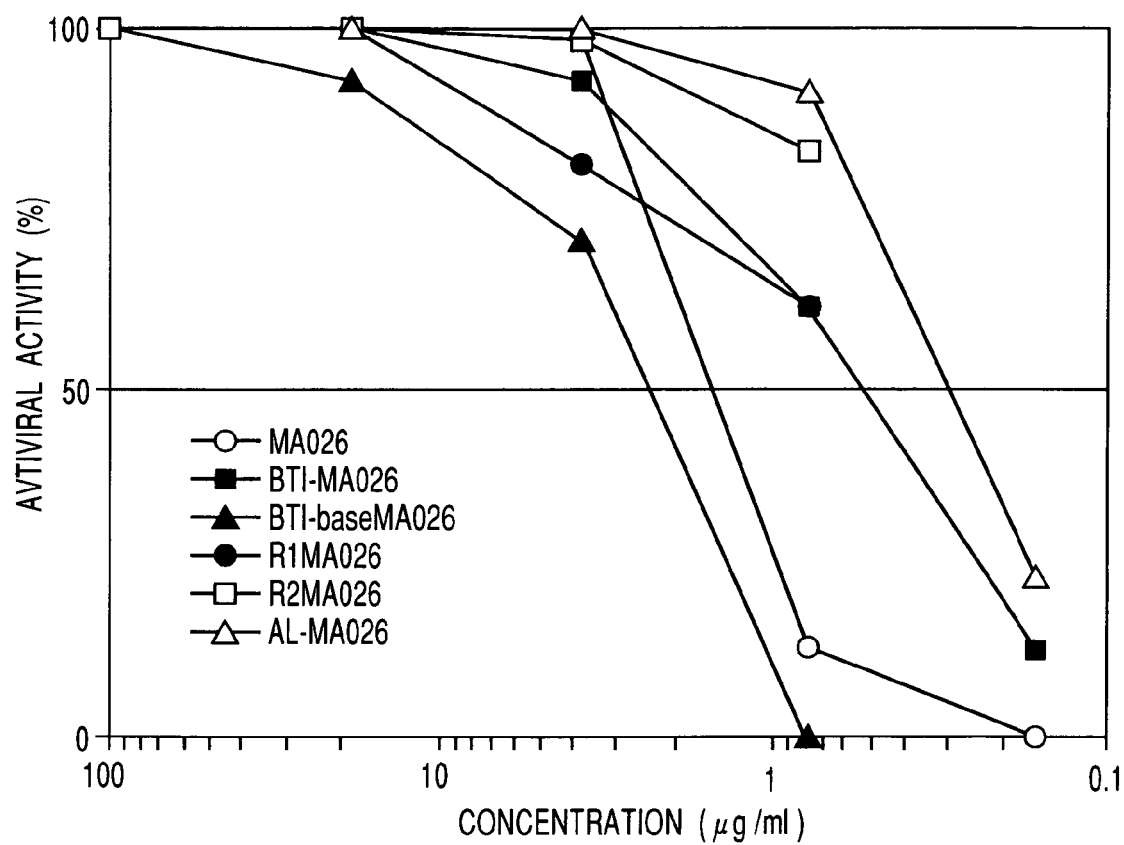
F I G. 41

PEPTIDES, DERIVATES THEREOF, PROCESS FOR PRODUCING THE SAME, NOVEL STRAIN PRODUCING THE SAME, AND ANTIVIRAL AGENT COMPRISING THE SAME AS ACTIVE INGREDIENT

CROSS-REFERENCE TO RELATED APPLICATIONS

This is a Continuation Application of PCT Application No. PCT/JP02/01039, filed Feb. 7, 2002, which was not published under PCT Article 21(2) in English.

This application is based upon and claims the benefit of priority from the prior Japanese Patent Application No. 2001-032729, filed Feb. 8, 2001, the entire contents of which are incorporated herein by reference.

BACKGROUND OF THE INVENTION

1. Field of the Invention

The present invention relates to novel peptides, derivatives thereof. The present invention also relates to salts of the novel peptides and derivatives thereof.

Also, the present invention relates to a strain belonging to a novel species capable of producing the novel peptides.

Further, the present invention relates to a process for producing the novel peptides.

In addition, the present invention relates to an antiviral agent comprising, as an active ingredient, at least one member selected from the group consisting of (a) the novel peptides, derivatives thereof and pharmaceutically acceptable salts thereof and (b) the strain belonging to a novel species.

2. Description of the Related Art

Microorganisms, e.g., viruses and bacteria, are known to be causing agents of various infectious disease. Research and development of antibiotics, etc., against bacterial-causing infectious disease are advancing, and many pharmaceuticals preparations are in actual use. On the other hand, pharmaceutical preparations against infectious disease caused by viruses are not as advanced as the antibacterial agents, under the present circumstances, although causative viruses themselves have been identified with the development in virology in recent years.

For example, against viral infections occurring in farms of fishery product such as fish and shellfish, only vaccines are in actually used against Iridovirus of red sea bream and infectious hematopoietic necrosis virus of salmonid fish and etc. In this field, antiviral agents are still at the stage of research and development, and have not yet been put to practical use.

As literature on antiviral agents in the fishery field, mention can be made of, e.g., Jpn. Pat. Appln. KOKAI Publication No. 1-95792. This publication describes that a substance (46NW-04A) produced by *Pseudomonas* sp. 46NW-04A (FERM P-9579) has an antiviral activity against viruses such as the salmonid herpes virus (OMV) and the infectious hematopoietic necrosis virus (IHNV).

The above-described substance is also described in Fisheries Science Series 79, "Kaiyo Biseibutu no Seibutsukassei Busshitsu" (Biologically Active Substances of Ocean Microorganisms), supervised by The Japanese Society of Fisheries Science and published by Koseisha Koseikaku Co., Ltd. on Apr. 15, 1990. According to its description, the substance (46NW-04A) having an antiviral activity described in the above publication is referred to as white powder-with the molecular formula $C_{54}H_{95}N_9O_{16}$, having, as constitutive amino acids, 1 threonine residue, 2 serine residues, 1 valine residue, 1 glutamic acid residue, 1 isoleucine residue and 3 leucine residues, and having a 3-hydroxydecanoyl group that is bonded to the N-terminal leucine thereof. It is described therein that the above substance (46NW-04A) has a structure very similar to that of the viscosin reported by Hiramoto et al. (Tetrahedron Letters, vol. 13, pp. 1087-1090, 1970). It is also reported that the microorganism of the genus *Pseudomonas* producing this substance (46NW-04A) was identified as *Pseudomonas fluorescens* biovar I.

In addition to the above report, several kinds of analogues to the above-mentioned viscosin have been reported for various objects and uses.

Although a large number of reports on development directed to prevention or treatment against viral diseases of fish have been made, besides the above report, the commercially available pharmaceutical preparations for marine products directed to prevention or treatment of the viral diseases are limited to the vaccines for Iridovirus of red sea bream, salmonid INHV and etc., as described above, and the antiviral agents are not yet put to practical use.

BRIEF SUMMARY OF THE INVENTION

This invention has been made in view of the circumstances described above, and an object of this invention is to provide a novel antiviral agent.

As a result of intensive study, the present inventors found three groups of substances each of which, in enterobacteria derived from fish, can serve as an active ingredient in an antiviral agent, to complete the present invention.

Specifically, the novel substances belonging to a first group found by the present inventors are peptides having, as constitutive amino acids, 4 glutamine-derived amino acid residues, 1 glutamic acid residue, 1 serine residue, 2 valine residues, 1 isoleucine residue and 5 leucine residues, and having a 3-hydroxydecanoyl group that is bonded, via an amide linkage, to the N-terminal leucine residue thereof. The present invention provides these novel substances and salts thereof, as well as an antiviral agent comprising, as an active ingredient, at least one member selected from the group consisting of these novel substances and pharmaceutically acceptable salts thereof.

More specifically, the active ingredients belonging to the peptides of the first group in the antiviral agent found by the present inventors includes the following peptide:

a depsipeptide having a cyclic structure therein and having, as constitutive amino acids, 4 glutamine residues, 1 glutamic acid residue, 1 serine residue, 2 valine residues, 1 isoleucine residue and 5 leucine residues, and having a 3-hydroxydecanoyl group that is bonded, via an amide linkage, to the N-terminal leucine residue thereof, and the depsipeptide having the following formula (I) (referred to hereinafter as "the present peptide MA026"):

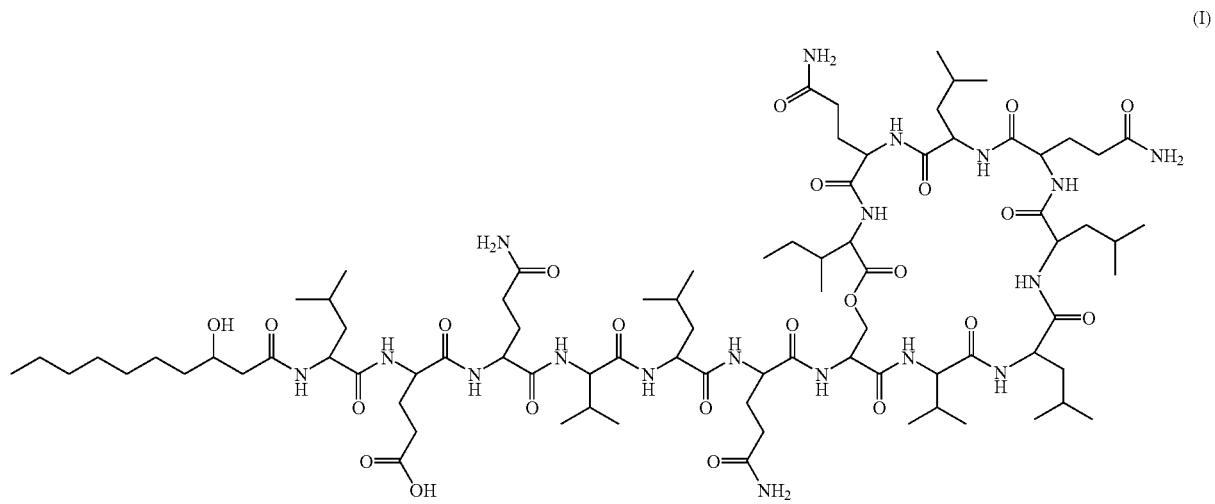

(I)

Further, the present inventors found that 3 peptide derivatives of the present peptide MA026 can also be used as the active ingredient in the antiviral agent. These 3 peptide derivatives are also novel substances. The present invention provides these novel derivatives and salts thereof, as well as an antiviral agent comprising, as an active ingredient, at least one member selected from the group consisting of these derivatives and pharmaceutically acceptable salts thereof.

Of the 3 derivatives as the active ingredient in the antiviral agent described above, the first derivatives are lower-alkylated derivatives (referred to hereinafter as "the present peptides AL-MA026") of the depsipeptide having a cyclic structure therein and having, as constitutive amino acids, 4 glutamine residues, 1 glutamic acid residue, 1 serine residue, 2 valine residues, 1 isoleucine residue and 5 leucine residues, and having a 3-hydroxydecanoyl group that is bonded, via an amide linkage, to the N-terminal leucine residue thereof.

The second derivative is a depsipeptide derivative having a cyclic structure therein and having, as constitutive amino acids, 4 α,γ-diaminobutyric acid residues, 1 glutamic acid residue, 1 serine residue, 2 valine residues, 1 isoleucine residue and 5 leucine residues, and having a 3-hydroxydecanoyl group that is bonded, via an amide linkage, to the N-terminal leucine residue thereof, the depsipeptide derivative having the following formula (II) (referred to hereinafter as "the present peptide BTI-MA026"):

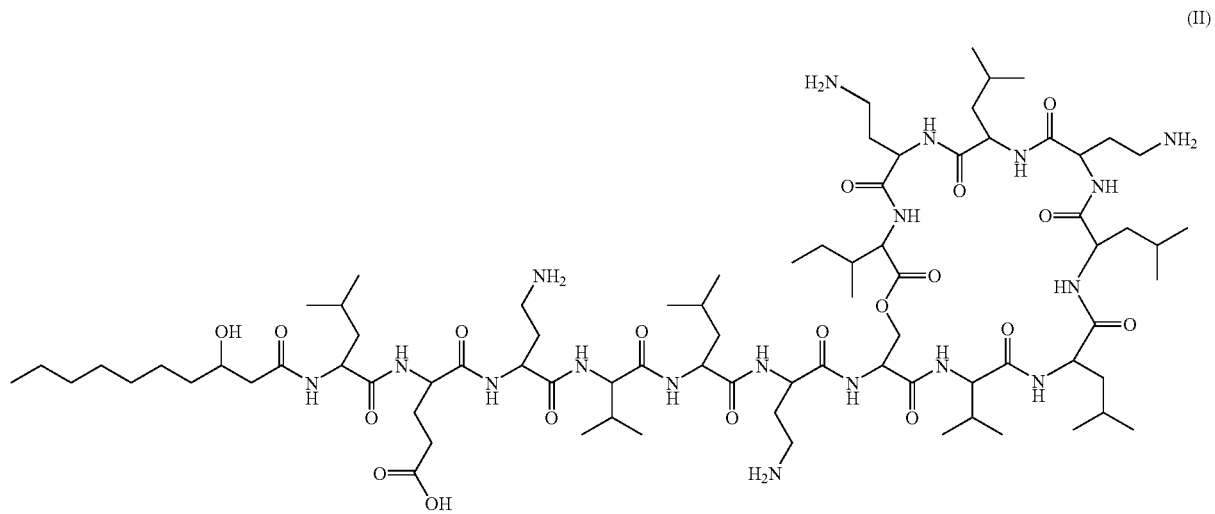

(II)

The third derivative is a linear peptide, having, as constitutive amino acids, 4 α,γ-diaminobutyric acid residues, 1 glutamic acid residue, 1 serine residue, 2 valine residues, 1 isoleucine residue and 5 leucine residues, and having a 3-hydroxydecanoyl group that is bonded, via an amide linkage, to the N-terminal leucine residue thereof, the peptide derivative having the following formula (III) (referred to hereinafter as "the present peptide BTI-base MA026"):

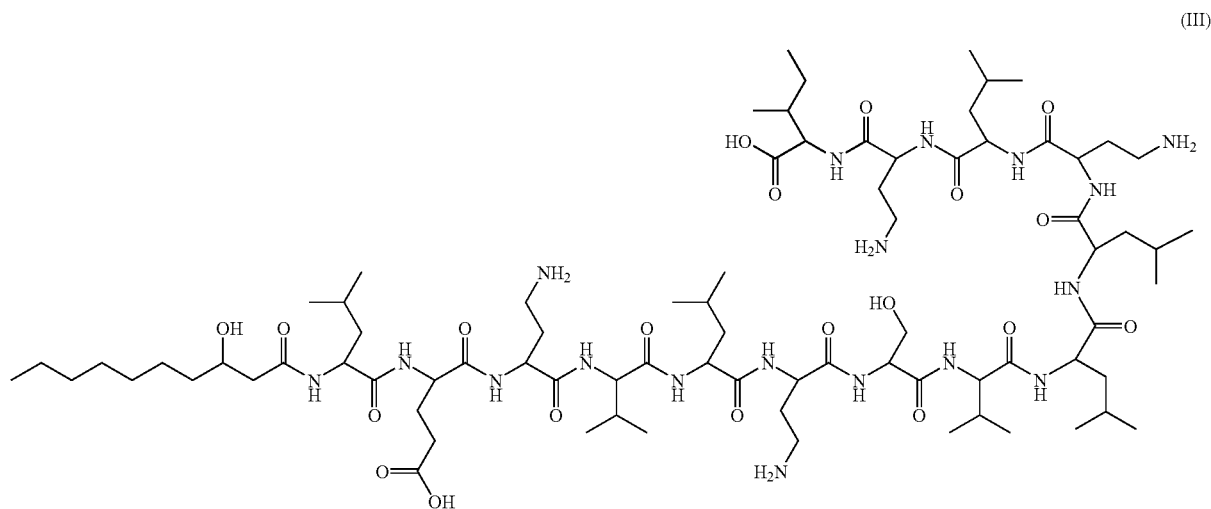

(III)

In addition to the present peptides belonging to the first group including MA026, and derivatives thereof described above, the present inventors found peptides of second and third groups which are usable as the active ingredient in the antiviral agent. The second and third peptides are also novel substances. The present invention also provides the second and third peptides as well as salts thereof. Further, the present invention also provides an antiviral agent comprising, as an active ingredient, at least one member selected from the group consisting of the second and third peptides and pharmaceutically acceptable salts thereof.

The peptides belonging the second group provided by the present invention are those having, as constitutive amino acids, 4 glutamine-derived amino acid residues, 1 glutamic acid residues, 1 serine residue, 3 valine residues, and 5 leucine residues, and having a 3-hydroxydecanoly group that is bonded, via an amide linkage, to the N-terminal leucine residue thereof. The peptides belonging to the second group includes a peptide having a cyclic structure therein and having, as constitutive amino acids, 4 glutamine residues, 1 glutamic acid residue, 1 serine residue, 3 valine residues, and 5 leucine residues, and having a 3-hydroxydecanoyl group that is bonded, via an amide linkage, to the N-terminal leucine residue thereof, and the peptide having the following formula (IV) (also referred to hereinafter as "the present peptide R1MA026"):

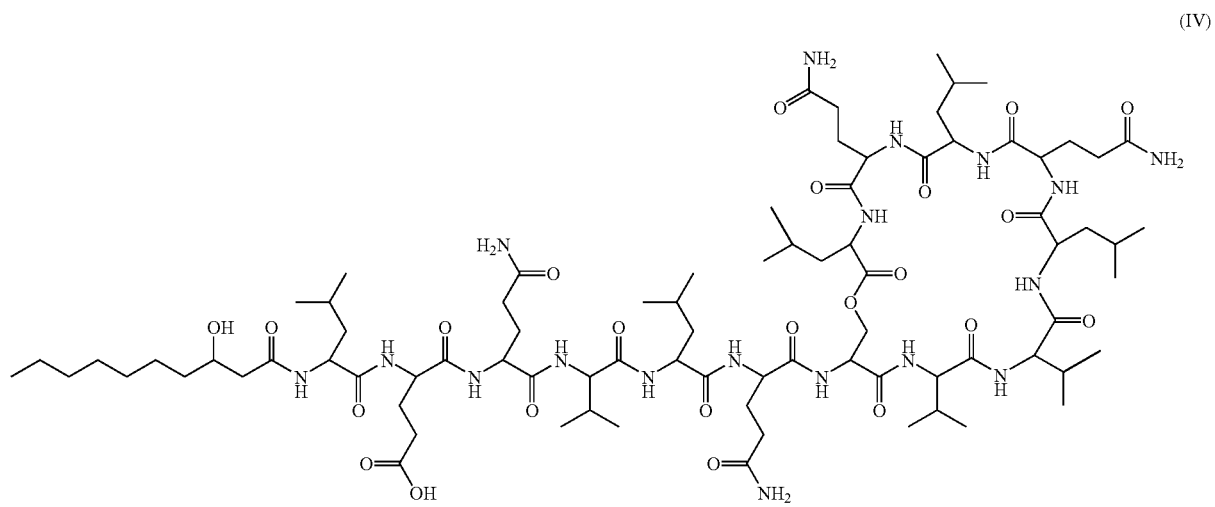

(IV)

The peptides belonging to the third group are those having, as constitutive amino acids, 4 glutamine-derived amino acid residues, 1 glutamic acid residue, 1 serine residue, 2 valine residues, 1 isoleucine residue and 5 leucine residues, and having a 3-hydroxydodec-5-enoyl group that is bonded, via an amide linkage, to the N-terminal leucine residue thereof. The peptides belonging to the third group includes a peptide having a cyclic structure therein and having, as constitutive amino acids, 4 glutamine residues, 1 glutamic acid residue, 1 serine residue, 2 valine residues, 1 isoleucine residue and 5 leucine residues, and having a 3-hydroxydodec-5-enoyl group that is bonded, via an amide linkage, to the N-terminal leucine residue thereof, and the peptide having the following formula (V) (also referred to hereinafter as "the present peptide R2MA026"):

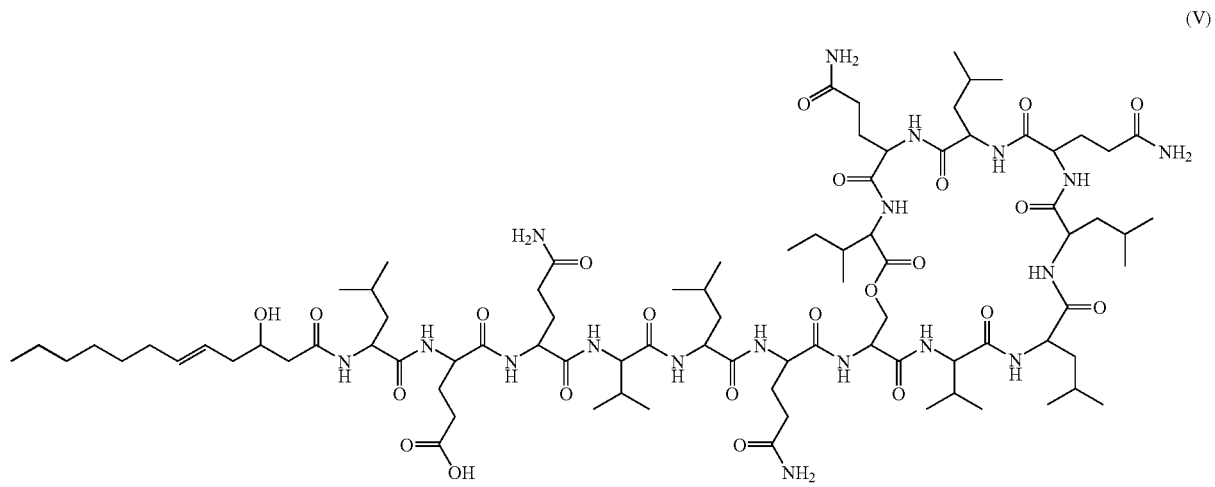

(V)

The present peptides MA026, R1MA026 and R2MA026 described above can be purified from a culture of a new strain of the genus Pseudomonas. The present invention also provides this strain of the genus Pseudomonas (also referred to hereinafter as "the present RtIB026 strain") and a process for producing at least one of the present peptides MA026, R1MA026 and R2MA026 from a culture of this strain.

The present RtIB026 strain is a strain deposited on Jan. 29, 2001 under FERM BP-7436 with the National Institute of Bioscience and Human-Technology, the name of which, from April, 2001, is changed to the National Institute of Advanced Industrial Science and Technology (AIST), International Patent Organism Depository (IPOD) (located at 1-3, Higashi 1-chome, Tsukuba-shi, Ibaraki-ken, 305-8566 Japan).

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 15 is an ESI-MS spectrogram.
FIG. 22 is an ESI-MS spectrogram chart.
FIG. 24 is an amino acid analysis chart.

FIG. 34 is a graph showing the result of an administration test of the present RtIB026 strain.

FIG. 36 is a graph showing the antiviral activity against IHNV.

FIG. 38 is a graph showing the antiviral activity against swine influenza virus.

FIG. 40 is a graph showing the antiviral activity against swine herpes virus.

FIG. 41 is a graph showing the antiviral activity against swine-derived Japanese encephalitis virus.

DETAILED DESCRIPTION OF THE INVENTION

Figure 1:
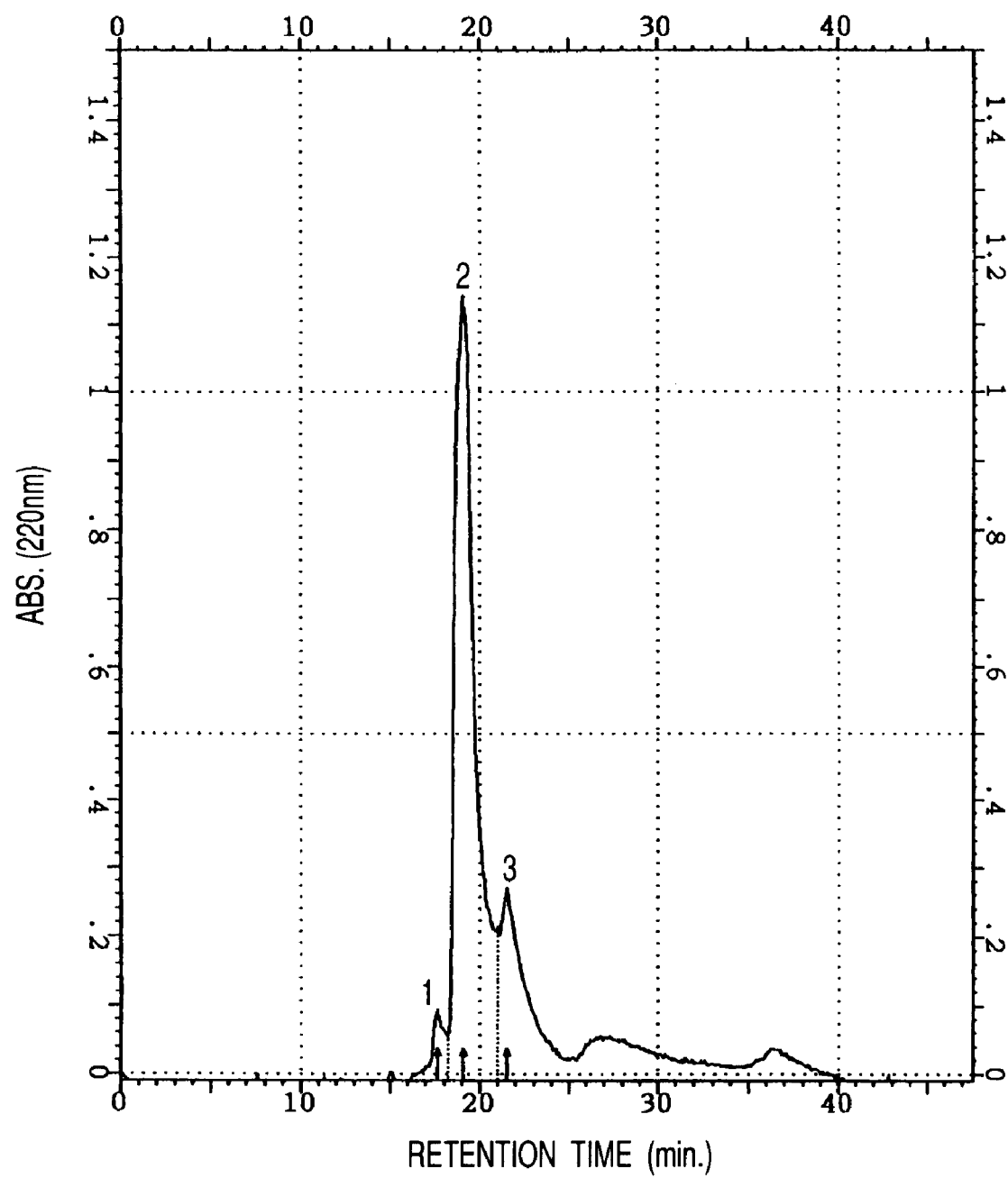
FIG. 1 is a high performance liquid chromatogram.

Hereinafter, the 3 peptides (MA026, R1MA026 and R2MA026) usable as the active ingredient in the antiviral agent of the present invention and obtainable from a culture of the new strain (RtIB026 strain) according to this invention, as well as the new strain (RtIB026 strain), are described in detail.

<Peptide MA026>

The present peptide MA026 has a structure of the above formula (I), wherein, as constitutive amino acids, 4 glutamine residues, 1 glutamic acid residue, 1 serine residue, 2 valine residues, 1 isoleucine residue and 5 leucine residues, are contained. As is apparent from the formula (I), the N-terminal amino acid residue of the present peptide MA026 is leucine, and a 3-hydroxydecanoyl group is bonded, via an amide linkage, to the amino group of this leucine. Further, the present peptide MA026 has a cyclic structure therein. This cyclic structure is formed by an ester linkage between the hydroxy group of serine and the carboxy group of isoleucine among the amino acid residues constituting the peptide.

Salts of the present peptide MA026 include, but are not limited to, alkaline metal salts (e.g., sodium salts, potassium salts), alkaline earth metal salts (e.g., calcium salts, magnesium salts), hydrochlorides, acetates and trifluoroacetates.

The present peptide MA026 can be recovered from a culture of a strain of the genus *Pseudomonas* separated from digestive tracts in fish. Specifically, the peptide can be separated and purified by filtration, concentration, desalting and separation with silica gel column and high performance liquid chromatographies from a culture of the strain (the present RtIB026 strain) of the novel species of genus *Pseudomonas* found by the present inventors. One example of the method in which the strain producing the present peptide MA026 is separated from digestive tracts in fish is shown in Example 1 below.

The present RtIB026 strain is a strain deposited on Jan. 29, 2001 under FERM BP-7436 with the National Institute of Advanced Industrial Science and Technology (AIST), formerly known as the National Institute of Bioscience and Human-Technology.

<RtIB026 Strain>

The RtIB026 strain of the present invention is described in detail.

The results of examination of the bacteriological characteristics of the RtIB026 strain are shown below.

1) Examination of Physiological and Biochemical Characteristics

The results of examination of the physiological and biochemical characteristics of the present RtIB026 strain are shown in Tables 1-1 and 1-2. The examination was conducted by a method in accordance with a report of Stanier et al. (J. Gen. Microbiol., 43, 159-271, 1966), etc.

TABLE 1-1

| Characteristics | |
|---|---|
| Gram stain | − |
| Motility | + |
| Flagellar number | >1 |
| Fluorescent pigment production | + |
| Oxidase | + |
| Gelatin liquefaction | + |
| Lipase (Tween 80 hydrolysis) | − |
| Starch hydrolysis | − |
| DNase | − |
| Lecithinase (egg yolk) | + |
| Extracellular PHB hydrolysis | − |
| Levan formation from sucrose | − |
| PHB accumulation | − |
| Growth at 4° C. | + |
| Growth at 37° C. | + |
| Growth at 39° C. | + |
| Growth at 41° C. | − |
| O − F test | O |
| Denitrification | − |
| G + C content of DNA | 64.7% |

TABLE 1-2

| Assimilation of carbon compounds | |
|---|---|
| Lactate | + |
| Citrate | + |
| Glycerol | + |
| L-glutamate | + |
| L-arginine | + |
| D-mannitol | + |
| Glucose | + |
| Glycine | − |
| Ethanol | − |
| Mannitol | + |
| L-alanine | + |
| β-alanine | + |
| L-leucine | + |
| L-isoleucine | + |
| L-valine | + |
| L-histidine | + |
| L-phenylalanine | + |
| D-xylose | − |
| Galactose | − |
| Sucrose | − |
| Erythritol | − |
| Sorbitol | − |
| L-tryptophan | − |
| Sarcosine | + |

TABLE 1-2-continued

| Assimilation of carbon compounds | |
| --- | --- |
| m-inositol | − |
| Propylene glycol | − |
| L-arabinose | − |
| Butyramine | + |
| Histamine | + |
| Trehalose | − |

As shown in Tables 1-1 and 1-2 above, this strain is considered as belonging to the genus Pseudomonas because of its characteristics of being Gram-negative, rod-shaped, motile with flagella, and oxidative in the O-F test.

Among the bacterial species described in Bergey's Manual of Systematic Bacteriology (Vol. 1, 1984), the strain most similar in characteristics to the present strain was *P. fluorescens* biovar V. However, the present strain is different from *P. fluorescens* biovar V because both the strains are different in the G+C content of DNA by 4% or more.

2) Comparison of 16S rDNA Sequence

The 16S rDNA sequence in the present RtIB026 strain was determined, and on the basis of the resulting sequence, the phylogenetic analysis was performed in an usual manner. As a result, the present strain has 98% or more similarity with the type strains *Pseudomonas fulva, P. putida* (biovar A), *P. plecoglossicida* and *P. oryzihabitans,* thus revealing that the present strain is a strain belonging to the same cluster in the phylogenetic tree.

3) DNA-DNA Hybridization

The four strains (*Pseudomonas fulva, P. putida* (biovar A), *P. plecoglossicida* and *P. oryzihabitans*) having 98% or more similarity with the present RtIB026 strain in the comparison of 16S rDNA sequence described above were examined in a DNA-DNA hybridization. As a result, all the four tested strains had 70% or less homology with the present strain.

Table 2 shows their homology (%). The results of 16Sr DNA described above are also shown in Table 2.

TABLE 2

DNA—DNA homology and similarity of 16S rDNA between the closely related type strains and the RtIB02G strain (%)

| Objective strains | 16S rDNA | DNA—DNA homology |
| --- | --- | --- |
| *Pseudomonas putida* bv.A (IAM1236) | 98.3 | 33 |
| *Pseudomonas fulva* (IAM1529) | 98.3 | 54 |
| *Pseudomonas plecoglossicida* (FPC951) | 99 | 44 |
| *Pseudomonas oryzihabitans* (JCM2952) | 98.5 | 34 |

The International Microbial Classification Committee specifies that microbial strains having 70% or more homology in said DNA-DNA hybridization are regarded as the same species (Int. J. Syst. Bacteriol., Vol. 37, No. 4, 463-464 (1987)).

From the results in 1) to 3) above and because of production of the present novel substance, i.e., the peptide MA026, etc., the present inventors determined that the present RtIB026 strain is a strain belonging to a novel species.

The strains belonging to a novel species of the invention include the present RtIB026 strain, as well as its offspring, and mutants thereof and strains recognized, regarding bacteriological characteristics, to be the same species as the present RtIB026 strain, which are strains capable of producing at least one of the present peptides MA026, R1MA026 and R2MA026.

The present invention also includes strains capable of producing at least one of the present peptides MA026, R1MA026 and R2MA026, as long as they belong to genus Pseudomonas.

Methods for producing the present peptides MA026, R1MA026 and R2MA026, as well as R1MA026 and R2MA026, are described below.

<A Method for Producing the Peptides MA026, R1MA026 and R2MA026>

The present peptides MA026, R1MA026 and R2MA026 can be purified by subjecting a culture of the present RtIB026 strain to column chromatography etc.

Specifically, the present peptides can be purified by subjecting a culture of the present RtIB026 strain to silica gel chromatography and high performance liquid chromatography. One example of the method of purifying the present peptides MA026, R1MA026 and R2MA026 from a culture of the present RtIB026 strain is shown in Example 2 below.

FIG. 1 is one example of a chromatogram in high performance liquid chromatography conducted according to the method described in Example 2. Out of the 3 peaks shown in FIG. 1, a fraction eluted at a retention time of 17.7 minutes (peak No. 1) contains the present peptide R1MA026. A fraction eluted at a retention time of 19.0 minutes (peak No. 2) contains the present peptide MA026. A fraction eluted at a retention time of 21.4 minutes (peak No. 3) contains the present peptide R2MA026.

<Peptide R1MA026>

It was confirmed that the present peptide R1MA026 is a peptide having, as constitutive amino acid residues, 4 glutamine residues, 1 glutamic acid residue, 1 serine residue, 3 valine residues and 5 leucine residues, and having the chemical structure of formula (IV) set forth above. As is apparent from the formula (IV), the N-terminal amino acid residue of the present peptide R1MA026 is leucine residue. A 3-hydroxydecanoyl group is bonded to this leucine residue via an amide linkage. The present R1MA026 has a cyclic structure in its chemical structure. The cyclic structure is formed with an ester linkage between the hydroxy group of the serine residue and the carboxy group of the C-terminal leucine residue among the amino acid residues constituting the peptide.

Salts of the present peptide R1MA026 include, but are not limited to, those described for the present peptide MA026 described above.

<Peptide R2MA026>

It was confirmed that the present peptide R2MA026 is a peptide having, as constitutive amino acids, 4 glutamine residues, 1 glutamic acid residue, 1 serine residue, 2 valine residues, 1 isoleucine residue and 5 leucine residues, and having the chemical structure of formula (V) set forth above. As is apparent from the formula (V), the N-terminal amino acid residue of the present peptide R2MA026 is leucine residue. A 3-hydroxydodec-5-enoyl group is bonded to this leucine residue via an amide linkage. The present R2MA026 has a cyclic structure in its chemical structure. The cyclic structure is formed with an ester linkage between the hydroxy group of the serine residue and the carboxy group of the C-terminal isoleucine residue among the amino acid residues constituting the peptide.

Salts of the present peptide R2MA026 include, but are not limited to, those described for the present peptide MA026 described above.

Hereinafter, the 3 peptides derivatives AL-MA026, BTI-MA026 and BTI-base MA026 derived from the present peptide MA026 are described in detail.

<Peptides AL-MA026>

The first derivatives (the present peptides AL-MA026) include derivatives obtained by lower-alkylation of the present peptide MA026 described above. That is, the present peptides AL-MA026 include lower-alkylation derivatives of the depsipeptide having a cyclic structure and has, as constitutive amino acids, 4 glutamine residues, 1 glutamic acid residue, 1 serine residue, 2 valine residues, 1 isoleucine residue and 5 leucine residues. The cyclic structure of the peptides AL-MA026, as in the same manner in the Peptide MA026, is formed with an ester linkage between the hydroxy group of the serine residue and the carboxy group of the isoleucine residue among the amino acid residues constituting the peptide. The N-terminal residue of the present peptides AL-MA026 is leucine residue. A 3-hydroxydecanoyl group is bonded, via an amide linkage to the amino group of this N-terminal leucine residue. The position of the lower-alkylation of the peptides AL-MA026 is on at least one functional group of the above-mentioned constitutive amino acids.

The lower alkyl group includes a linear, branched or cyclic lower alkyl group. The number of carbon atoms in the lower alkyl group is not particularly limited insofar as the lower-alkylated derivative has an antiviral activity, but in consideration of easiness of the production, production costs etc., the number of carbon atoms may be about 1 to 4.

The lower-alkylated functional group in the present peptides AL-MA026 is not particularly limited insofar as the lower-alkylated derivatives have an antiviral activity. For example, a free amino or carboxy group of the amino acid residues constituting the peptide is included therein. The lower alkylation includes, but is not limited to, N-alkylation of the above amino group and esterification of the carboxy group.

One example of the lower-alkylated derivatives (the present peptides AL-MA026) include lower-alkylated derivatives derived from the present peptide MA026 by lower-alkylating a free carboxy group of a glutamic acid residue thereof, and said derivatives having the following formula (VI):

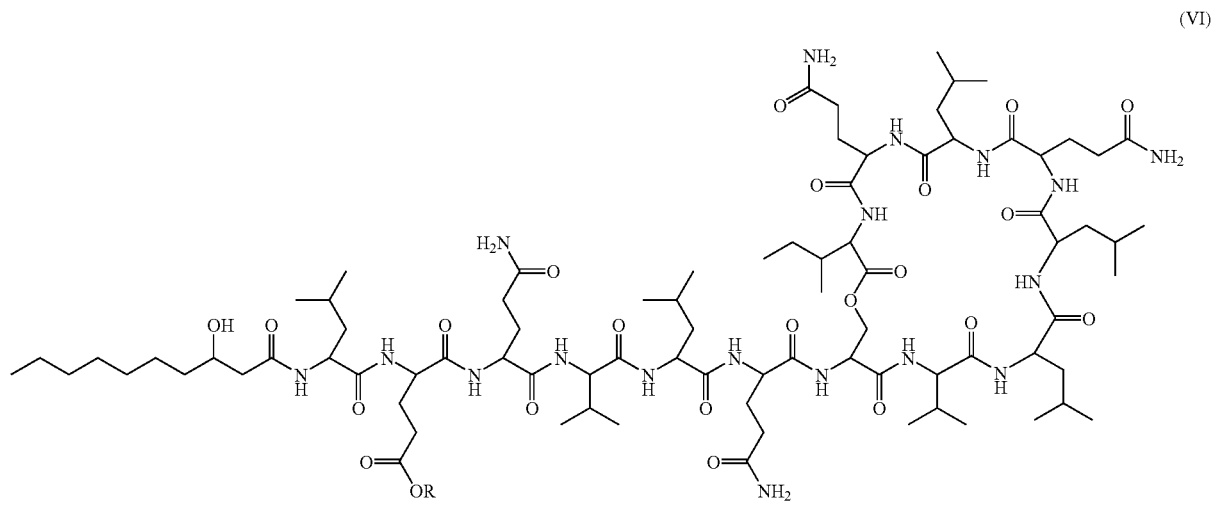

(VI)

wherein R represents a lower alkyl group.

The method of producing such lower-alkylated derivatives includes, but is not limited to, a method of using an alkylating agent to introduce an alkyl group into the present peptide MA026. The usable alkylating agent includes, but is not limited to, diazomethane, methyl iodide, trimethylsilyl-diazomethane, isobutylene, ethyl iodide, etc.

Salts of the present peptide AL-MA026 include, but are not limited to, those described for the present peptide MA026 described above.

<Peptide BTI-MA026>

The second derivative (the present peptide BTI-MA026) is the same as the present peptide MA026 except that each of the 4 lutamine residues in the present peptide MA026 have been replaced by α,γ-diaminobutyric acids. That is, the present peptide BTI-MA026 has, as constitutive amino acids, 4 α,γ-diaminobutyric acid residues, 1 glutamic acid residue, 1 serine residue, 2 valine residues, 1 isoleucine residue and 5 leucine residues, and having the formula (II) set forth above. As is apparent from the above formula (II), the N-terminal amino acid residue of the present peptide BTI-MA026 is leucine residue. A 3-hydroxydecanoyl group is bonded to this leucine residue via an amide linkage. The present BTI-MA026 has a cyclic structure in its chemical structure. The cyclic structure is formed with an ester linkage between the hydroxy group of the serine residue and the carboxy group of the isoleucine residue among the amino acid residues constituting the peptide.

The present peptide BTI-MA026 can be produced by Hofmann rearrangement in converting the primary carboxylic acid amide of glutamine in the present peptide MA026 into a primary amine. In the Hofmann rearrangement, [I,I-bis(trifluoroacetoxy)iodo] benzene (also referred to hereinafter as "BTI") can be suitably used.

Salts of the present peptide BTI-MA026 include, but are not limited to, those described for the present peptide MA026 described above.

<Peptide BTI-Base MA026>

The third derivative (the present peptide BTI-base MA026) is the same as BTI-MA026 except that the ester linkage between the serine residue and the isoleucine residue forming the cyclic structure of the present peptide BTI-MA026 described above has been hydrolyzed to form a linear peptide, and has the structural formula (III) above. As is apparent from the formula (III) above, the present peptide BTI-base MA026 has, as constitutive amino acids, 4 α,γ-diaminobutyric acid residues, 1 glutamic acid residue, 1 serine residue, 2 valine residues, 1 isoleucine residue and 5 leucine residues. The N-terminal of the present peptide BTI-baseMA026 is leucine residue. A 3-hydroxydecanoyl group is bonded, via an amide linkage, to this N-terminal leucine residue. The present peptide BTI-baseMA026 has no cyclic structure, and thus is a linear peptide derivative.

The hydrolysis reaction of the ester linkage between serine and isoleucine residues can be conducted by e.g. alkali hydrolysis. The usable base includes dimethyl amine, diethyl amine, sodium hydroxide, ammonia, sodium methoxide etc.

Salts of the present peptide BTI-base MA026 include, but are not limited to, those described for the present peptide MA026 described above.

<Antiviral Agent>

Now, the antiviral agent of this invention is described in more detail.

The strain of this invention belonging to novel species of genus Pseudomonas, the present RtIB026 strain, the present peptides (MA026, R1MA026 and R2MA026) and the present peptide MA026 derivatives (AL-MA026, BTI-MA026 and BTI-base MA026) as well as salts thereof can be used singly or in combination thereof as the active ingredient in the antiviral agent. When a salt of the present peptide or a salt of the present peptide derivative is used as the active ingredient in the antiviral agent, the salt includes but, insofar as it is a pharmaceutically acceptable salt, is not limited to those referred to as salts of the present peptide MA026.

In this specification, the antiviral agent encompasses those antiviral agents having the function of preventing infection of intended animals (including humans) with a virus or treating animals infected with a virus. The animals for which the antiviral agent of this invention is effective include, but are not limited to, mammals (including humans), birds, fish and crustaceans.

The viruses to which the antiviral agent of this invention can be applied include the following viruses.

Viruses having a lipid membrane. This lipid membrane includes a viral particle inner membrane besides a viral outer membrane called an envelope.

Such viruses include, but are not limited to, Rhabdovirus, Herpesvirus, Baculovirus, Iridovirus, Retrovirus, Orthomyxovirus, Flavivirus, Hepadnavirus and Filovirus.

Hosts for these viruses having the lipid membrane include, but are not limited to, mammals (for example, humans, cattle, dogs, cats, pigs), birds (for example, chickens), fish (for example, rainbow trout, salmons, eels, sea eels, red sea bream, yellowtail), crustaceans (for example, shrimp) etc.

The viruses having the lipid membrane whose hosts are mammals include, but are not limited to, human immunodeficiency virus (HIV), feline immunodeficiency virus (FIV), influenza virus, Japanese encephalitis virus, hepatitis C virus, dengue fever virus, hepatitis B virus, Ebola virus, herpes virus (for example, herpes simplex virus, herpes virus derived from domestic animals), Epstein Barr virus, etc. The viruses having the lipid membrane whose hosts are fish and crustaceans include, but are not limited to, infectious hematopoietic necrosis virus (IHNV) in salmonid, rhabdovirus (EVA) in American eels, rhabdovirus (EVEX) in European eels, yellow head disease virus (YHDV) in shrimp, herpes virus (OMV) in salmonid, herpes virus of eel (EHV), white spot syndrome virus (WSSV) in shrimp, peneas rod-shaped DNA virus (PRDV) in shrimp, red sea bream Iridovirus (RSIV).

Viruses having Single-Stranded RNA as a Genome

These viruses include, but are not limited to, rhabdovirus (for example, rabies virus, IHNV), retrovirus (for example, HIV, FIV), orthomyxovirus (for example, influenza virus), flavivirus (for example, hepatitis C virus, Japanese encephalitis virus, hepatitis C virus) and Filovirus (for example, Ebola virus), Picorna virus (for example, Taura syndrome virus). The hosts for these viruses having a single-stranded RNA as the genome include mammals, birds, fish, crustacean etc., and specific animals as hosts for these viruses and specific viruses whose hosts are these animals include, but are not limited to, those described above.

Viruses having Double-Stranded DNA as a Genome

These viruses include, but are not limited to, herpes virus, Baculovirus (for example, WSSV, PRDV), Iridovirus (for example, RSIV), and hepadona virus (for example, hepatitis B virus). Hosts for these viruses having a double-stranded DNA as the genome include mammals, birds, fish, crustaceans etc., and specific animals as hosts for these viruses and specific viruses whose hosts are these animals include, but are not limited to, those described above.

The classification mentioned above based mainly on shape of virus and virus genome. The scope of the viruses capable of applying the antiviral agent of the present invention is not necessarily restricted to this classification.

The application method and application form of the antiviral agent of the present invention are not particularly limited insofar as the active ingredient can demonstrate the antiviral activity in the object of administration.

For example, the present RtIB026 strain can be orally administered. For oral administration of the present RtIB026 strain into fish, crustaceans etc., the present strain can be mixed with feed or administered forcibly through a cannula. Further, the RtIB026 strain can be added to any feed for raising fish. When this strain is mixed with feed, a lyophilized powder of the RtIB026 strain is dispersed in e.g. liver oil and then added to feed.

The dose can be suitably established by those skilled in the art depending on the type of the intended animal, the living environment of the animal, the type of the intended virus, the severity of disease, etc. To give an example, rainbow trout raised outdoors in a farm, the onset of the diseases can be prevented and the yield can be improved by adding $10^4$ to $10^8$ CFU of RtIB026 strain to 1 g of feed.

For administration into fish and crustaceans, the present RtIB026 strain can be administered by immersion. In addition, an application method besides the administration includes allowing the RtIB026 strain of the present invention to grow in raising water. Further, the present RtIB026 strain may be allowed to grow in a filter material with which the viruses in raising water is inactivated, whereby the effect can be demonstrated.

From the viewpoint of the antiviral activity, the present RtIB026 strain is administered preferably in a living state to the animals.

On the other hand, the method or mode of administering the present peptides (MA026, R1MA026 and R2MA026) and the derivatives (AL-MA026, BTI-MA026 and BTI-base MA026) of the present peptide MA026, as well as salts thereof, is not particularly limited insofar as the antiviral activity can be demonstrated, and these can be administered orally, by injection, or by spray, etc.

In the case, for example, of oral administration into humans or other vertebrates, the preparation can be formulated in the form of tablets, capsules, powder, granules, solution, suspension etc. without any limitation to the form. The method of manufacturing such preparations is not particularly limited either, and can be conducted by any method known in the art. For example, the present peptide and/or derivative thereof can be formed into tablets by mixing it with binders such as crystalline cellulose, tablet disintegrators such as corn starch, lubricants such as talc, and if necessary with a diluent, a buffering agent etc. For parenteral administration by injection etc., the present peptide and/or derivative thereof can be dissolved, suspended or emulsified in aqueous or non-aqueous solvents such as vegetable oils, synthetic glyceride etc., if necessary with additives such as a solubilizer etc. to prepare the intended preparation. Further, the peptides of the present invention can be administered by spray directly on focus.

When the present peptides are applied to a domestic animal, the peptides can also be sprayed in the breeding environment of the animal, besides directly administering the peptides to the animal.

For oral administration into fish and crustaceans, the present peptide and/or derivative thereof, similar to the present RtIB026 strain described above, can be mixed with feed or administered forcibly through a cannula. It can also be administered through immersion or by directly adding the present RtIB026 to raising water. In the case of administration by injection, the present peptide and/or its derivative can be administered by dissolving it in a solvent such as physiological saline used ordinarily in pharmaceutical preparations.

The dose can be suitably established by those skilled in the art depending on the type and weight of the intended animal, the raising environment in the case of fish, the type of intended virus, the severity of disease, etc.

EXAMPLES

The present invention is described by reference to the Examples, which however are not intended to limit the present invention.

Example 1

<Isolation of the Present RtIB026 Strain from Bred Rainbow Trout>

1. A rainbow trout (weight 460 g; length 34.5 cm) used as a donor of the present strain was a fish raised in a fish farm in Yamanashi Pref., Japan.
2. The abdomen of the rainbow trout in 1 above was opened, and the digestive tract was excised. The digestive tract was opened by cutting it with a sterilized surgical knife and placed in a culture broth a) shown below and cultured at 25° C. for 5 days.
3. A part of the culture obtained in 2 above was spread onto a plate medium shown in b) below and cultured, and 32 colonies were selected at random from the resultant colonies. The selected colonies were subjected at least twice to streak culture on the same plate medium to isolated pure strains.
4. Each of the isolated strains was cultured at 25° C. for 5 days in the medium in a) below to give a culture supernatant (from which the microorganism was removed by filtration). The supernatant was evaluated for its antiviral activity in cultured cells, and as a result, one strain (RtIB026 strain) having a strong antiviral activity was obtained.

Evaluation of the antiviral activity was conducted by the same method as described by Burke et al. (Appln. Env. Microbiol., 29, 872-876, 1980) except for the following partial modification.

(1) A sample to be measured for its antiviral activity is dissolved in dimethyl sulfoxide (DMSO) and then diluted with Hank's solution.
(2) 0.2 mL each of the diluted solution in (1) and a viral solution (IHNV HV7601 strain; 100 to 200 PFU/sample) diluted with Hank's solution are mixed and incubated at 10° C. for 2 hours.
(3) After the incubation in (2), the sample is inoculated for 30 minutes in CHSE-214 cells previously cultured for 24 hours in a 24-well cell culture plate.
(4) The sample is removed from each well, and an MEM medium containing. 0.8% methyl cellulose is overlaid on the cells and cultured for 7 days.
(5) The cells on the culture plate are fixed in 3.7% aqueous formalin, and after staining with 1% Crystal Violet, the number of plaques is counted.
(6) The antiviral activity is expressed in terms of the decrease in the number of plaques, relative to that decrease on wells to which the sample was not added.

(Composition of the Medium)
a) 5.00 g polypeptone, 2.50 g meat extract, 2.50 g yeast extract, 0.20 g $K_2HPO_4$, 0.05 g $MgSO_4$, 1.00 g glucose, 5.00 g NaCl, 1000 mL distilled water, pH 7.5, which were autoclaved at 121° C. for 15 minutes.
b) 15.00 g agar for microorganisms is added to a).

In the following examples, the evaluation of the antiviral activity was conducted in the method described above.

Example 2

<Purification of the Present Peptides MA026, R1MA026 and R2MA026 from a Culture of the Present RtIB026 Strain>

1. Preparation of the Culture Filtrate
The RtIB026 strain obtained in Example 1 above was cultured in a culture broth with the composition shown in Table 3 below.

TABLE 3

Medium Composition

Solution of preservative salts

| | |
|---|---|
| EDTA (2Na) | 2.5 g |
| $ZnSO_4 \cdot 7H_2O$ | 10.95 g |
| $FeSO_4 \cdot 7H_2O$ | 5.0 g |
| $MnSO_4 \cdot H_2O$ | 1.54 g |
| $CuSO_4 \cdot 5H_2O$ | 0.392 g |
| $Co(NO_3)_2 \cdot 6H_2O$ | 0.248 g |
| $Na_2B_4O_7 \cdot 10H_2O$ | 0.177 g |
| Distilled water | 1000 mL |

Mineral solution

| | |
|---|---|
| Nitrilotriacetic acid | 10 g |
| $MgSO_4$ | 14.45 g |
| $CaCl_2 \cdot 2H_2O$ | 3.34 g |
| $(NH_4)_6Mo_7O_{24} \cdot 4H_2O$ | 0.009 g |
| $FeSO_4 \cdot 7H_2O$ | 0.1 g |
| Solution of preservative salts | 50 mL |
| Distilled water | 950 mL |
| Adjusted to pH 6.8 (KOH) | |

Standard mineral base

| | |
|---|---|
| 0.5 M $Na_2HPO_4$ + $KH_2PO_4$ buffer | 80 mL |
| Mineral solution | 20 mL |
| $(NH_4)_2SO_4$ | 1 g |
| Distilled water | 900 mL |

Yeast extract medium

| | |
|---|---|
| Yeast extract | 5 g |
| Standard mineral base | 1000 mL |

The microorganism previously subjected to slant culture was inoculated via a platinum loop onto the same medium and cultured overnight at 25° C. and 5 ml of the culture was added to 2.5 L of the same medium and cultured at 25° C. for 5 days. The culture was centrifuged, and the supernatant was filtered through a 0.45 μm membrane filter to remove the microorganism. The culture filtrate, 20 L/lot, was subjected to the following purification.

2. Concentration and Desalting of Culture Filtrate

The culture filtrate prepared in 1 was passed through a Diaion HP-20SS (62.5×120 mm) column and washed in succession with 5 L deionized water and 80% aqueous methanol (3 L). Then, a fraction containing the desired substance was eluted with 95% aqueous methanol. Further, this fraction was concentrated under reduced pressure, suspended in water and passed again through Diaion HP-20SS (95×45 mm). The column was washed with 1 L deionized water and 1 L of 80% aqueous methanol in the same manner as above, and then a fraction containing the desired substance was eluted with methanol.

3. Separation of Desired Substance (1) Purification by Silica Gel Column Chromatography The fraction obtained in 2 was evaporated into dryness under reduced pressure and dissolved in a small amount of a solvent having the following composition. This solution was applied onto a silica gel column (Wakogel C-300HG) previously equilibrated with the same solvent, and eluted and fractionated with the same solvent [elution solvent; ethyl acetate:methanol:water=100:25:15 (v/v/v)]. The desired substance was detected by development with thin-layer chromatography with the above solvent (a spot with Rf=0.25 was detected by coloration with 0.2% vanillin/sulfuric acid solution).

(2) Purification by High Performance Liquid Chromatography

A fraction containing the desired substance obtained in (1) above was concentrated under reduced pressure, then dissolved in 92% aqueous methanol and purified by high performance liquid chromatography (HPLC) equipped with an ODS column (YMC-Pack R&D ODS, 20×250 mm). Separation was conducted under the conditions where the flow rate was 5.0 mL/min., the detection wavelength was 220 nm, and the elution solvent was 92% aqueous methanol. A chromatogram of this HPLC is shown in FIG. 1.

Fractions showing peaks at retention times of 17.7 minutes (peak No. 1: R1MA026 fraction), 19.0 minutes (peak No. 2: MA026 fraction) and 21.4 minutes (peak No. 3: R2MA026 fraction) were collected respectively and concentrated under reduced pressure. Then, each of the concentrated fractions was dissolved again in 92% aqueous methanol and separated again under the same conditions as described above. Purification was completed by collecting each desired substance as a fraction showing a single peak.

From the culture (20 L/lot) of the present RtIB026 strain obtained by the method described above, the present peptides MA026, R1MA026 and R2MA026 were obtained in amounts of 50 mg, 1 mg and 5 mg, respectively. The proportion of the present peptides MA026, R1MA026 and R2MA026 is not limited to that set forth in this example. A proportion of a desired peptide may be increased by properly adjusting the culture conditions (temperature, pH, medium composition, oxygen concentration, bacterial state, etc.).

Example 3

<Preparation of the Present Peptide BTI-MA026 (Hofmann Rearrangement)>

The present peptide MA026 and bistrifluoroacetoxyiodobenzene (BTI), 10 mg/mL, were allowed to react in 50% aqueous acetonitrile at 60° C. in a nitrogen atmosphere for 4 hours.

From the reaction mixture, the unreacted BTI was removed with diethyl ether, and the reaction product was purified by gel filtration (Sephadex LH-20 column, 10×180 mm, methanol solution) to give the present peptide BTI-MA026.

Example 4

<Preparation of the Present Peptide BTI-Base MA026>

The present peptide BTI-MA026 was allowed to react in 50% dimethylamine solution at room temperature for 3 hours, then purified with high performance liquid chromatography to obtain the present peptide BTI-base MA026.

Example 5

<Preparation of the Present Peptide AL-MA026>

One of the present peptides AL-MA026 having the above formula (VI) wherein R is a methyl group, was synthesized through methylation of the present peptide MA026 by reacting iodomethane in dimethylformamide solution in a presence of $NaHCO_3$.

Measurement Example 101

Figure 2:
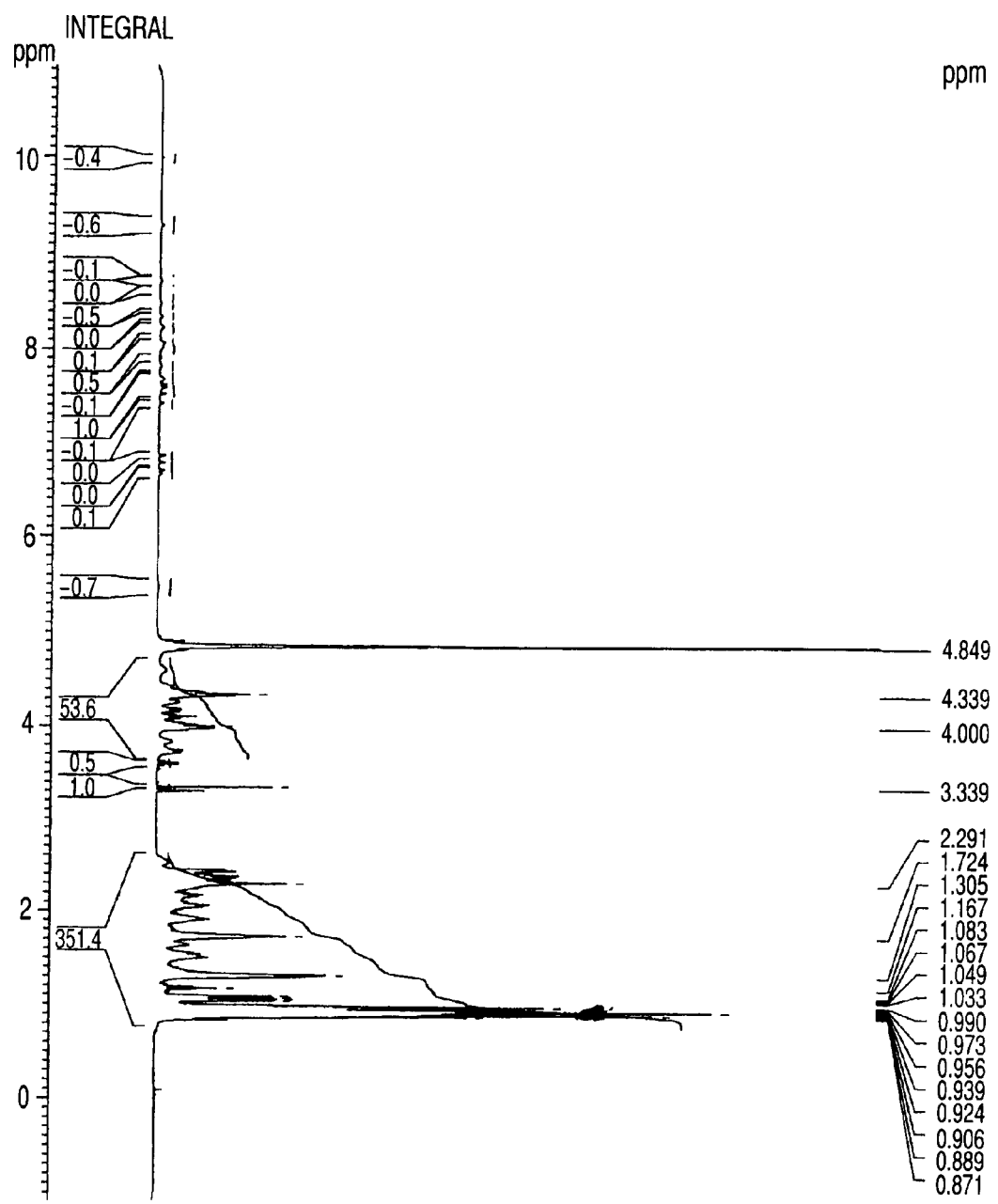
FIG. 2 is a chart of proton NMR spectrum.

A proton NMR chart of the present peptide MA026 purified in Example 2 is shown in FIG. 2.

Measurement Example 102

Figure 3:
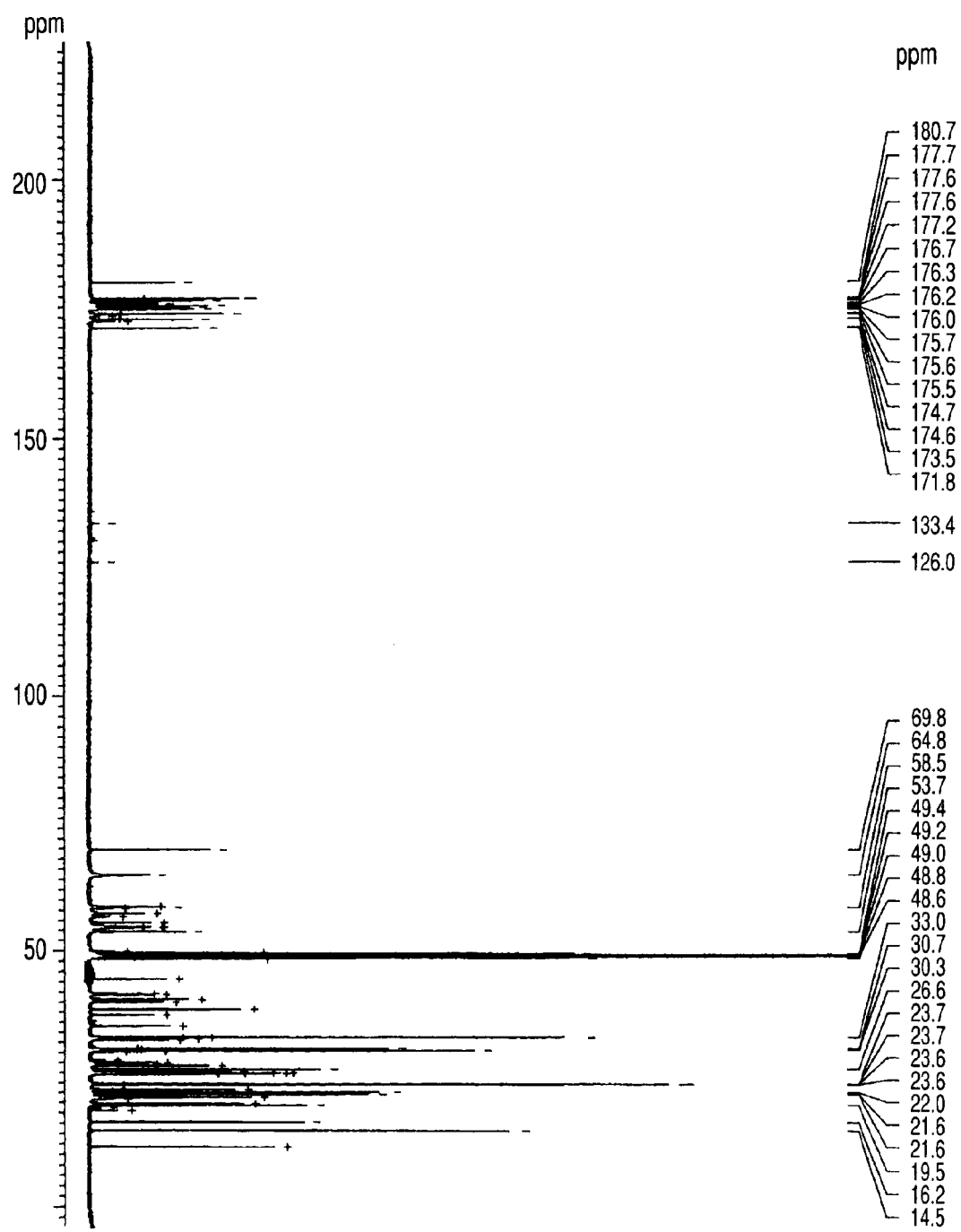
FIG. 3 is a chart of carbon-13 NMR spectrum.

A carbon-13 NMR chart of the present peptide MA026 purified in Example 2 is shown in FIG. 3.

Measurement Example 103

Figure 4:
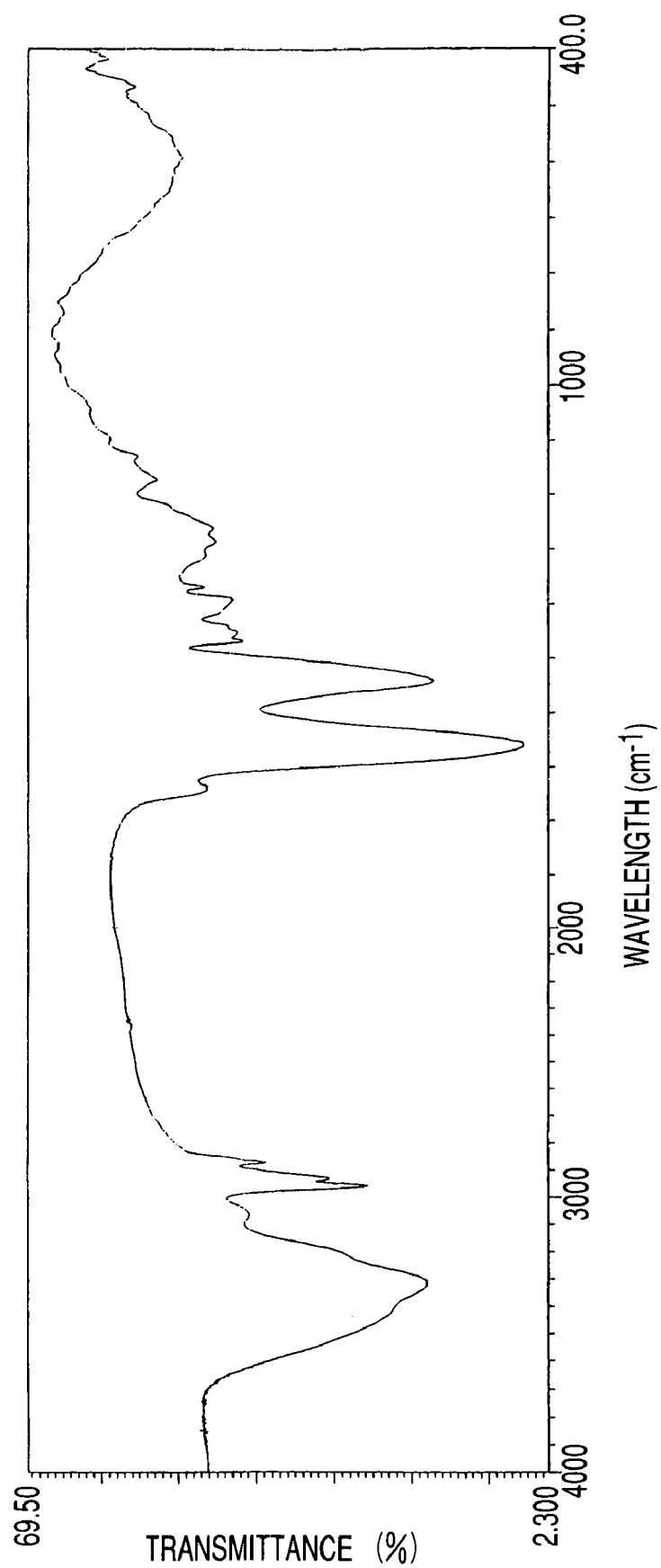
FIG. 4 is an infrared absorption spectrogram.

An infrared absorption spectrum of the present peptide MA026 purified in Example 2 is shown in FIG. 4.

Measurement Example 104

Figure 5:
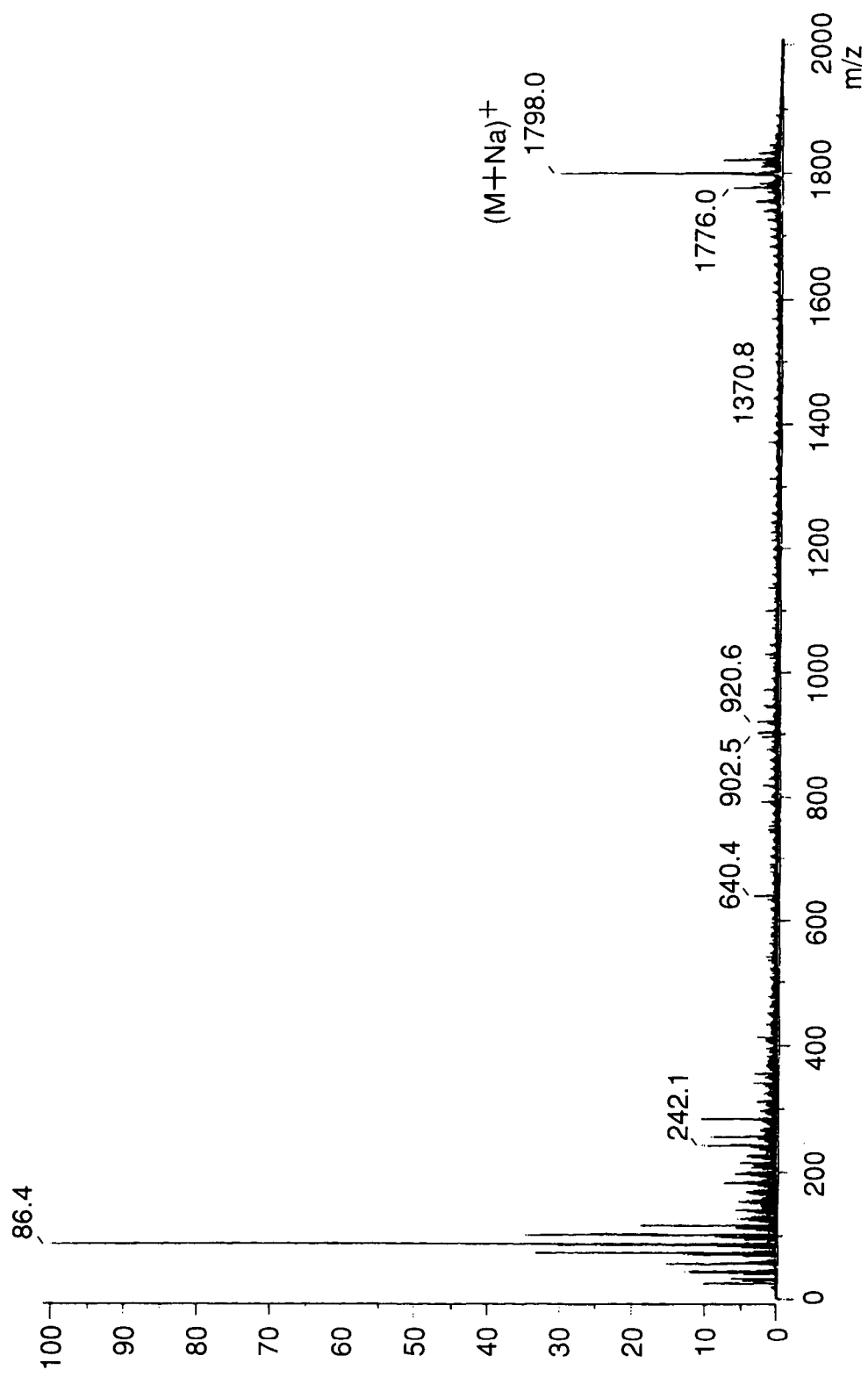
FIG. 5 is a positive FAB-MS spectrogram.

A positive FAB-MS spectrogram of the present peptide MA026 purified in Example 2 is shown in FIG. 5.

Measurement Example 105

Figure 6:
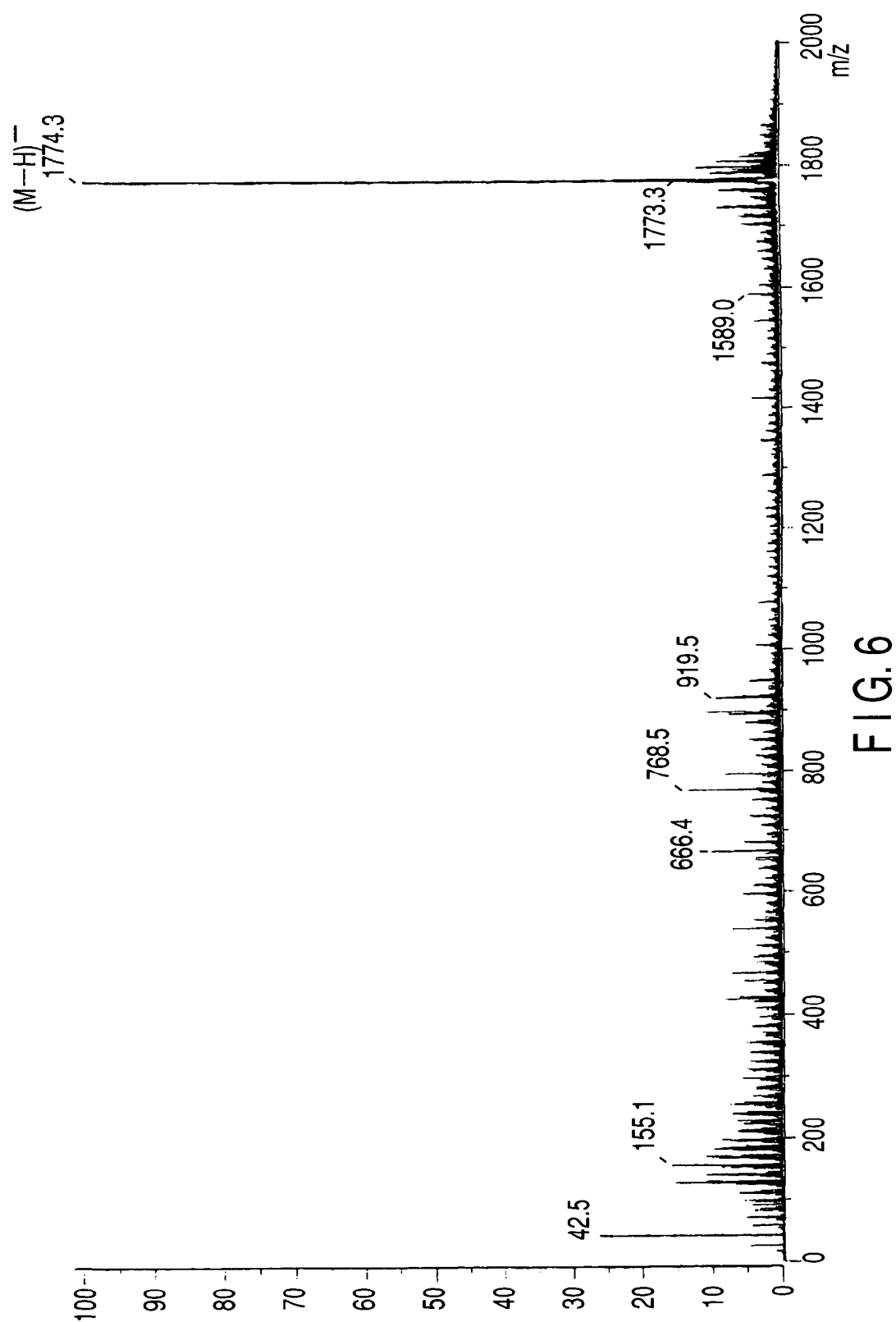
FIG. 6 is a negative FAB-MS spectrogram.

A negative FAB-MS spectrogram of the present peptide MA026 purified in Example 2 is shown in FIG. 6.

Measurement Example 106

High-resolution mass spectrometric analysis of the present peptide MA026 purified in Example 2 was conducted. The molecular formula deduced from the found value of 1776.0829 (M+H)$^+$ was $C_{84}H_{146}O_{23}N_{18}$. The molecular weight calculated from this molecular formula is 1775.0811.

Measurement Example 107

Elemental analysis of the present peptide MA026 purified in Example 2 was conducted, and the results shown in Table 4 below were obtained.

TABLE 4

|  | C % | H % | N % |
|---|---|---|---|
| Analysis result | 55.04 | 8.17 | 13.75 |
| (readings of twice | 54.97 | 8.17 | 13.75 |
| measurements) |  |  |  |
| Theoretical | 56.80 | 8.29 | 14.19 |

Noted feature:
The sample was hygroscopic and left ash.

Measurement Example 108

The decomposition point of the present peptide MA026 (amorphous state) purified in Example 2 was determined to be 174° C.

Measurement Example 109

The specific rotation of the present peptide MA026 purified in Example 2 was determined to be $[\alpha]_D^{17}=-29.5°$ (c1.0, MeOH)

Measurement Example 110

Figure 7:
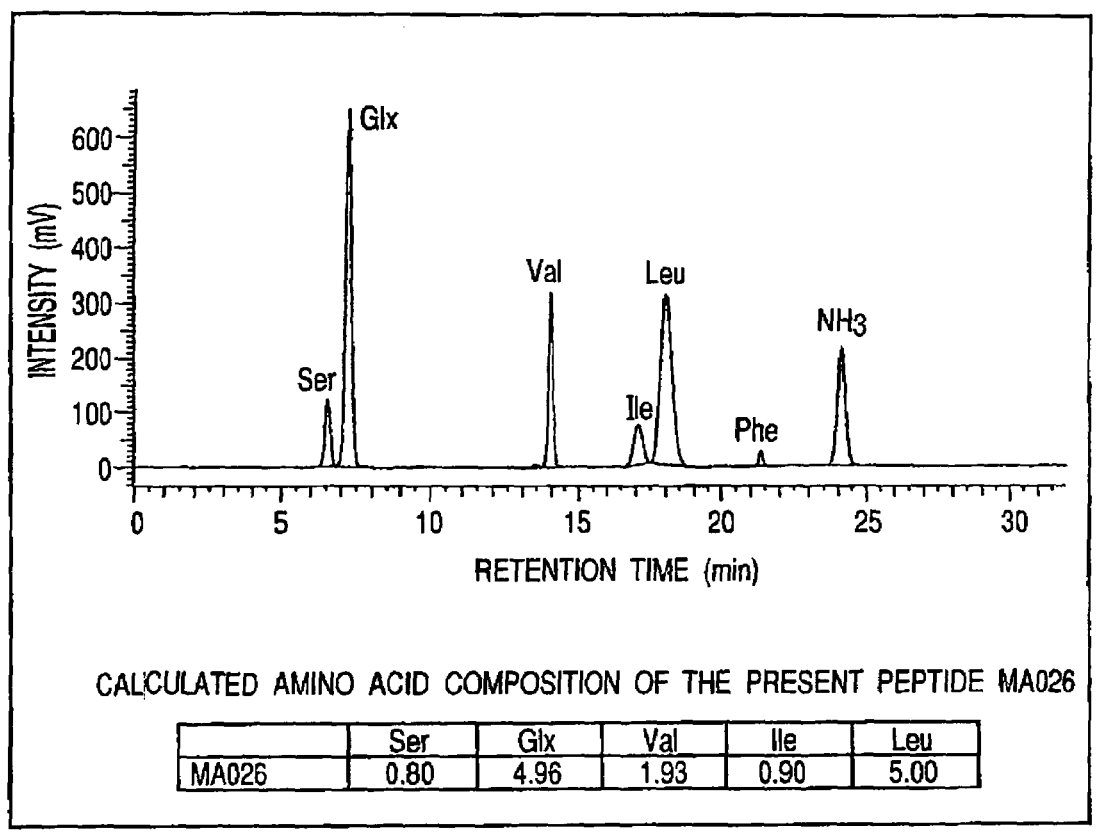
FIG. 7 is an amino acid analysis chart.

The result of amino acid analysis of the present peptide MA026 purified in Example 2 is shown in FIG. 7.
For this amino acid analysis, the present peptide MA026 was hydrolyzed with 6 N hydrochloric acid at 110° C. for 24 hours and analyzed by an amino acid analyzer. Every acid hydrolysis in the following Measurement Examples was conducted under the same acid hydrolysis conditions as in Measurement Example 110.

Measurement Example 111

The product (the present peptide BTI-MA026) of a Hofmann rearrangement of the present peptide MA026 obtained in Example 3 was analyzed in the following manner.
The present peptide BTI-MA026 (1.8 mg) was hydrolyzed with the acid and analyzed by an amino acid analyzer.
The calculated amino acid compositions before and after the Hofmann rearrangement are shown Table 5 below.

TABLE 5

|  | Ser | Glx | Val | Ile | Leu |
|---|---|---|---|---|---|
| Before reaction | 0.80 | 4.96 | 1.93 | 0.90 | 5.00 |
| After reaction | 0.78 | 0.99 | 2.00 | 0.90 | 5.00 |

The glutamine residues in the present peptide MA026 are converted into α,γ-diaminobutyric acid residues in the Hofmann rearrangement, thereby a number of glutamine residues can be estimated through the amino acid analysis.
By comparing the compositions before and after the rearrangement shown in Table 5 above, the molecular ratio of the number of glutamine residues and glutamic acid residues in the present peptide MA026 was estimated to be 4:1. Therefore, the constitutive amino acid residues in the present peptide MA026 were estimated to be 4 glutamine residues, 1 glutamic acid residue, 1 serine residue, 2 valine residues, 1 isoleucine residue and 5 leucine residues.

Measurement Example 112

The present peptide MA026 was reacted for 20 hours with lithium borohydride (LiBH$_4$) in a methanol solution at room temperature.
The reaction product was neutralized with 0.1 N hydrochloric acid, and an excess of water was added, and the product was extracted with butanol.
A part (2.0 mg) of the reaction extract was hydrolyzed with the acid and analyzed by an amino acid analyzer.
The calculated amino acid compositions are shown in Table 6 below.

TABLE 6

|  | Ser | Glx | Val | Ile | Leu |
|---|---|---|---|---|---|
| Before reaction | 0.82 | 5.50 | 1.99 | 0.88 | 5.00 |
| After reaction | 0.85 | 5.06 | 1.95 | 0.16 | 5.00 |

The ester linkage contained in the present peptide MA026 is cleaved by the reduction reaction with LiBH$_4$, thereby the carboxy group in the linkage is converted into a hydroxy group. The amino acid at the carboxy side of the amino acids participating in the ester linkage can be estimated from the reaction.
From the results shown in Table 6 above, it is estimated that the amino acid residue at the carboxy side of the ester linkage forming the cyclic structure of the present peptide MA026 is isoleucine.

Measurement Example 113

(1) The present peptide MA026 was reacted with a solution of 100 mg CrO$_3$ and 0.1 mL pyridine in 3 mL acetic acid at room temperature for 20 hours.
An excess of water was added to the reaction product which was then extracted with butanol.

A part (4.5 mg) of the reaction extract was hydrolyzed with the acid and analyzed by an amino acid analyzer.

(2) Separately, the present peptide MA026 was dissolved in 50% aqueous dimethyl amine and reacted for 3 hours at room temperature.

The reaction product was dried under reduced pressure and subjected to oxidation reaction with $CrO_3$ in the same manner as in (1) above to give a reaction product.

A part (6.8 mg) of the reaction product was hydrolyzed with the acid and analyzed by an amino acid analyzer.

The respective calculated amino acid compositions are shown in Table 7 below.

TABLE 7

|  | Ser | Glx | Val | Ile | Leu |
|---|---|---|---|---|---|
| Before reaction of (1) and (2) | 0.82 | 5.50 | 1.99 | 0.88 | 5.00 |
| After reaction of (1) | 0.72 | 4.65 | 1.89 | 0.82 | 5.00 |
| After reaction of (2) | 0.37 | 4.73 | 1.90 | 0.86 | 5.00 |

The oxidation reaction with $CrO_3$ oxidatively converts the hydroxy group of the present peptide MA026 into ketone, thereby an amino acid having a free hydroxy group does not exist any more. Further, the ester linkage is cleaved through alkali hydrolysis reaction in the reaction of (2). The amino acid at the hydroxy side of the amino acids participating in the ester linkage can be estimated by the amino acid analysis of the above oxidation product and the reaction product.

From the results shown in Table 7 above, it is estimated that the amino acid residue at the hydroxy side of the ester linkage forming the cyclic structure of the present peptide MA026 is serine.

Measurement Example 114

The present peptide MA026 was dissolved in methanol and mixed with an equal volume of diethyl ether.

Diazomethane captured in ether was added in excess, and the mixture was allowed to react for 1 hour in a sealed vessel at room temperature.

The reaction product was dried under reduced pressure and separated and purified by high performance liquid chromatography. Separation was conducted under the conditions where the flow rate was 5.0 mL/min., the detection wavelength was 220 nm and the elution solvent was 92% aqueous methanol.

The purified product was subjected to a reduction reaction with lithium borohydride in the same manner as in Measurement Example 112 above.

A part (0.1 mg) of the reaction product was hydrolyzed with the acid and analyzed for its amino acids.

The calculated amino acid compositions are shown in Table 8.

TABLE 8

|  | Ser | Glx | Val | Ile | Leu |
|---|---|---|---|---|---|
| Before reaction | 0.80 | 4.96 | 1.93 | 0.90 | 5.00 |
| After reaction | 0.75 | 4.20 | 1.84 | 0.19 | 5.00 |

From the results in Table 8 above, it is estimated that only the glutamic acid of the present peptide MA026 has a free carboxy group.

Measurement Examples 115 and 116

The present peptide MA026 was subjected to acid hydrolysis with 6 N HCl at 94° C. for 14 hours, and the resultant acid hydrolyzates were extracted with diethyl ether.

The extract was methylated with diazomethane in the same manner as in Measurement Example 114.

The methylated products were purified by silica gel column chromatography to give fractions, out of which a fraction showing an Rf value of 0.51 in thin layer chromatography {developing solvent:ethyl acetate/methanol/water=100:25:15 (v/v/v)} was collected. Proton and carbon-13 nuclear magnetic resonance (NMR) spectra of this collected sample were taken to give the following results.

$^1$H NMR (400 MHz, $CDCl_3$+TMS, Δppm) 0.88 (3H, t, J=6.9, H10), 0.94 (3H, d, J=6.3, H6'). 0.95 (3H, d, J=6.1, H5'), 1.28 (10H, br, H5-9), 1.39-1.46 (1H, m, H4a), 1.50-1.58 (2H, m, H4b&H3'a), 1.60-1.69 (2H, m, H4'&H3'b), 2.30 (1H, dd, J=8.7&15.3, H2a), 2.43 (1H, dd, J=2.8&15.3, H2b), 3.74 (3H, s, Me), 3.99 (1H, m, H2), 4.65 (1H, td, J=4.9&8.7, H2'), 6.13 (1H, d, J=8.2, NH) $^{13}$C NMR (100 MHz, $CDCl_3$+TMS, Δppm) 14.1 (C10), 21.9 (C6'), 22.6 (C9), 22.8 (C5'), 24.9 (C4'), 25.5 (C5), 29.2 (C7), 29.5 (C6), 31.8 (C8). 36.7 (C4), 41.5 (C3'), 42.4 (C2), 50.6 (C2'), 52.4 (Me), 68.6 (C3), 172.2 (C1), 173.6 (C1')

From these data, structure of the hydrolysis product was decided to be the structural formula (XI) below:

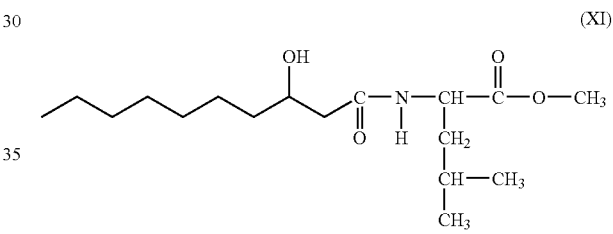

(XI)

From these results, it is estimated that the N-terminal amino acid residue of the present peptide MA026 is leucine, and a 3-hydroxydecanoyl group is bonded, via an amide linkage, to this leucine.

Measurement Example 117

Figure 8:
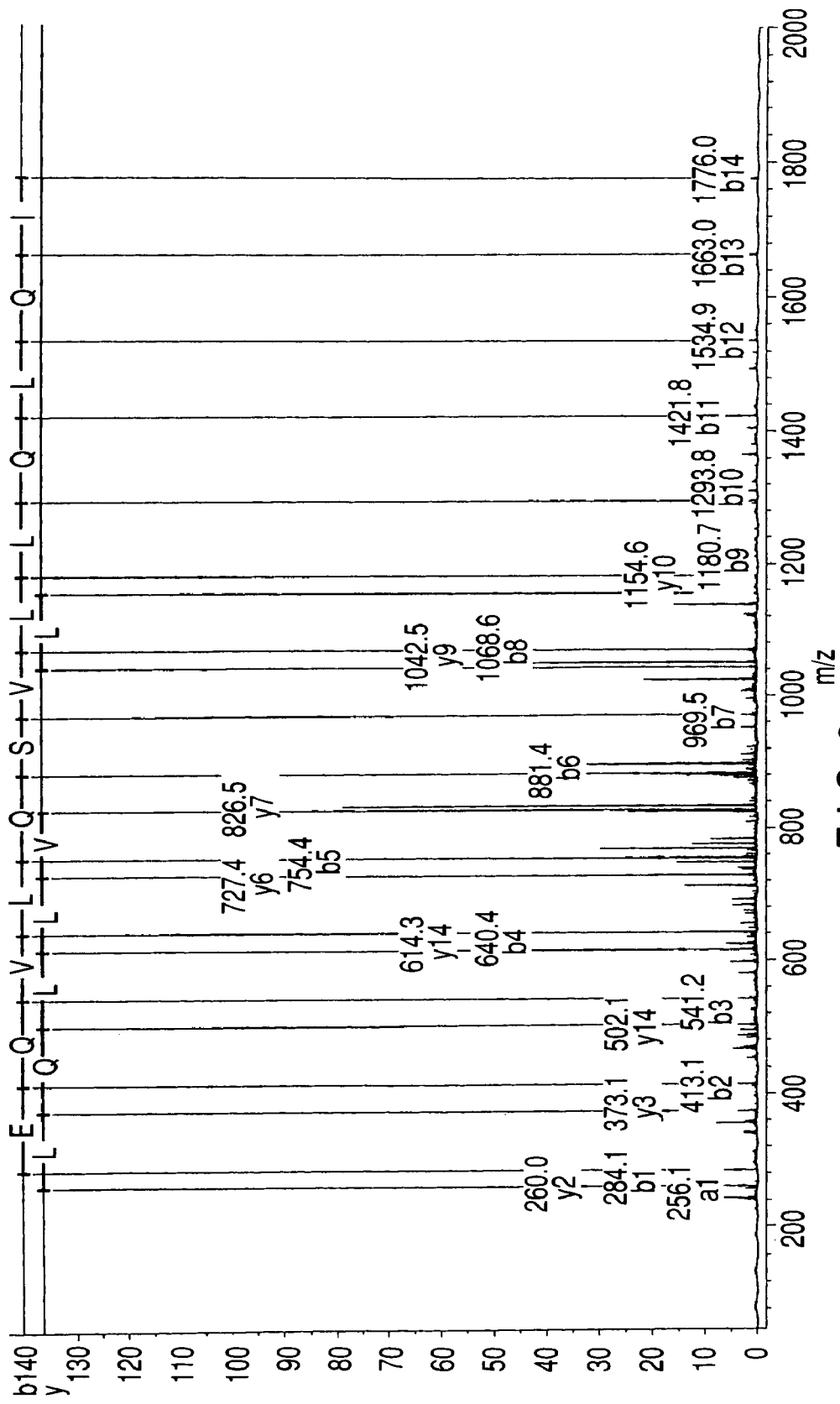
FIG. 8 is a positive ESI-MS/MS spectrogram.

A positive ESI MS/MS spectrum of the present peptide MA026 is shown in FIG. 8.

Measurement Examples 118 to 120

The present peptide BTI-MA026 obtained in Example 3 was subjected to proton and carbon-13 NMR in methanol-$d_4$, and ESI-MS spectrometric analysis.

Figure 9:
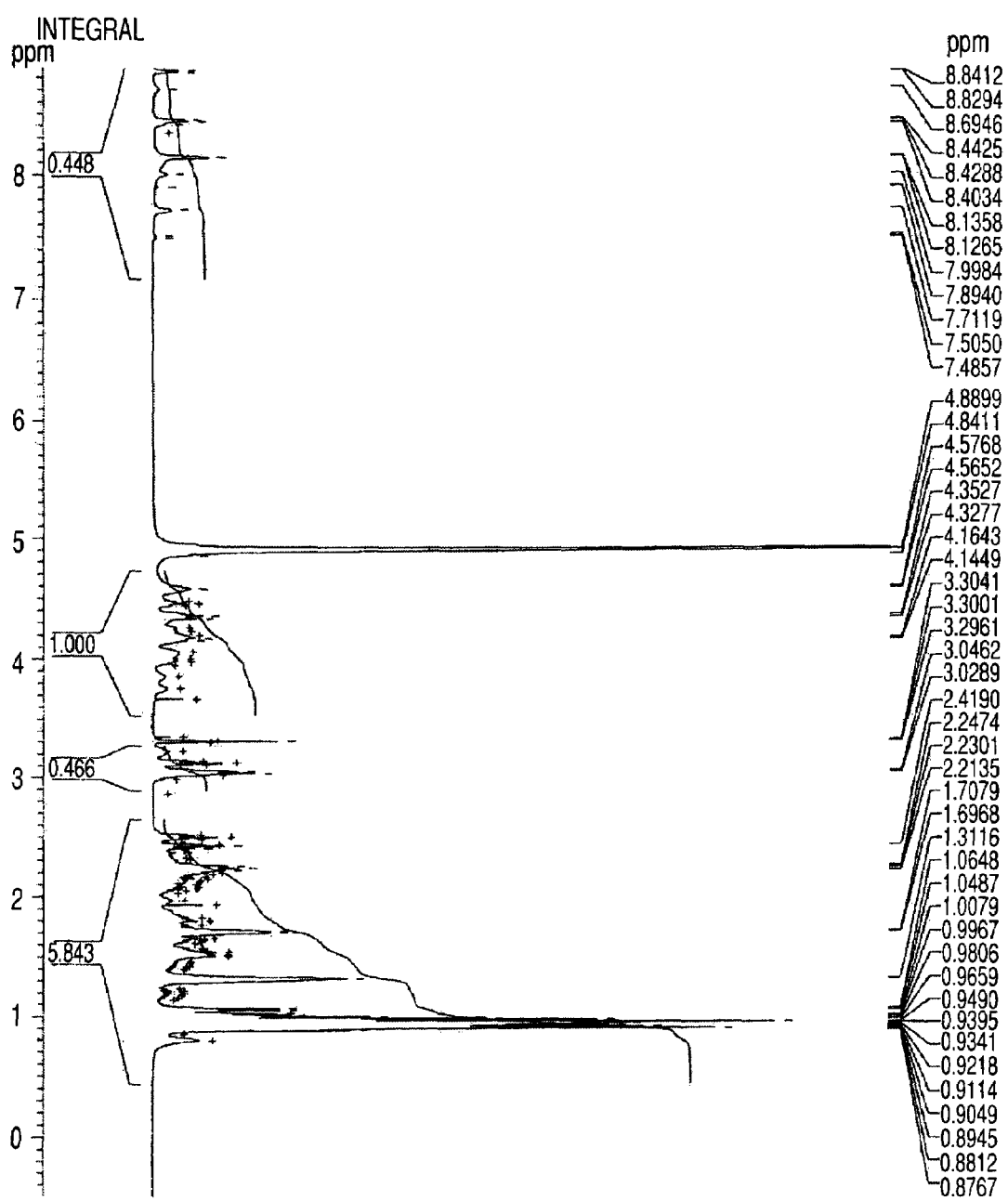
FIG. 9 is a chart of proton NMR spectrum.
Figure 10:
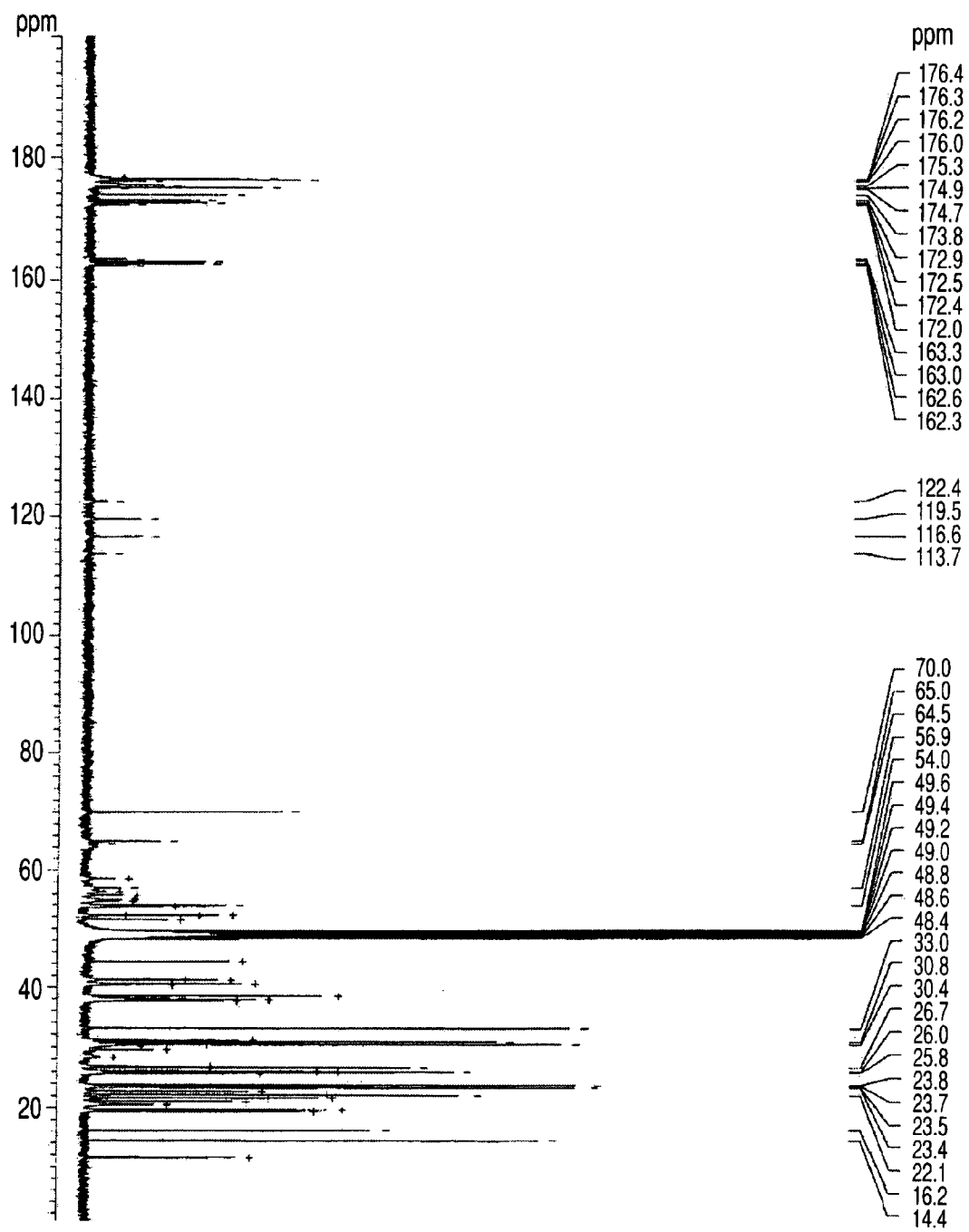
FIG. 10 is a chart of carbon-13 NMR spectrum.
Figure 11:
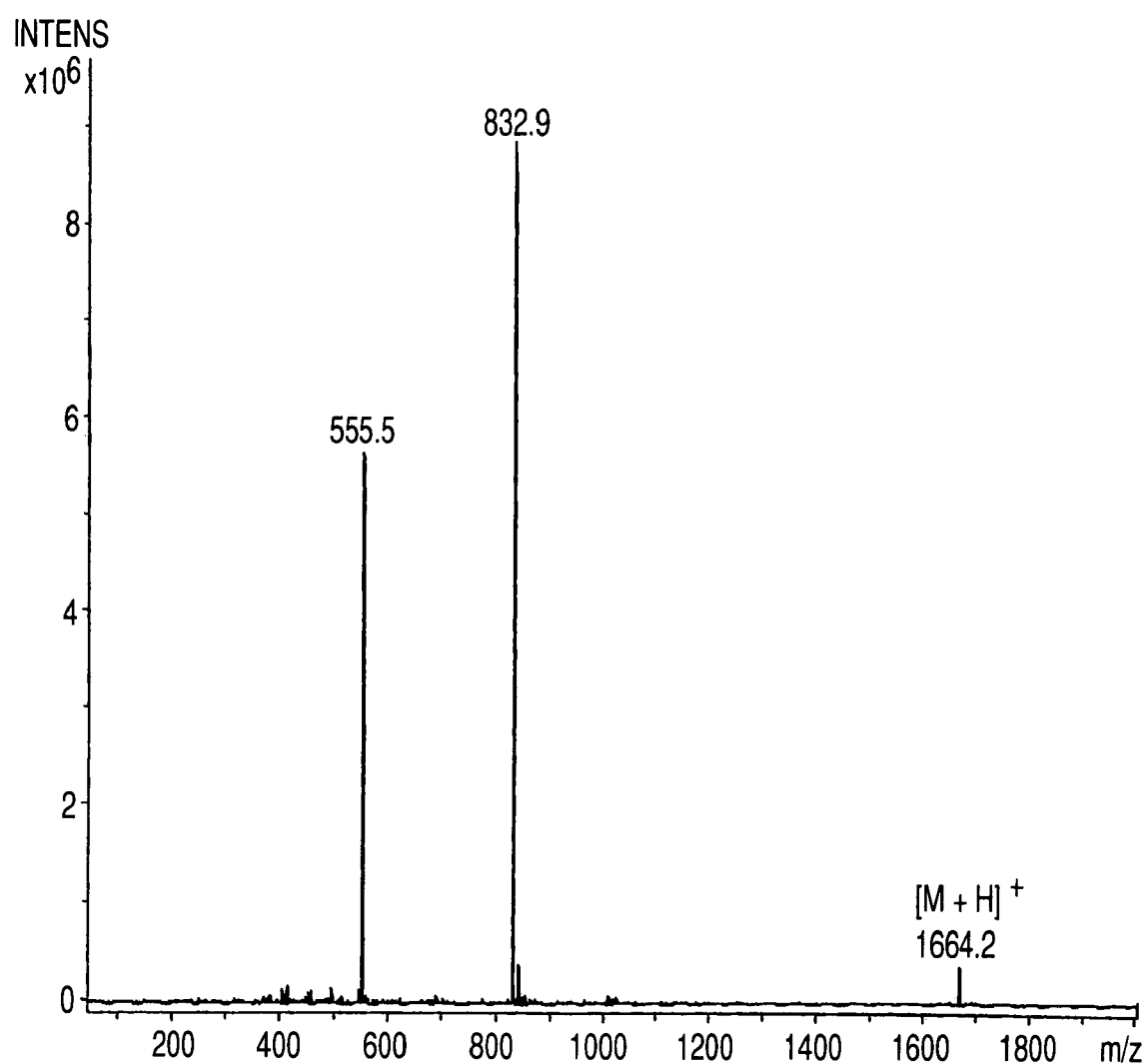
FIG. 11 is an ESI-MS spectrogram chart.

FIGS. 9 and 10 show the proton and carbon-13 NMR spectra respectively, and the result of the ESI-MS spectrometric analysis is shown in FIG. 11.

Measurement Example 121

Figure 12:
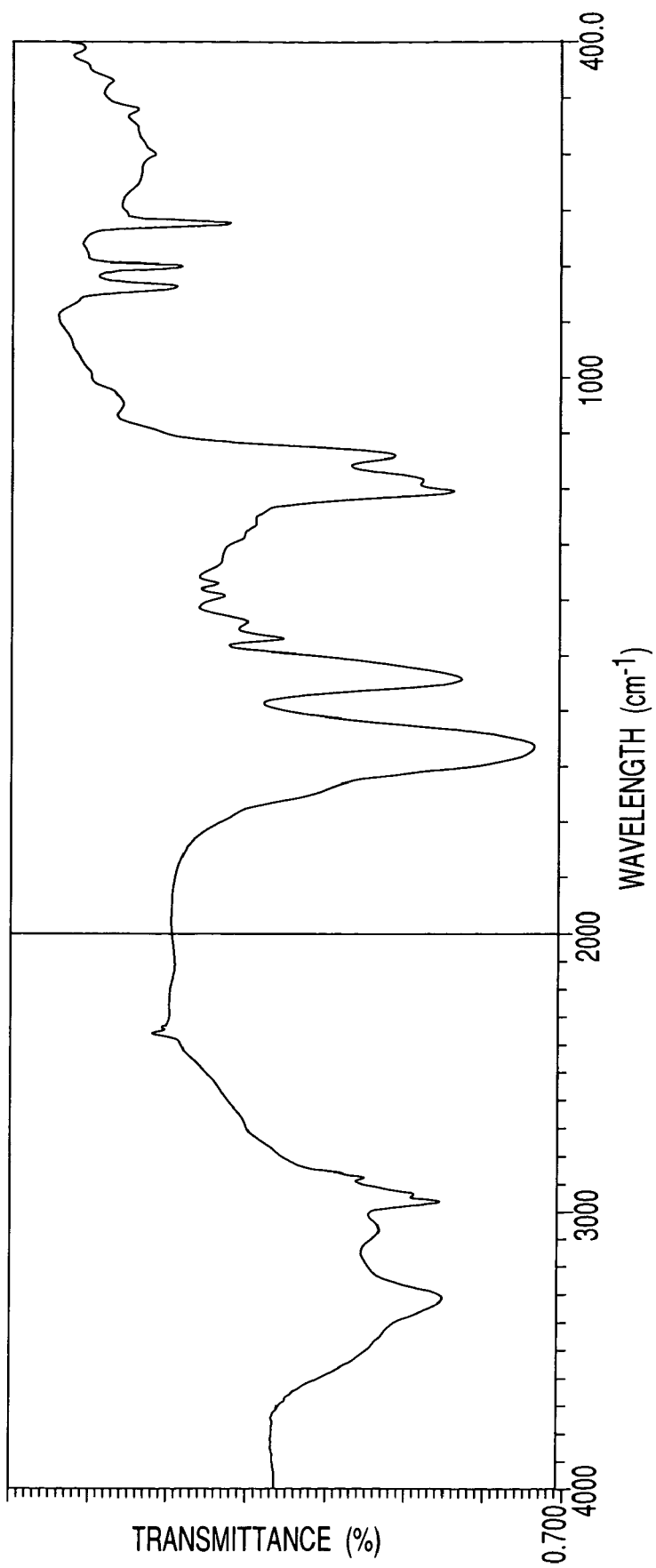
FIG. 12 is an infrared absorption spectrogram.

An infrared absorption spectrum of the present peptide BTI-MA026 is shown in FIG. 12.

Measurement Example 122

The specific rotation of the present peptide BTI-MA026 was determined to be $[\alpha]_D^{24}$=−0.3° (c1.0, MeOH)

Measurement Example 123

The decomposition point of the present peptide BTI-MA026 (amorphous state) was determined to be 165° C.

Measurement Examples 124 to 126

The present peptide BTI-base MA026 obtained in Example 4 was subjected to proton and carbon-13 NMR in methanol-$d_4$, and ESI-MS spectrometric analysis.

Figure 13:
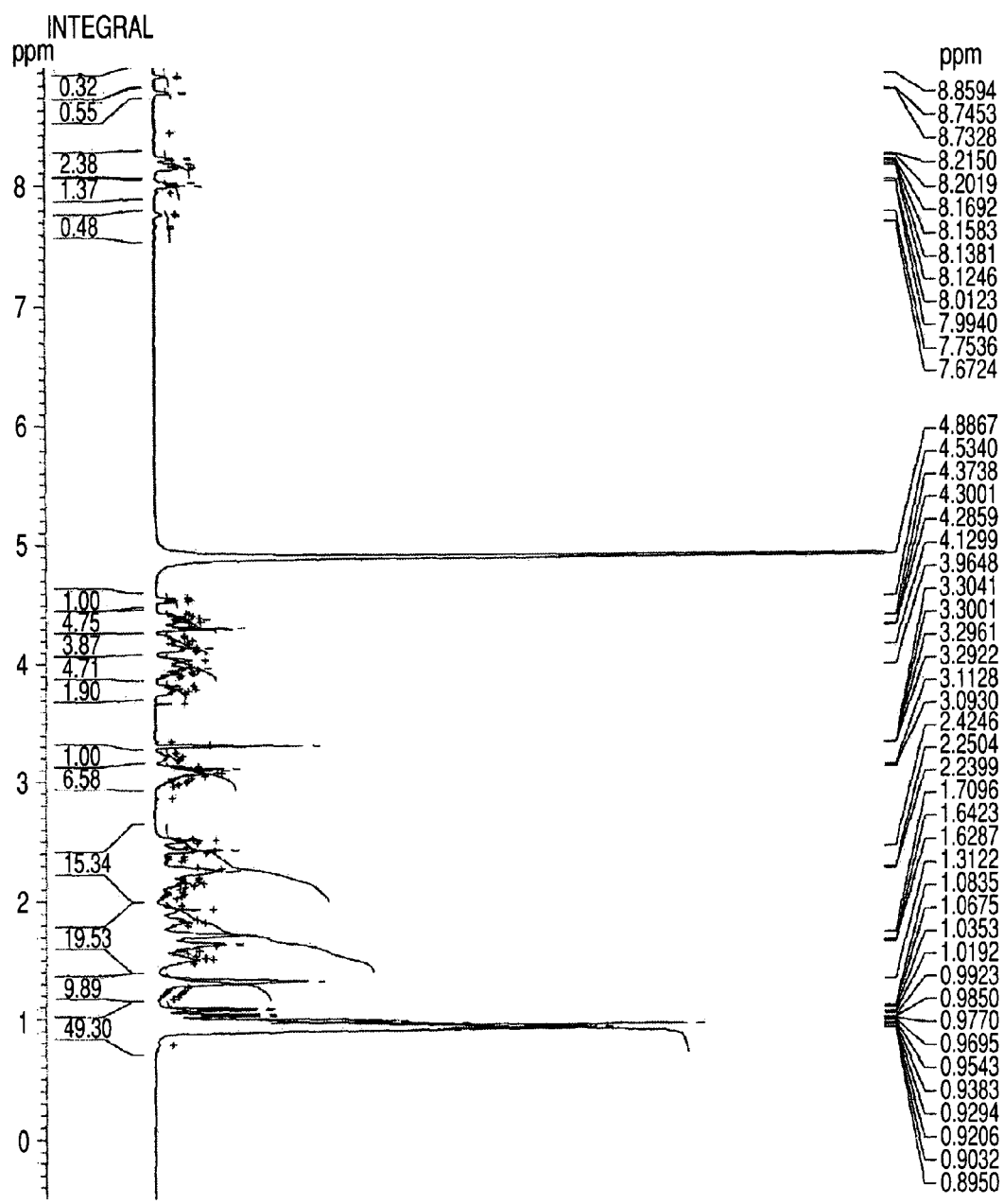
FIG. 13 is a chart of proton NMR spectrum.
Figure 14:
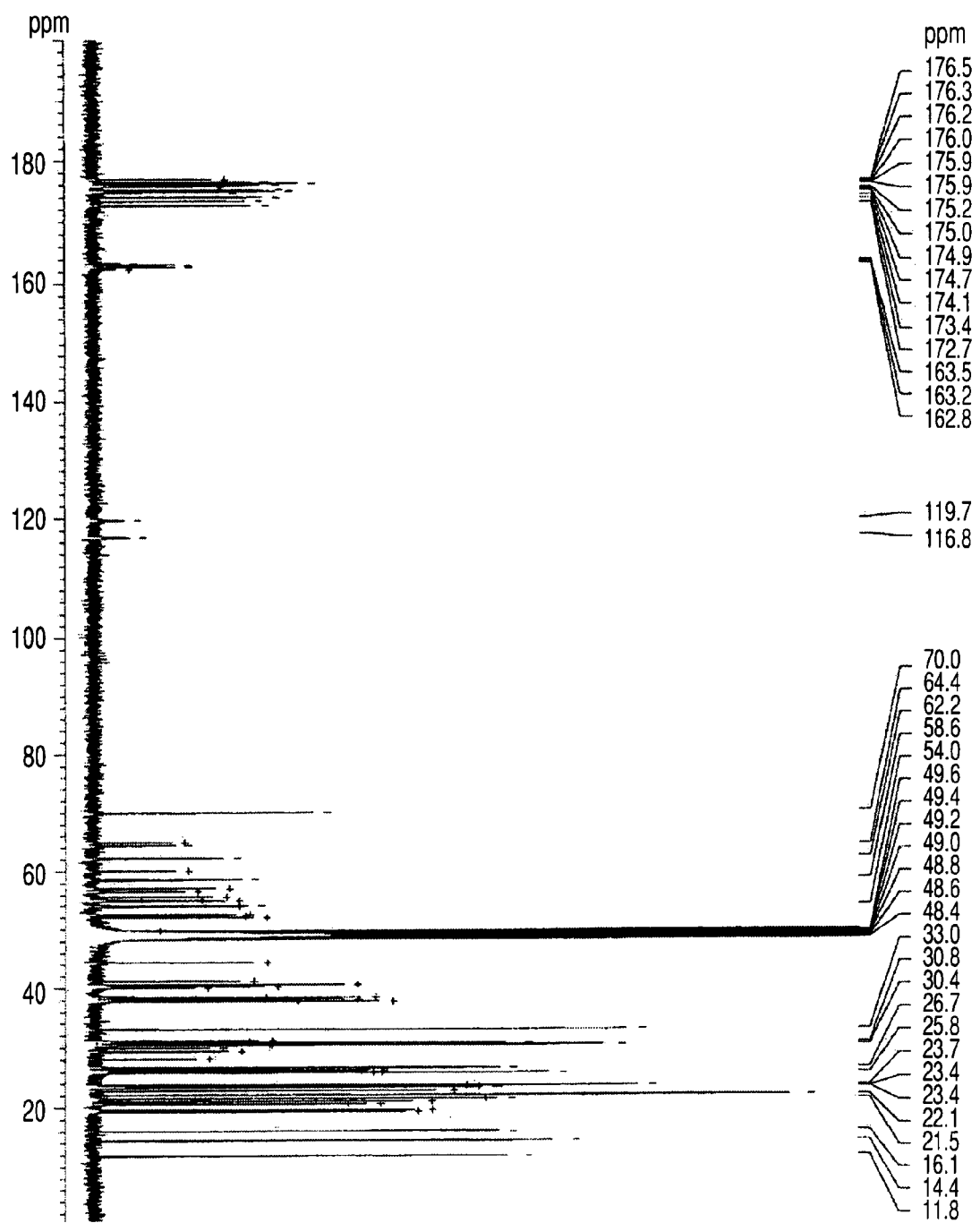
FIG. 14 is a chart of carbon-13 NMR spectrum.

FIGS. 13 and 14 show the proton and carbon-13 NMR spectra respectively, and the result of the ESI-MS spectrometric analysis is shown in FIG. 15.

Measurement Example 127

Figure 16:
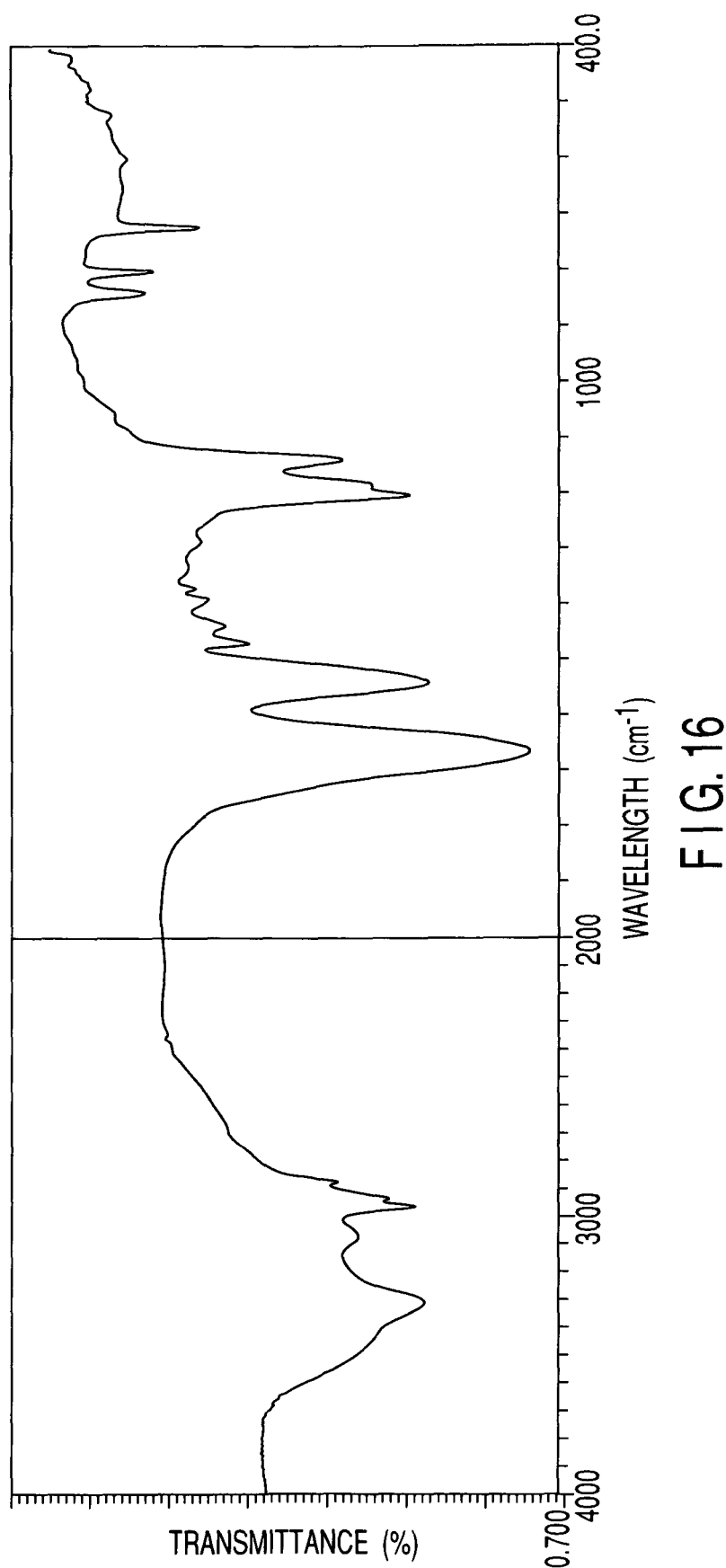
FIG. 16 is an infrared absorption spectrogram.

An infrared absorption spectrum of the present peptide BTI-baseMA026 is shown in FIG. 16.

Measurement Example 128

The specific rotation of the present peptide BTI-baseMA026 was determined to be $[\alpha]_D^{24}=-6.7°$ (c1.0, MeOH).

Measurement Example 129

The decomposition point of the present peptide BTI-baseMA026 (amorphous state) was determined to be 164° C.

In consideration of the results in Measurement Examples 112 to 117 above, it is estimated that the amino acid sequence and planar structure of the present peptide MA026 are those in the structural formula (I) above.

In additional consideration of the results in Measurement Examples 118 to 121 and 124 to 126 above, it is estimated that the amino acid sequences and planar structures of the present peptides BTI-MA026 and BTI-base MA026 are those shown in the structural formulae (II) and (III) above, respectively.

Measurement Example 201

Figure 17:
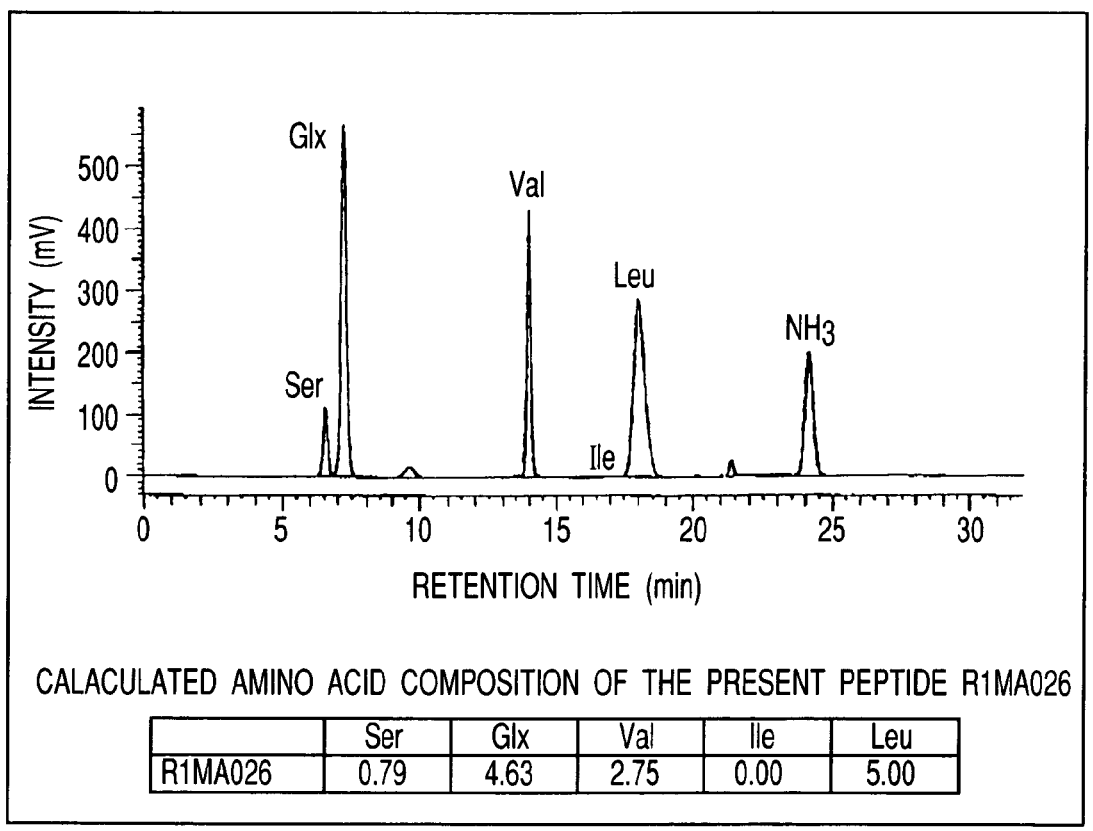
FIG. 17 is an amino acid analysis chart.

The present peptide R1MA026 obtained by purifying the fraction of peak No. 1 in Example 2 was analyzed for its amino acids in the same manner as in Measurement Example 110 above, and the results shown in FIG. 17 were obtained.

Measurement Examples 202 to 205

Figure 18:
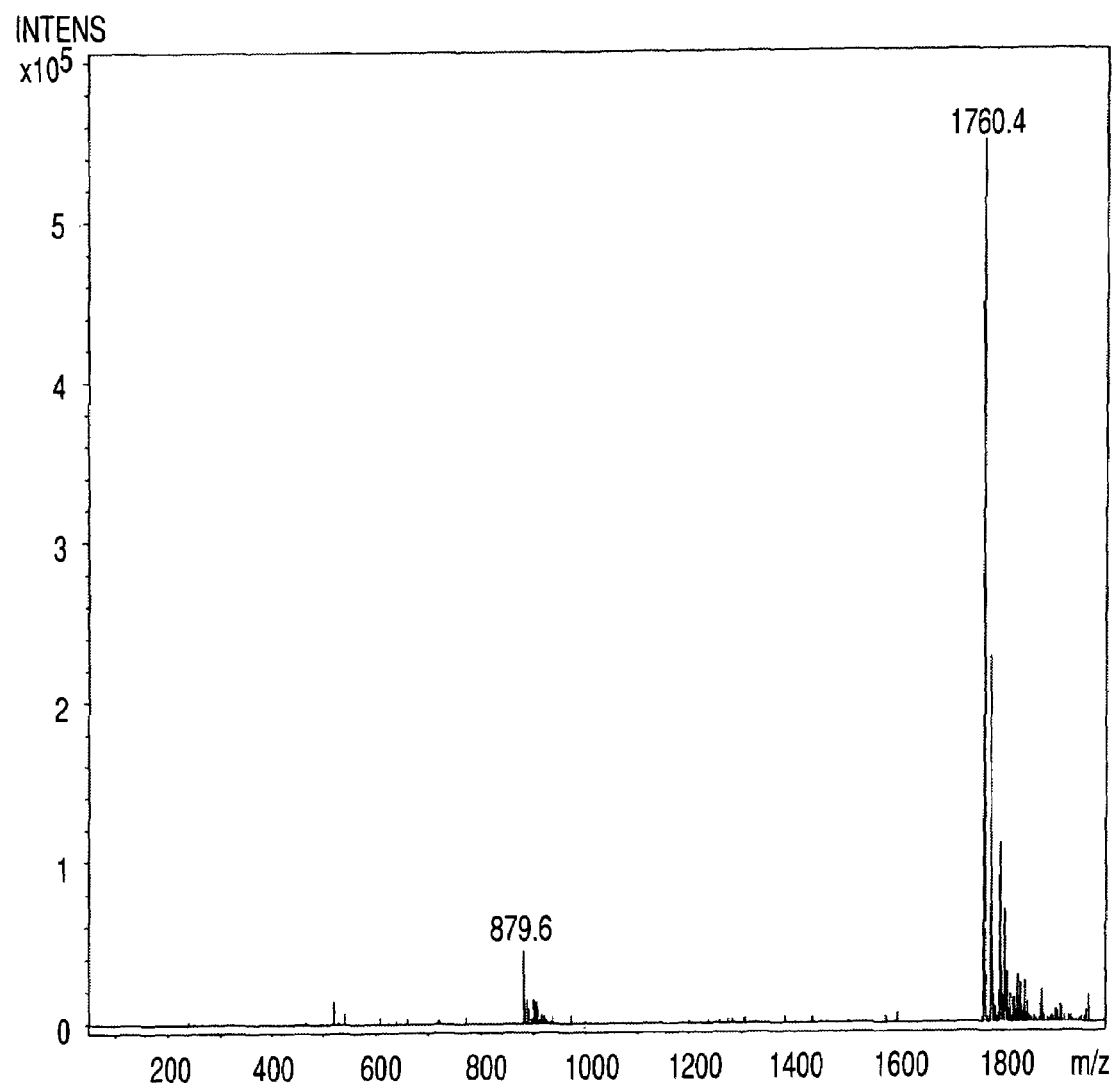
FIG. 18 is a negative ESI-MS spectrogram.
Figure 19:
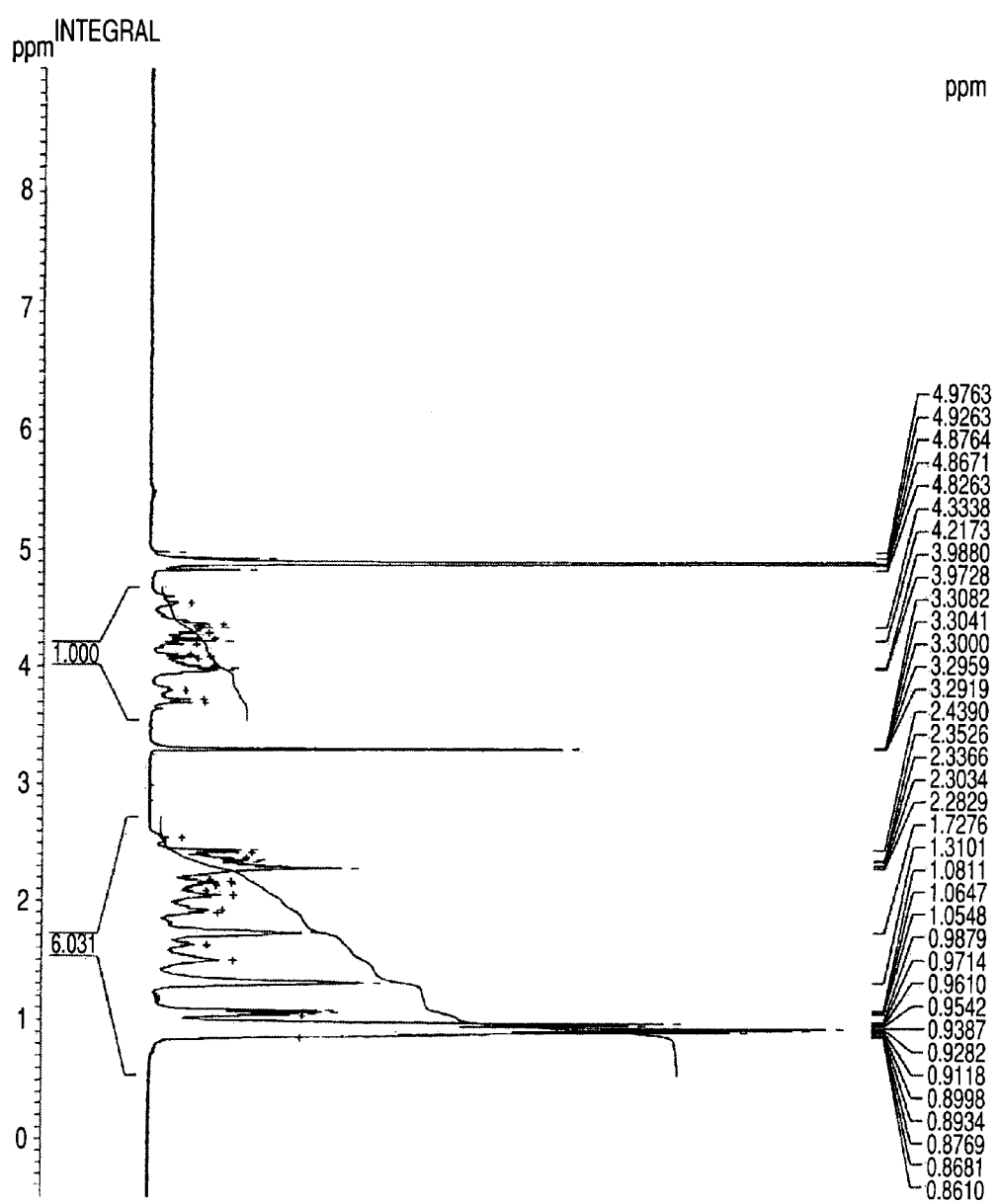
FIG. 19 is a chart of proton NMR spectrum.
Figure 20:
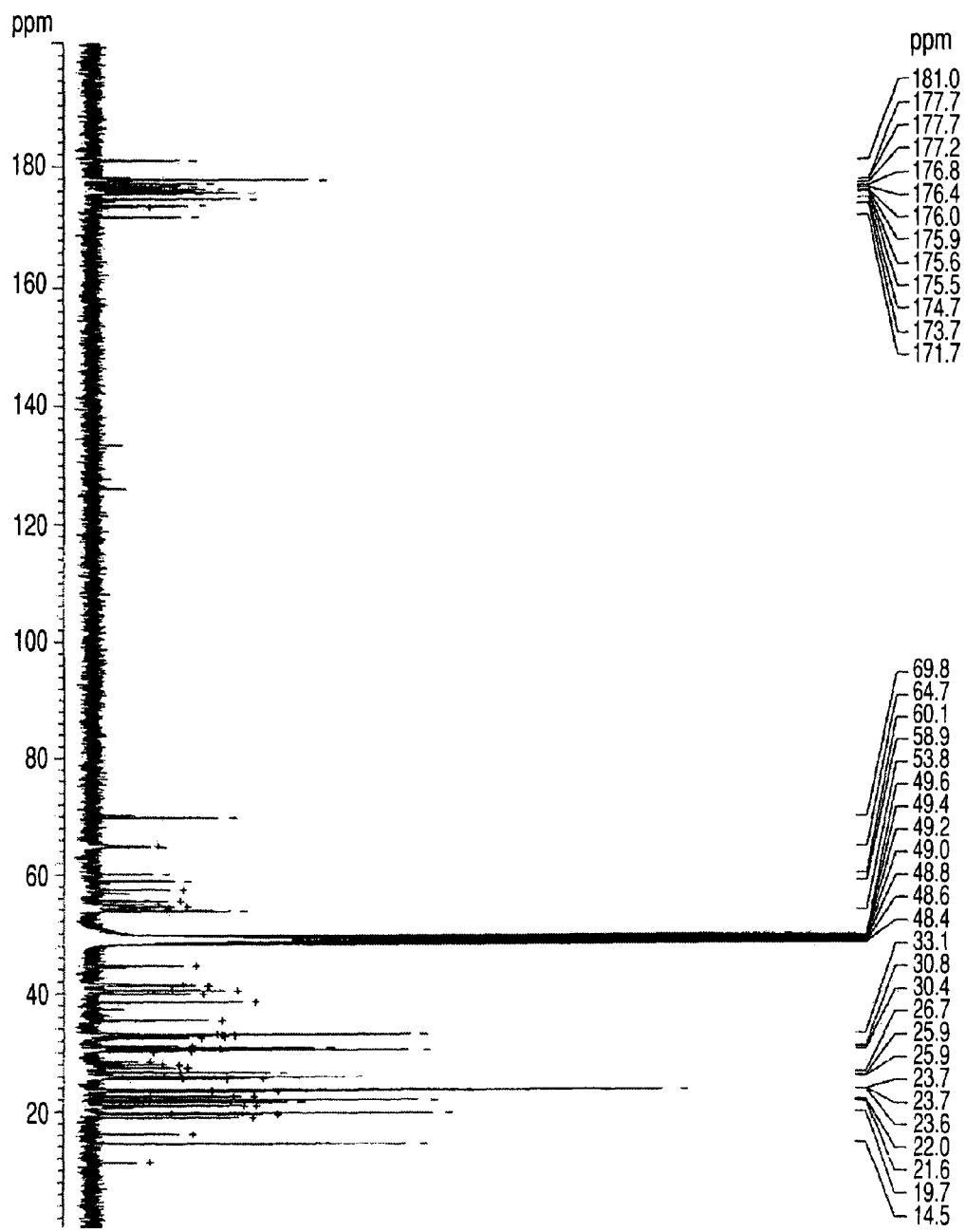
FIG. 20 is a chart of carbon-13 NMR spectrum.

The negative ESI-MS spectrometric analysis of the present peptide R1MA026 and the analysis of proton and carbon-13 NMR spectra thereof in methanol-$d_4$ were conducted, whereby the results shown in FIGS. 18 to 20 were obtained, respectively.

Measurement Example 206

Figure 21:
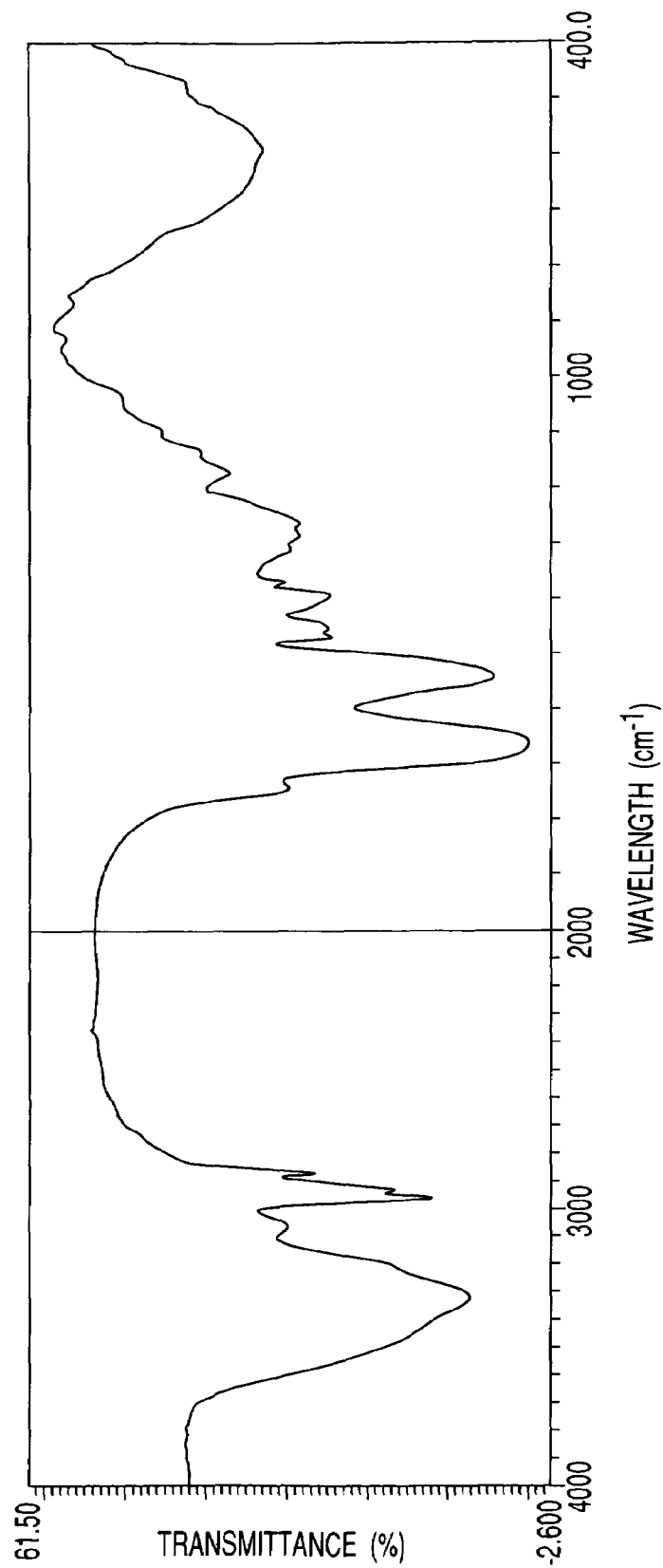
FIG. 21 is an infrared absorption spectrogram.

An infrared absorption spectrum of the present peptide R1MA026 is shown in FIG. 21.

Measurement Example 207

The specific rotation of the present peptide R1MA026 was determined to be $[\alpha]_D^{24}=-25.2°$ (c1.0, MeOH).

Measurement Example 208

The decomposition point of the present peptide R1MA026 (amorphous state) was determined to be 171° C.

Measurement Example 209

The present peptide R1MA026 was subjected to a Hofmann rearrangement in the same manner as in Example 3, and the resultant product was purified by high performance liquid chromatography under the following conditions.

Purification by High Performance Liquid Chromatography

Separation was conducted by high performance liquid chromatography (HPLC) equipped with an ODS column, YMC-Pack R&D ODS (20×250 mm). This separation was conducted under the conditions where the flow rate was 5.0 mL/min., the detection wavelength was 220 nm, and the elution solvent was a linear gradient of from 30% aqueous acetonitrile plus 0.1% trifluoroacetic acid (TFA) to 100% acetonitrile plus 0.1% TFA, to complete purification.

The obtained BTI-R1MA026 was analyzed for its amino acids, and the results shown in Table 9 were obtained.

TABLE 9

|  | Ser | Glx | Val | Ile | Leu |
|---|---|---|---|---|---|
| Before reaction | 0.79 | 4.63 | 2.75 | 0.00 | 5.00 |
| After reaction | 1.16 | 0.91 | 4.69 | 0.00 | 5.00 |

Measurement Example 210

The ESI-MS spectrometric analysis of the present peptide BTI-R1MA026 was conducted, and the result shown in FIG. 22 was obtained.

From these results, it was estimated that the ratio of glutamine/glutamic acid contained in the constitutive amino acids in the present peptide R1MA026 is 4:1. Accordingly, it was estimated that the constitutive amino acids in R1MA026 consist of 4 glutamine residues, 1 glutamic acid, 1 serine residue, 3 valine residues and 5 leucine residues.

Measurement Examples 211 and 212

The present peptide R1MA026 was subjected to acid hydrolysis with 6 N HCl at 91° C. for 18 in accordance with the method of Measurement Examples 115 and 116, and the resultant acid hydrolyzates were extracted with diethyl ether. The extract was methylated with diazomethane in the same manner as in Measurement Example 114. Then, the desired fraction was obtained by purification with silica gel chromatography. The fraction shows an Rf value of 0.13 in thin layer chromatography {developing solvent: hexane/ethyl acetate=3:2}. Proton and carbon-13 NMR spectra of this collected sample were taken to give the similar results as those obtained in Measurement Example 115.

From these results, it is estimated that the N-terminal amino acid residue of the present peptide R1MA026 is leucine, and a 3-hydroxydecanoyl group is bonded, via an amide linkage, to this leucine.

Measurement Example 213

The present peptide R1MA026 was subjected to a reaction with $CrO_3$ in the same manner as in Measurement Example 113, (1), and the amino acid of the thus obtained product was analyzed. Separately, the present peptide R1MA026 was reacted with dimethylamine, then with $CrO_3$ in the same manner as Measurement Example 113, (2), to analyze amino acids.

The respective calculated amino acid compositions are shown in Table 10 below.

TABLE 10

|  | Ser | Glx | Val | Ile | Leu |
|---|---|---|---|---|---|
| Before reactions of (1) and (2) | 0.79 | 4.63 | 2.75 | 0.00 | 5.00 |
| After reaction of (1) | 0.75 | 4.33 | 2.42 | 0.00 | 5.00 |
| After reaction of (2) | 0.00 | 4.55 | 2.50 | 0.00 | 5.00 |

From the results shown in Table 10 above, it is estimated that the amino acid residue at the hydroxy side of the ester linkage forming the cyclic structure of the present peptide R1MA026 is serine.

Measurement Example 214

Figure 23:
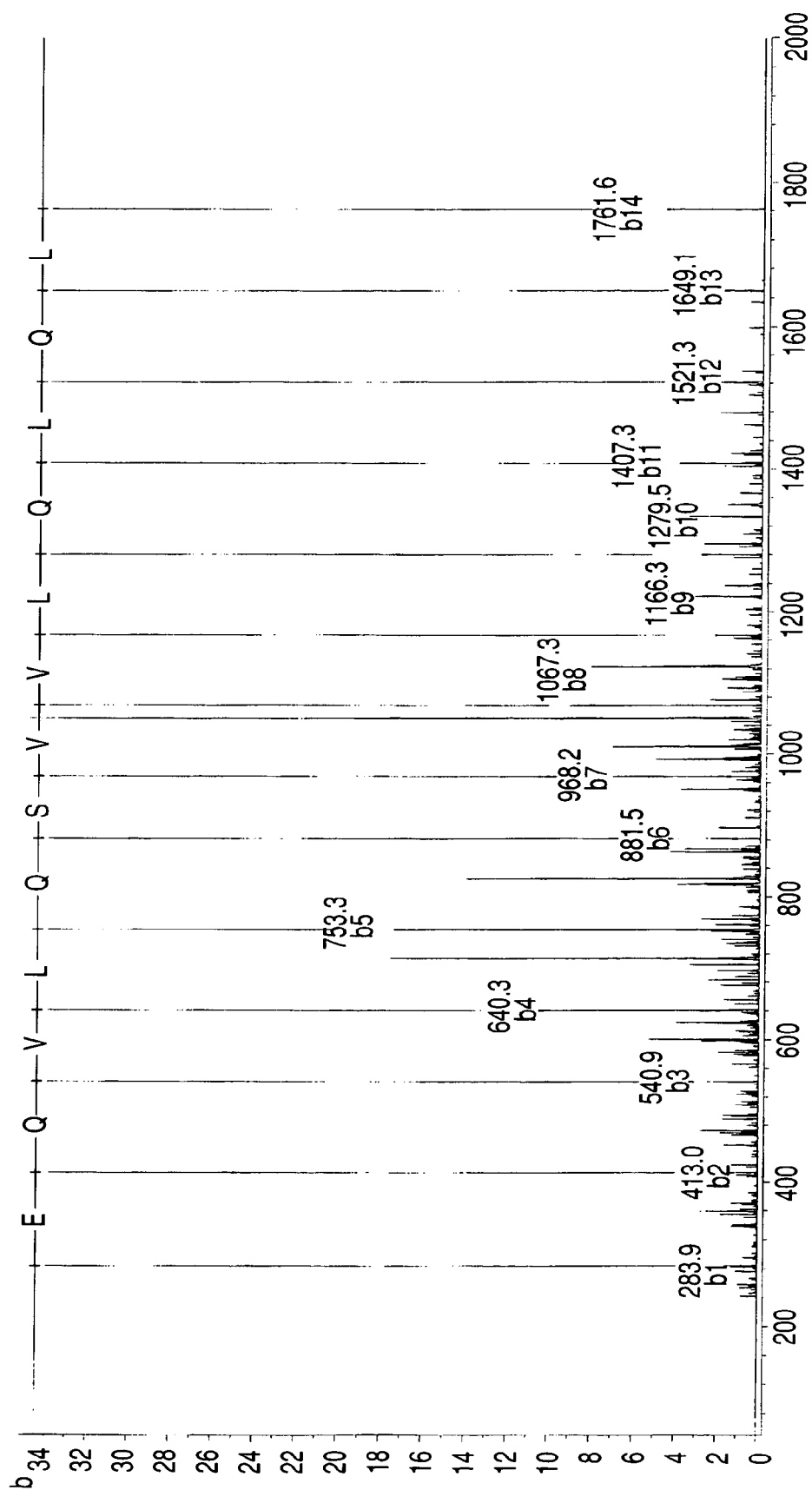
FIG. 23 is a positive ESI MS/MS spectrogram.

An ESI-MS/MS spectrum of the present peptide R1MA026 is shown in FIG. 23.

In consideration of the results in Measurement Examples 211 to 214 above, it is estimated that the amino acid sequence and planar structure of the present peptide R1MA026 are those in the structural formula (IV) below:

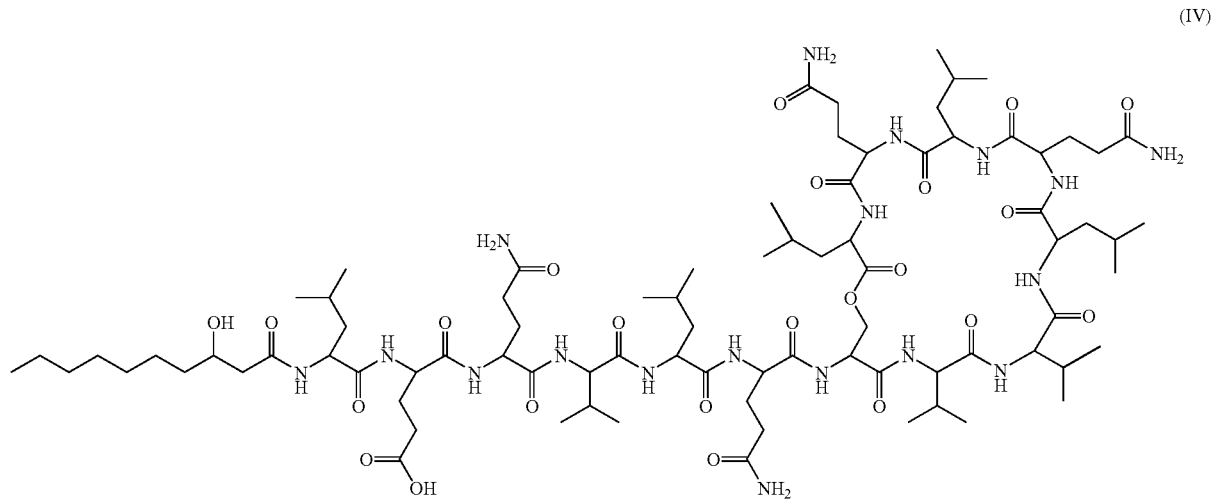

Measurement Example 301

The present peptide R2MA026 obtained by purifying the fraction of peak No. 3 in Example 2 was subjected to amino acid analysis in the same manner as in Measurement Example 110 above, and the result shown in FIG. 24 was obtained.

Measurement Examples 302 to 305

Figure 25:
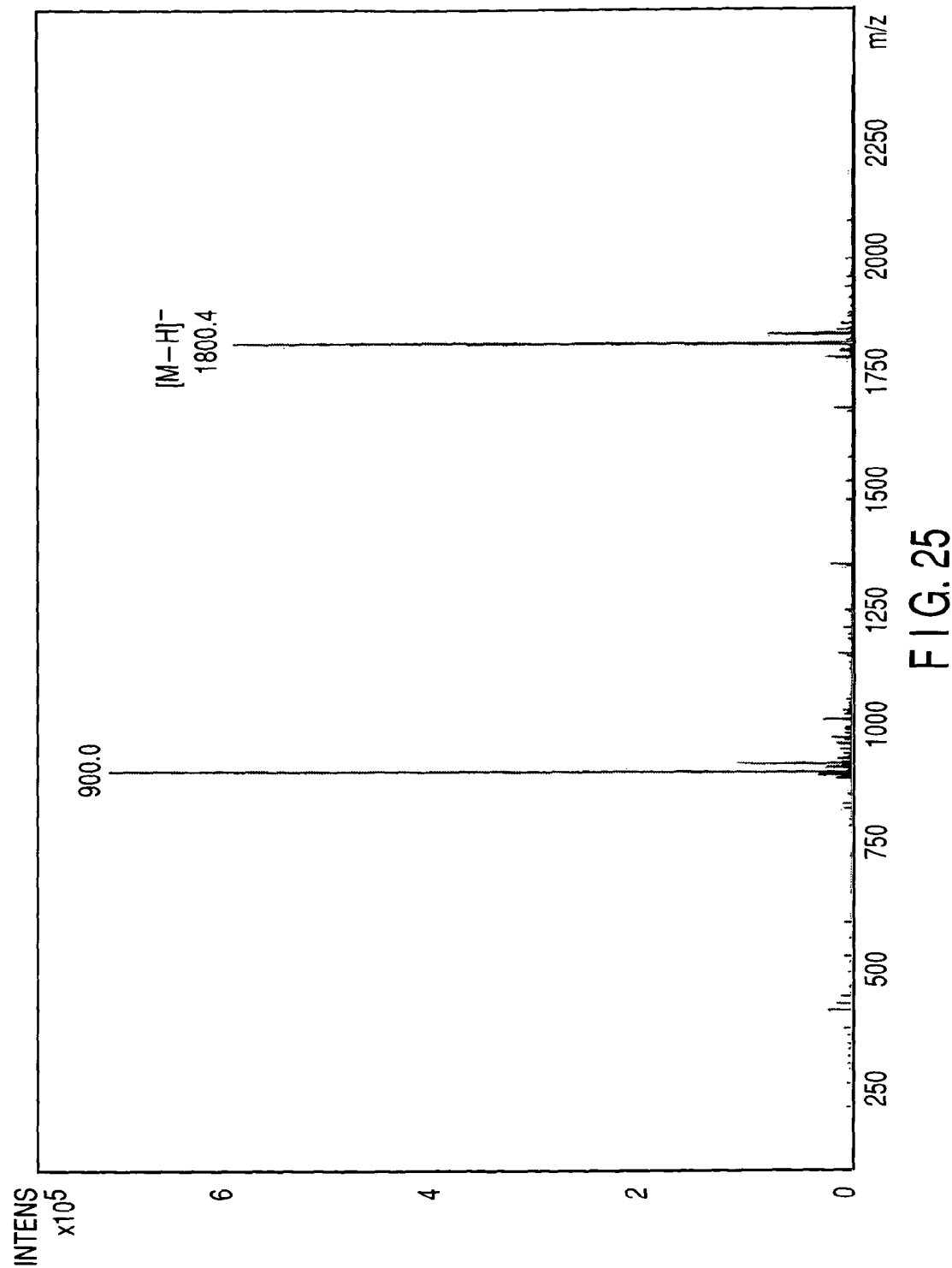
FIG. 25 is a negative ESI-MS spectrogram.
Figure 26:
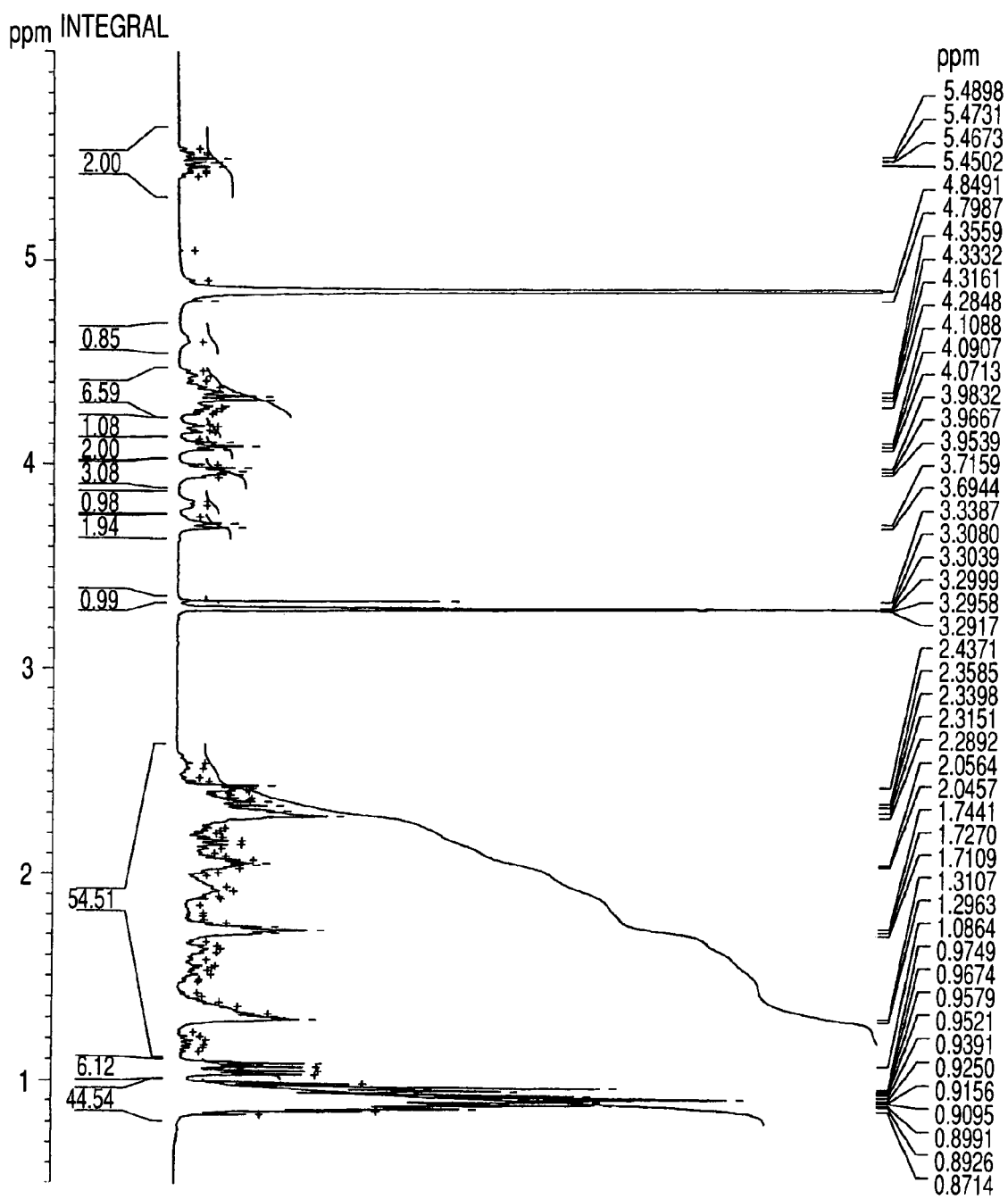
FIG. 26 is a chart of proton NMR spectrum.
Figure 27:
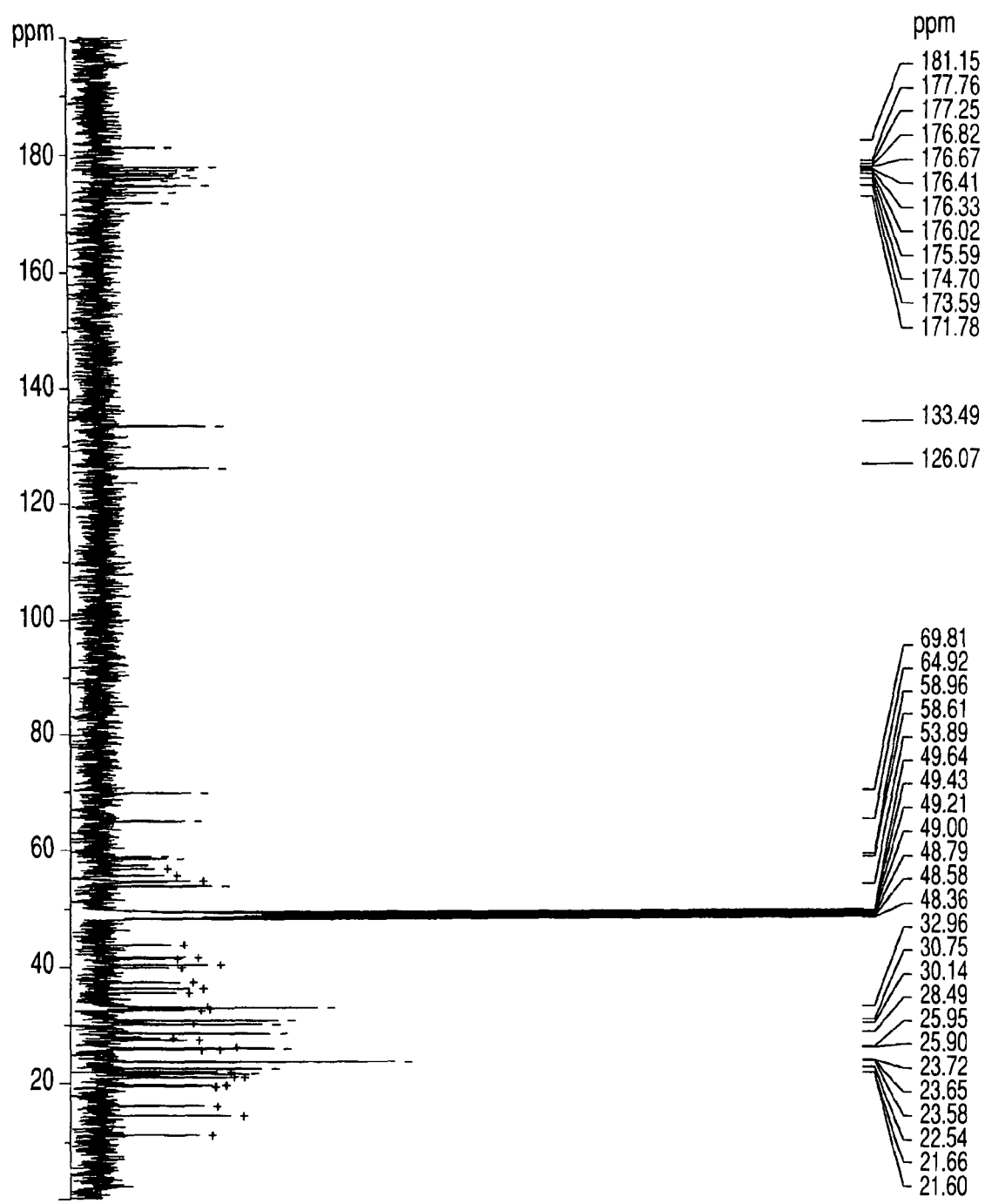
FIG. 27 is a chart of carbon-13 NMR spectrum.

The negative ESI-MS spectrometric analysis of the present peptide R2MA026 and the analysis of proton and carbon-13 NMR spectra thereof in methanol-$d_4$ were conducted, whereby the results shown in FIGS. 25 to 27 were obtained respectively.

Measurement Example 306

Figure 28:
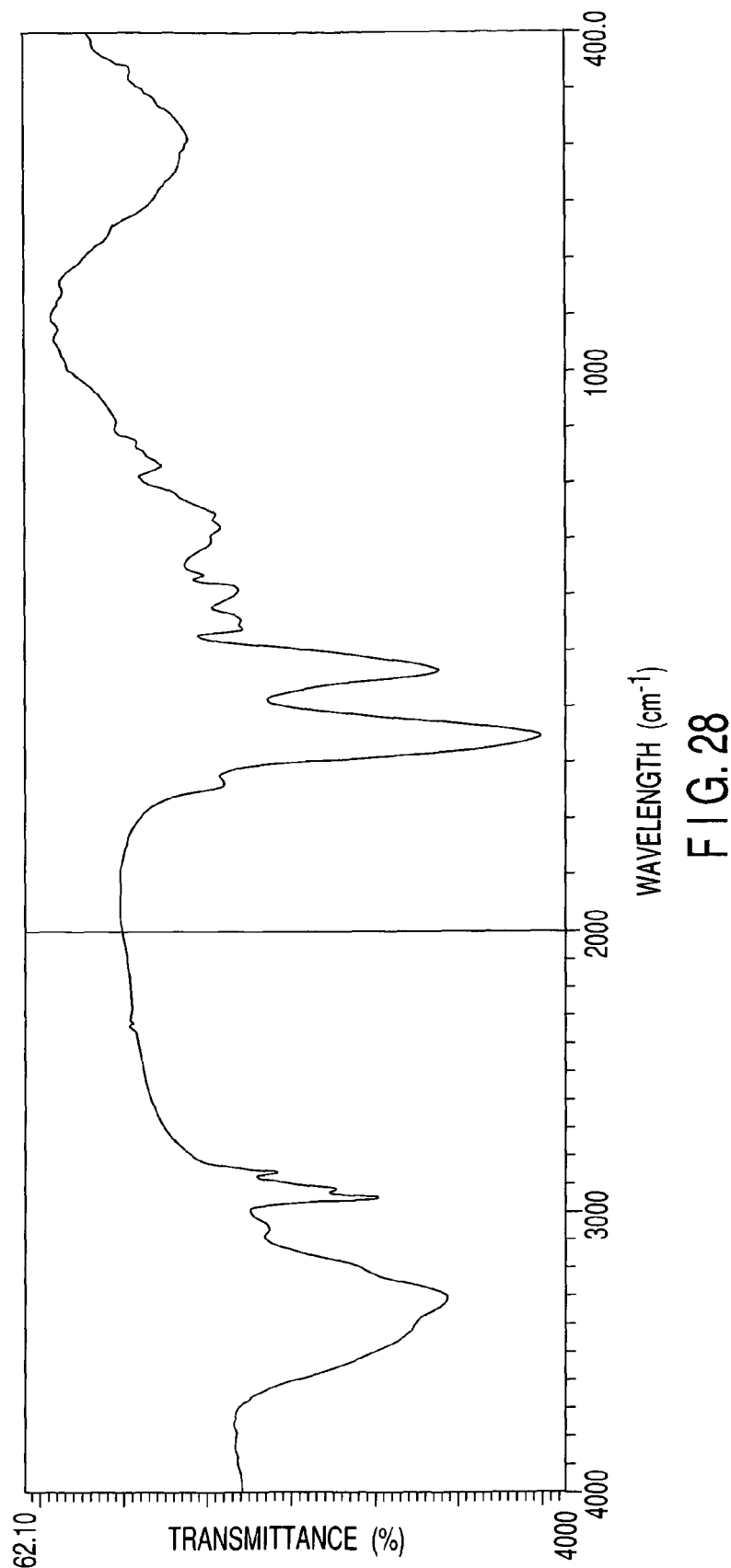
FIG. 28 is an infrared absorption spectrogram.

An infrared absorption spectrum of the present peptide R2MA026 is shown in FIG. 28.

Measurement Example 307

The specific rotation of the present peptide R2MA026 was determined to be $[\alpha]_D^{24}=-23.5°$ (c1.0, MeOH).

Measurement Example 308

The decomposition point of the present peptide R2MA026 (amorphous state) was determined to be 166° C.

Measurement Example 309

The present peptide R2MA026 was subjected to Hofmann rearrangement and purified by high performance liquid chromatography in the same manner as in Measurement Example 209, and the resulting BTI-R2MA026 was subjected to amino acid analysis and the result shown in Table 11 was obtained.

TABLE 11

|  | Ser | Glx | Val | Ile | Leu |
|---|---|---|---|---|---|
| Before reaction | 0.80 | 4.66 | 1.95 | 0.92 | 5.00 |
| After reaction | 0.84 | 1.08 | 1.93 | 0.95 | 5.00 |

Measurement Example 310

Figure 29:
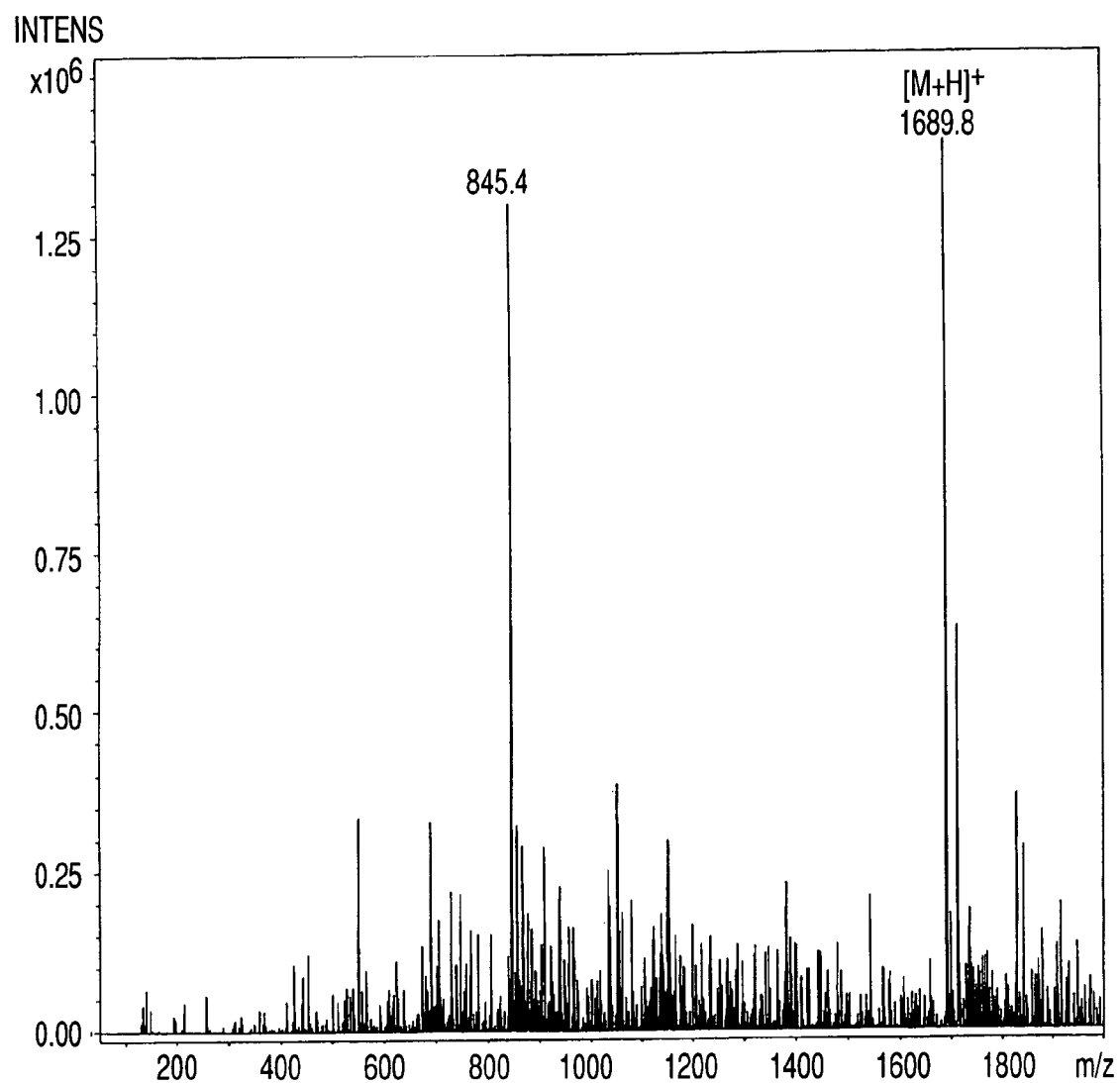
FIG. 29 is an ESI-MS spectrogram chart.

The present peptide BTI-R2MA026 was subjected to ESI-MS spectrometric analysis, and the result shown in FIG. 29 was obtained.

From these results, it was estimated that the ratio of glutamine/glutamic acid contained in the constitutive amino acids in the present peptide R2MA026 is 4:1. Accordingly, it was estimated that the constitutive amino acids in R2MA026 consist of 4 glutamine residues, 1 glutamic acid residue, 1 serine residue, 2 valine residues, 1 isoleucine residue and 5 leucine residues.

Measurement Examples 311 and 312

The present peptide R2MA026 was subjected to acid hydrolysis with 6 N HCl at 90° C. for 14 hours in accordance with the method of Measurement Examples 115 and 116, and the resultant acid hydrolyzates were extracted with diethyl ether. The extract was methylated with diazomethane in the same manner as in Measurement Example 114. Then, the desired fraction was obtained by purification with silica gel chromatography. The fraction shows an Rf value of 0.18 in thin layer chromatography {developing solvent: hexane/ethyl acetate=3:2}. Proton NMR spectra of this collected sample were taken to give the following results.

$^1$H NMR (400 MHz, CDCl$_3$+TMS, Δppm) 0.88 (3H, t, J=6.9, H12), 0.94 (6H, d, J=6.4, H5'&H6'), 1.28 (8H, br, H8&H9&H10&H11), 1.52-1.67 (3H, m, H3'a & H3"b&H4'), 2.04 (2H, m, H7), 2.29 (1H, m, H4b), 2.33 (1H, dd, J=15.3&8.9, H2b), 2.34 (1H, m, H4a), 2.46 (1H, dd, J=15.4&2.8, H2a), 3.35 (1H, d, J=3.0, OH), 3.74 (3H, s, Me), 4.02 (1H, m, H3), 4.65 (1H, td, J=8.6&4.8, H2'), 5.38 (1H, app.dd, J=18.2&7.5, H5), 5.57 (1H, app.dd, J=18.1&7.3, H6), 6.22 (1H, d, J=8.0, NH)

From these data, structure of the hydrolysis product was estimated to be the structural formula (XII) below:

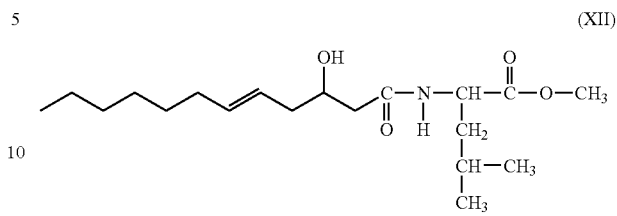

(XII)

From these results, it is estimated that the N-terminal amino acid residue of the present peptide R2MA026 is leucine, and a 3-hydroxydodec-5-enoyl group is bonded, via an amide linkage, to this leucine.

Measurement Example 313

The present peptide R2MA026 and lithium borohydride (LiBH$_4$) were reacted in the same manner as in Measurement Example 112, and analyzed by an amino acid analyzer.

The calculated amino acid compositions are shown in Table 12 below:

TABLE 12

|  | Ser | Glx | Val | Ile | Leu |
|---|---|---|---|---|---|
| Before reaction | 0.80 | 4.66 | 1.95 | 0.92 | 5.00 |
| After reaction | 0.77 | 4.78 | 1.85 | 0.63 | 5.00 |

From the results shown in Table 12 above, it is estimated that the amino acid residue at the carboxy side of the ester linkage forming the cyclic structure of the present peptide R2MA026 is isoleucine.

Measurement Example 314

The present peptide R2MA026 was subjected to a reaction with CrO$_3$ in the same manner as in Measurement Example 113, (1), and the amino acid of the thus obtained product was analyzed. Separately, the present peptide R2MA026 was reacted with dimethylamine, then with CrO$_3$ in the same manner as Measurement Example 113, (2), to analyze amino acids.

The respective calculated amino acid compositions are shown in Table 13 below:

TABLE 13

|  | Ser | Glx | Val | Ile | Leu |
|---|---|---|---|---|---|
| Before reactions of (1) and (2) | 0.80 | 4.66 | 1.95 | 0.92 | 5.00 |
| After reaction of (1) | 0.73 | 3.47 | 1.87 | 0.84 | 5.00 |
| After reaction of (2) | 0.00 | 4.42 | 1.95 | 0.87 | 5.00 |

From the results shown in Table 13 above, it is estimated that the amino acid residue at the hydroxy side of the ester linkage forming the cyclic structure of the present peptide R2MA026 is serine.

Measurement Example 315

Figure 30:
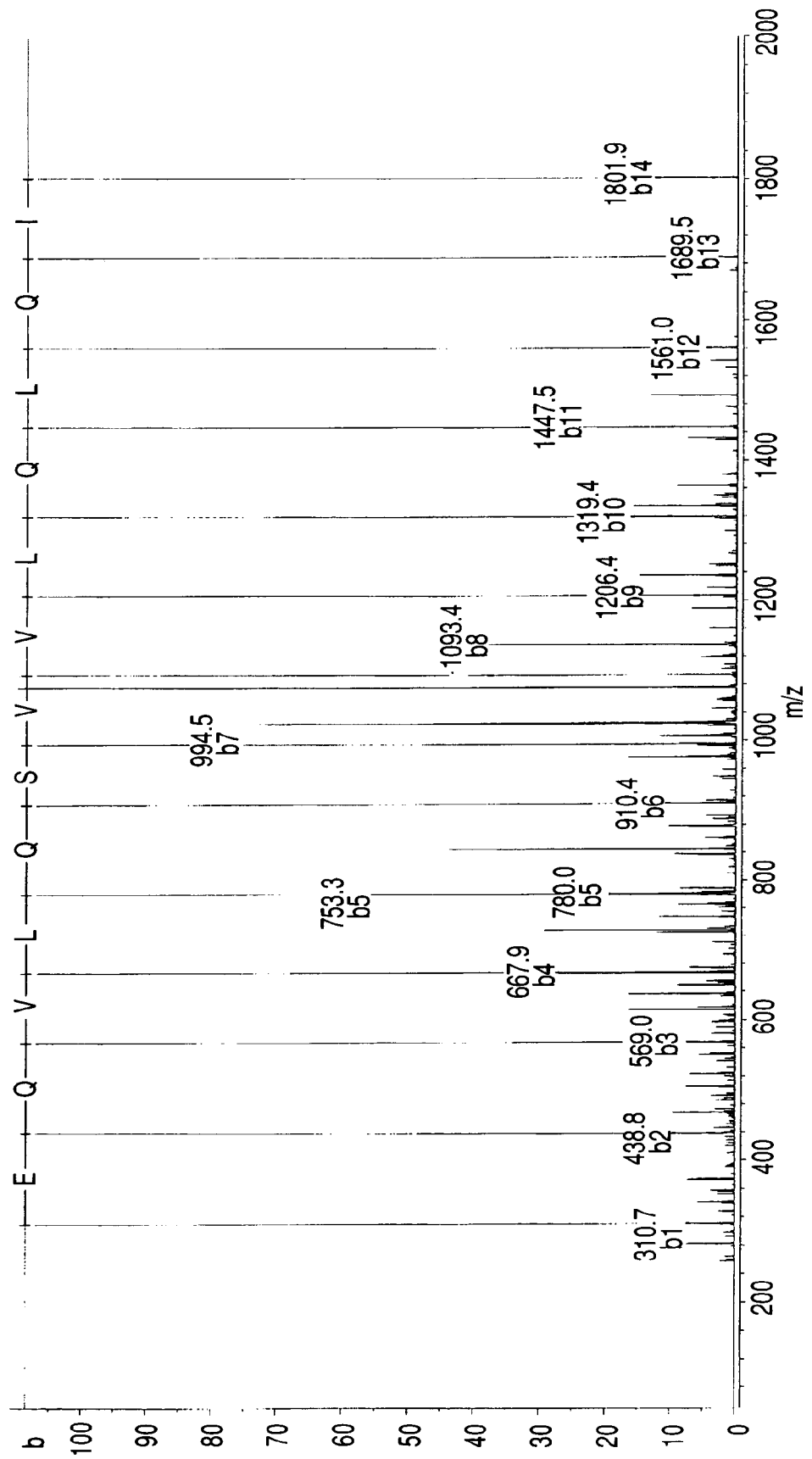
FIG. 30 is an ESI-MS/MS spectrogram.

An ESI-MS/MS spectrum of the present peptide R2MA026 is shown in FIG. 30.

In consideration of the results in Measurement Examples 311 to 315 above, it is estimated that the amino acid sequence and planar structure of the present peptide R2MA026 are those in the structural formula (V) below:

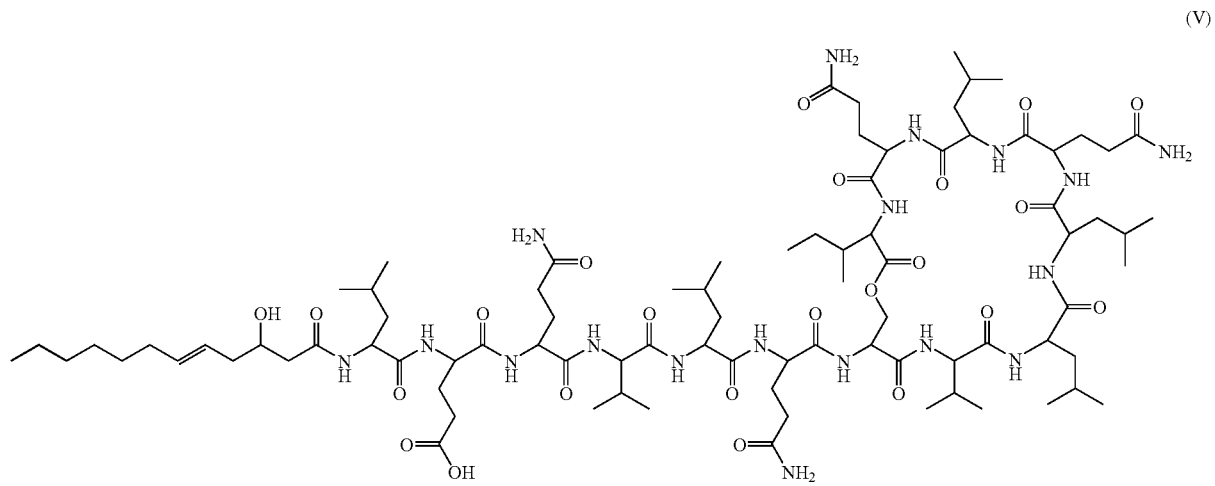

(V)

Measurement Examples 401 to 403

Regarding the purified product obtained in Example 5 (the present peptide AL-MA026), a proton NMR spectrum was taken, and its FAB-MS spectrometric analysis was conducted.

Figure 31:
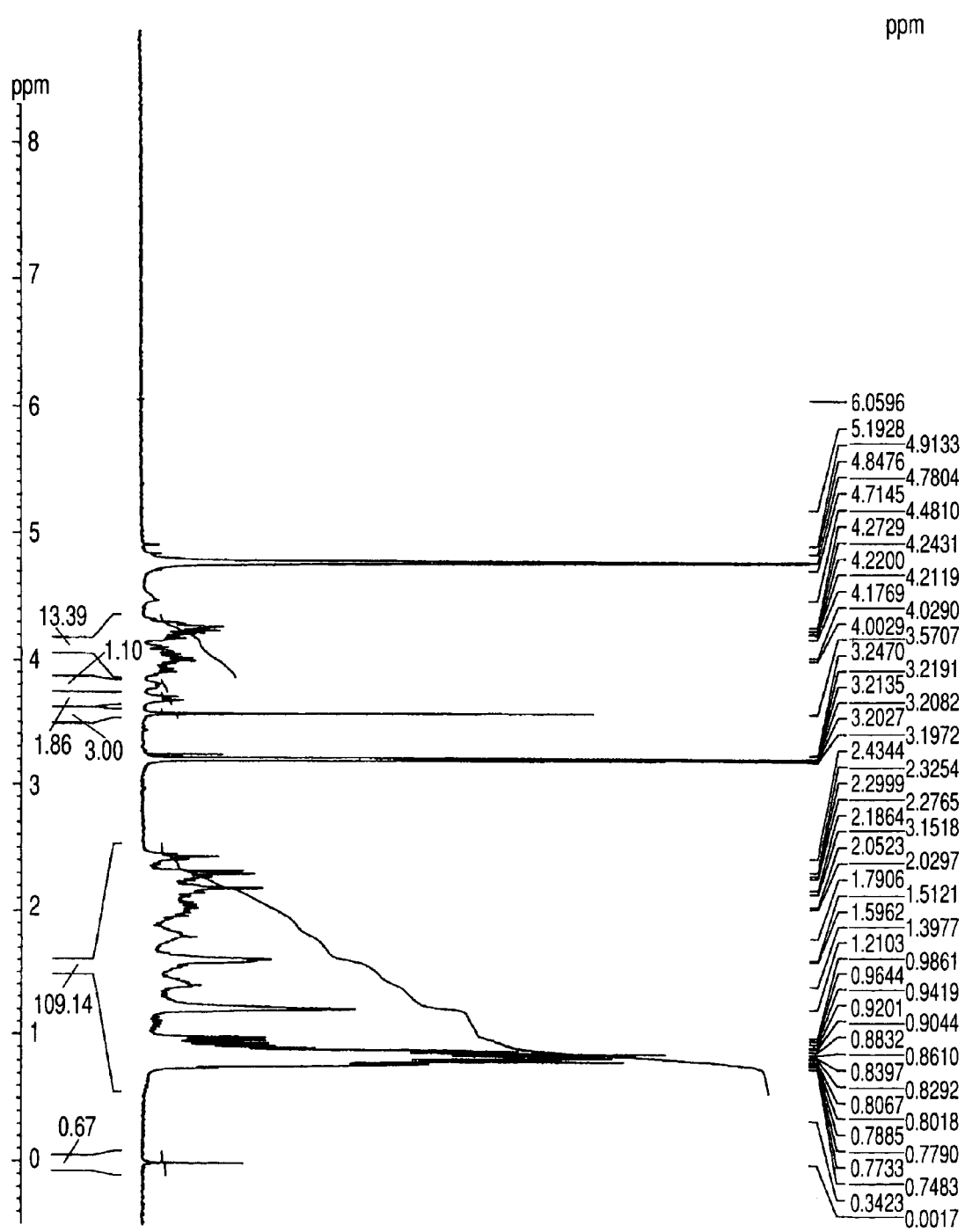
FIG. 31 is a chart of proton NMR spectrum.
Figure 32:
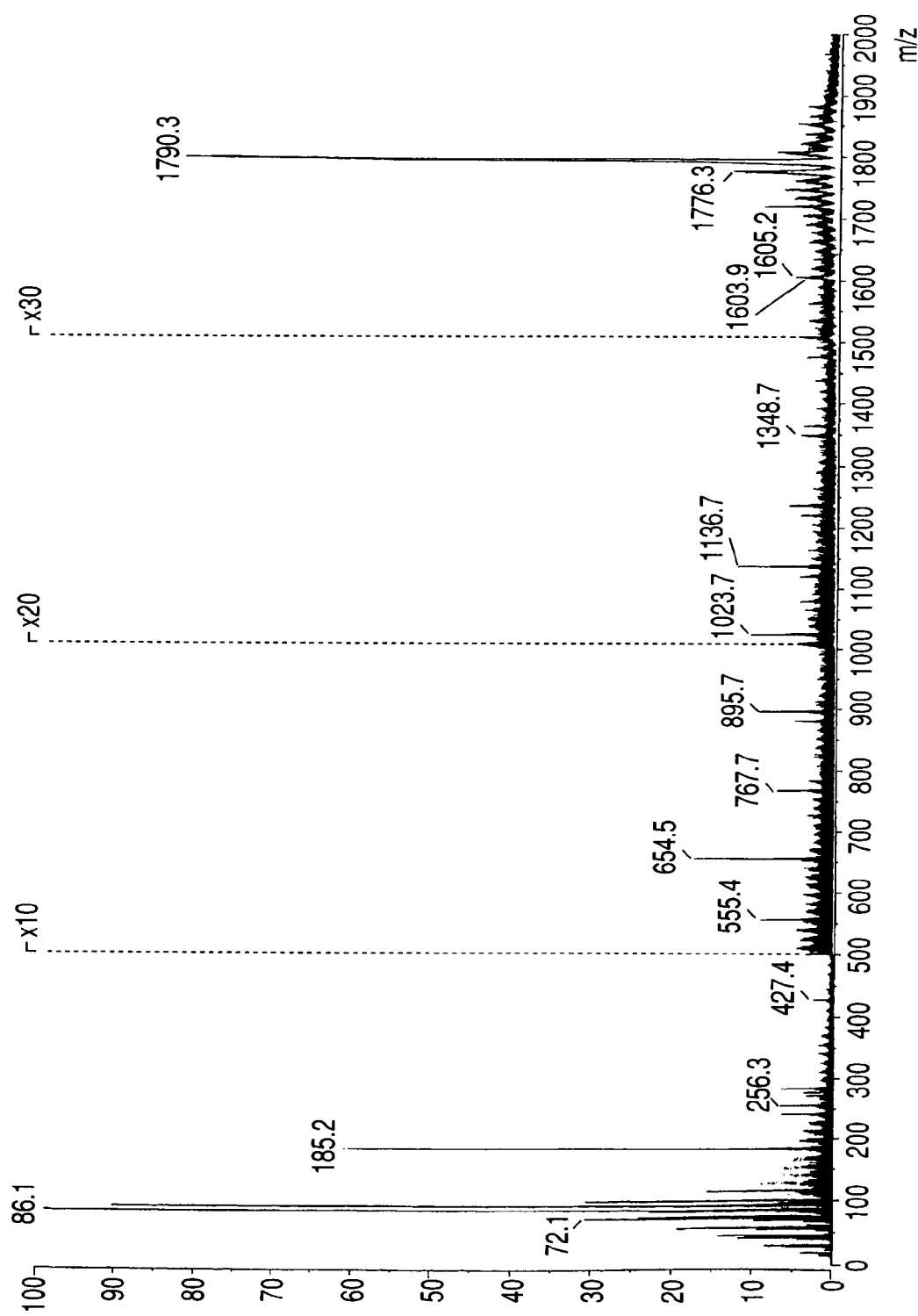
FIG. 32 is a positive FAB-MS spectrogram.
Figure 33:
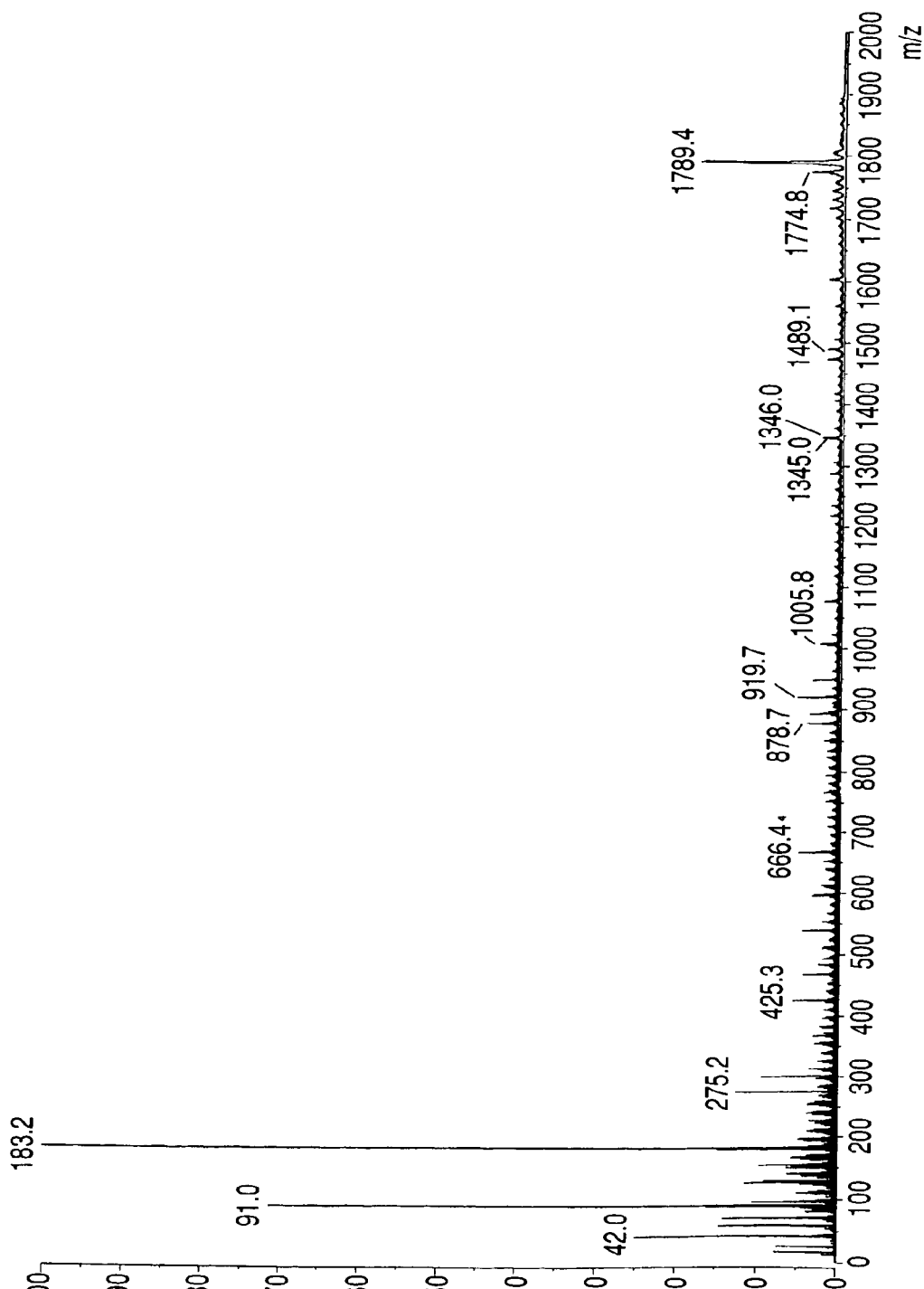
FIG. 33 is a negative FAB-MS spectrogram.

FIG. 31 shows the proton NMR chart, FIG. 32 shows the positive FAB-MS chart, and FIG. 33 shows the negative FAB-MS chart.

Example 6

<Administration Test 1 of the RtIB026 Strain of the Invention>

The present RtIB026 strain obtained in Example 1 was mixed with rainbow trout feed and orally administered, whereby the resistance to infectious hematopoietic necrosis virus (IHNV) of salmonid was evaluated and the effect of the present strain on prevention of infection of farmed fish with the pathogenic virus was examined. The test was conducted in a plastic water tank (10 L) in a room.

Sixty laeval fish (weight 1 g; length 3 cm) one month after hatch were divided at random into two groups, each consisting of 30 fish, and raised at 10° C., where the administration group was given feed containing $10^7$ CFU RtIB026 strain/1 g feed while the control group was given conventional feed once per day for 2 weeks. After the administration was finished, the fish were infected with the virus by placing them for 1 hour in 100 PFU/mL IHNV solution, and both the groups were raised with conventional feed, and the progress thereafter was observed.

The results are shown in FIG. 34. As can be seen from FIG. 34, no decrease in the survival rate in both the administration and control groups was recognized until Day 4 after infection with IHNV. On and after Day 5, the survival rate of the control group dropped below that of the administration group, and on and after Day 9, the difference in the survival rate therebetween was increased, and 23 days after infection with the virus, the survival rate of the control group was 20%, while about 70% of the administration group survived, thus indicating significant prevention of occurrence of the viral disease.

Reference Example 1

The present RtIB026 strain obtained in Example 1 above was inactivated by treatment with formalin, collected by centrifugation, washed with. physiological saline, and added to feed. Then, the administration test of the inactivated RtIB026 strain was conducted in the same manner as in Administration Test 1 in Example 6.

As a result, on Day 23 after IHNV infection, the survival rate of administering the inactivated cells was 16.7%, so the effect of preventing IHNV infection was not recognized.

Example 7

<Measurement of Antiviral Activities of the Present Peptide MA026 in Fish etc.>

The antiviral activities of the present peptide MA026 against infectious hematopoietic necrosis virus (IHNV) in salmonid, rhabdovirus (EVA) in American eels and rhabdovirus (EVEX) in European eels were measured according to the method described in Example 1.

Figure 35:
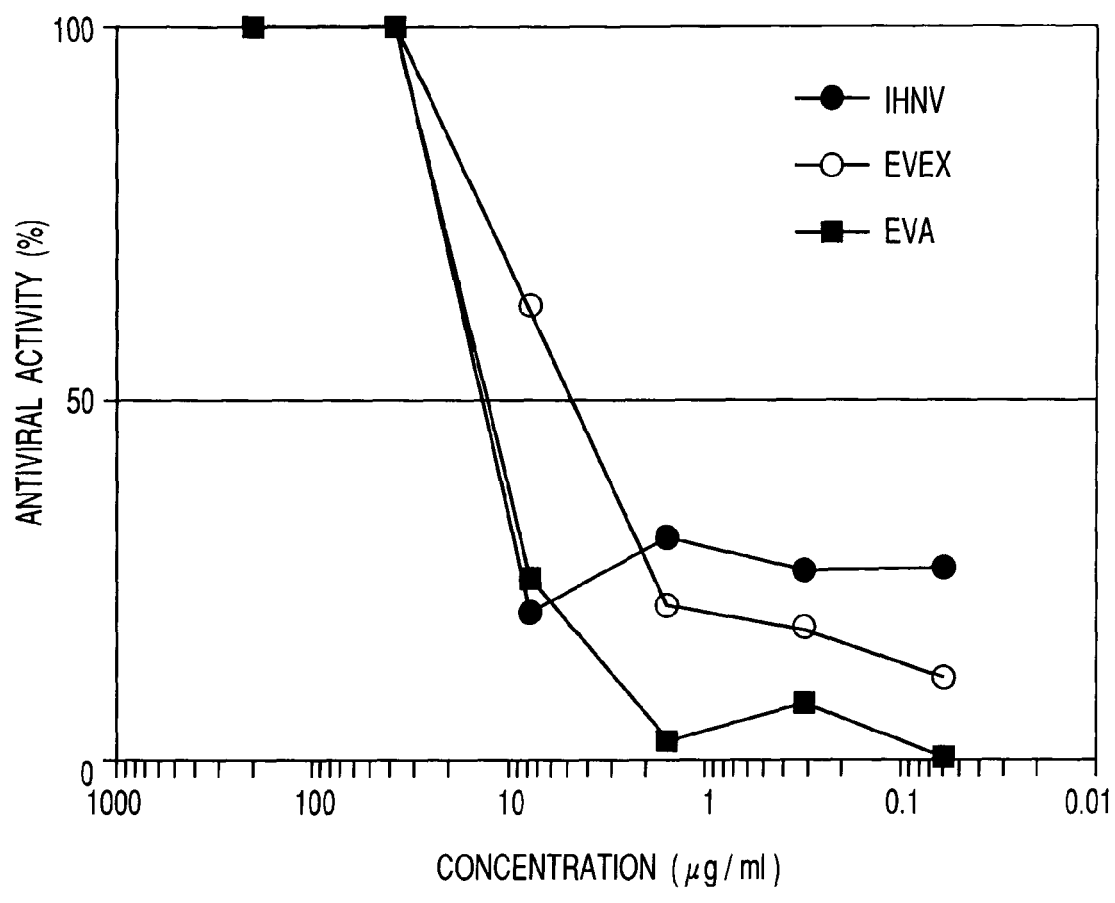
FIG. 35 is a graph showing the antiviral activities against IHNV, EVA and EVEX.

The results are shown in FIG. 35.

As can be seen from FIG. 35, the present peptide MA026 has a high antiviral activity against IHNV, EVA and EVEX.

Example 8

The antiviral activities of the present peptides R1MA026 and R2MA026 against IHNV were measured in the same manner as in Example 7, and their antiviral activities were confirmed.

The results are shown in FIG. 36.

Example 9

The antiviral activities of the present peptides AL-MA026, BTI-MA026 and BTI-base MA026 against IHNV were measured, and their antiviral activities were confirmed.

Figure 37:
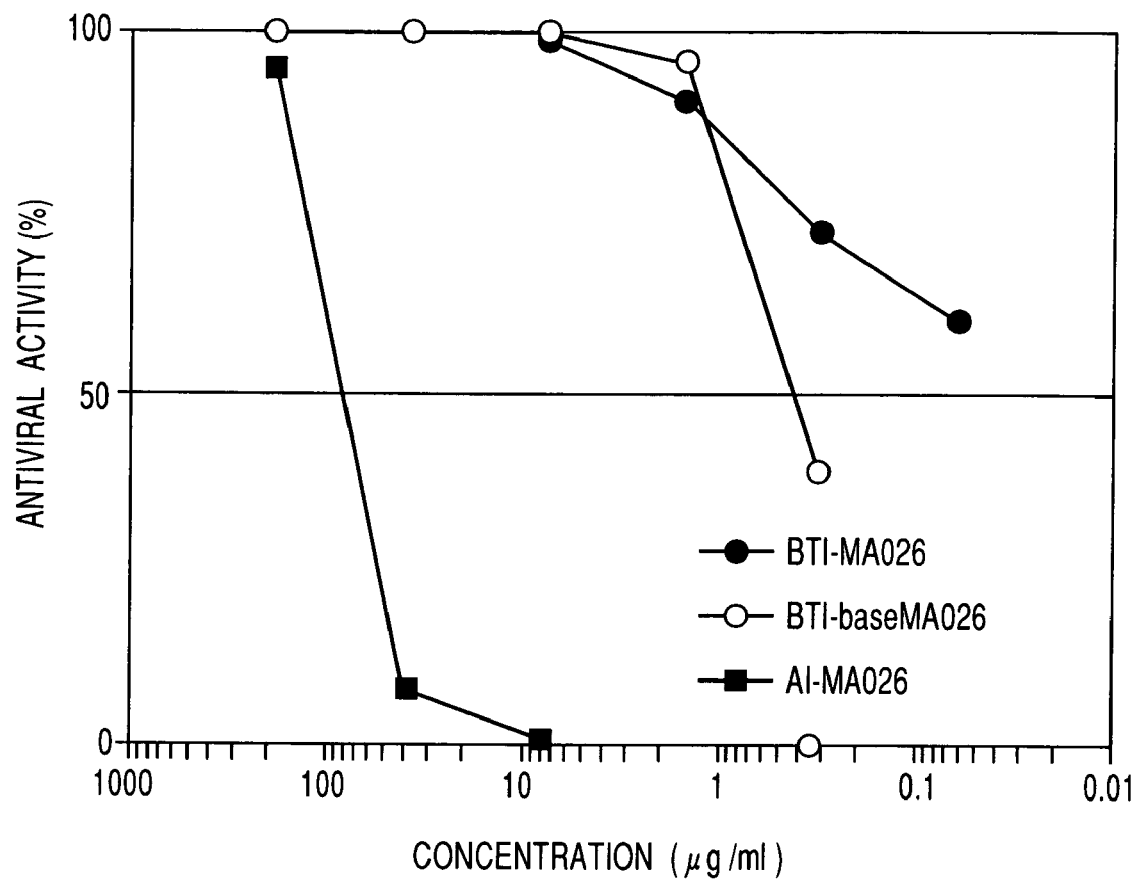
FIG. 37 is a graph showing the antiviral activity against IHNV.

The results are shown in FIG. 37.

Example 10

<Antiviral Activity of the Present Peptides Against Influenza Virus>

The method of evaluating the antiviral activity against influenza virus is shown below. The viral strains used in this test were domestic-animal hygiene strains supplied from the Japanese Association of Vetrinary Biologics. Viral strain VS0505 (A/New Jersey/8/76 strain) was used as the swine influenza virus, and VA0902 (A/turkey/Ontario/6118/68 strain) was used as the avian virus. It is expected that the present peptides having an antiviral activity against these influenza viruses derived from domestic animals have also an antiviral activity against human influenza virus.

(1) A sample to be measured for its antiviral activity is dissolved in dimethyl sulfoxide (DMSO) and then diluted with MEM*.
(2) 0.5 mL each of the diluted sample in (1) and a diluted viral culture fluid with the MEM are mixed and incubated at 37° C. for 2 hours.
(3) After the incubation in (2), the sample is inoculated at 37° C. for 1 hour in MDCK cells previously cultured for 24 hours in a 6-well cell culture plate.
(4) The sample is removed from each well, and the MEM medium containing 1% agarose is overlaid on the cells which are then cultured for 2 days.
(5) Further, an MEM-agarose containing 0.01% Neutral Red is overlaid on the cells which are then cultured for 4 hours or more.
(6) The antiviral activity is expressed in terms of a decrease in the number of plaques, relative to that on wells to which the sample was not added.

*MEM: minimum essential medium containing 0.001% DEAE dextran and 0.01% trypsin.

Figure 39:
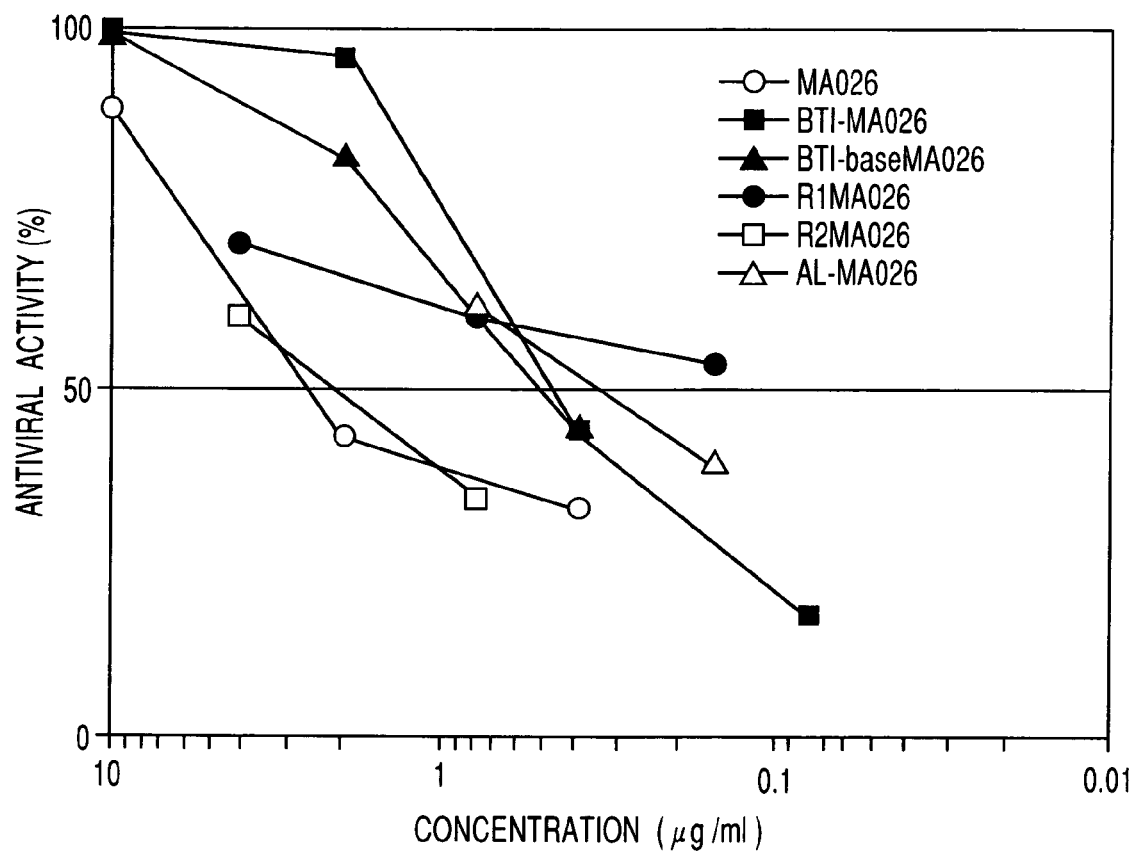
FIG. 39 is a graph showing the antiviral activity against avian influenza virus.

As a result of the test conducted according to the method described above, the results shown in FIG. 38 were obtained for the swine influenza virus, and the results in FIG. 39 were obtained for the avian influenza virus.

Example 11

<Antiviral Activity of the Present Peptides Against Herpes Virus Derived from Domestic Animals>

The evaluation of the antiviral activity against herpes virus derived from domestic animals was conducted in the manner described below, by partially modifying the method for the influenza virus set forth in Example 10. Note that the viral strain used in this test was domestic-animal hygiene strains supplied from the Japanese Association of Vetrinary Biologics. Viral strain VS1001 (Yamagata S-81) was used as the swine herpes virus (Aujeszkey's disease virus). The swine herpes virus is reported, for example, in Vox Sanguinis, 67 Suppl. 3, 191-196, 1994, as an alternative virus for evaluating antiviral activity against the human herpes virus.

(1) A sample to be measured for its antiviral activity is dissolved in dimethyl sulfoxide (DMSO) and then diluted with MEM medium.
(2) 0.5 mL each of the diluted sample in (1) and a viral culture fluid diluted with the MEM are mixed and incubated at 37° C. for 2 hours.
(3) After the incubation in (2), the sample is inoculated at 37° C. for 1 hour in MDCK cells previously cultured for 24 hours in a 6-well cell culture plate.
(4) The sample is removed from each well, and the MEM medium containing 1% agarose is overlaid on the cells which are then cultured for 2 days.
(5) Further, an MEM-agarose containing 0.01% Neutral Red is overlaid on the cells which are then cultured for 4 hours or more.
(6) The antiviral activity is expressed in terms of a decrease in the number of plaques, relative to that on wells to which the sample was not added.

As a result of the test conducted according to the method described above, the result shown in FIG. 40 was obtained for the swine herpes virus.

Example 12

<Antiviral Activity of the Present Peptides against Japanese Encephalitis Virus>

The evaluation of the antiviral activity against Japanese encephalitis virus derived from domestic animals was conducted by TCID50 method using 96-well plate in the manner described below. Note that the viral strain used in this test was domestic-animal hygiene strains supplied from the Japanese Association of Vetrinary Biologics. Viral strain VS0306 (Taniyama S-2) was used as the swine Japanese encephalitis virus.

(1) A sample to be measured for its antiviral activity is dissolved in dimethyl sulfoxide (DMSO) and then diluted with MEM medium.
(2) 0.5 mL each of the diluted sample in (1) and a viral culture fluid diluted with the MEM medium are mixed and incubated at 37° C. for 2 hours.
(3) 100 μL per well of each incubated sample of (2) is inoculated to BHK-21 cells, which have been previously incubated for 24 hours in 96-well cell culture plate. The present peptides were diluted in 5 fold of 6 steps (×5, ×25, ×125, ×625, ×3125 and×15625). The dilute samples were inoculated for each 4 wells.
(4) After incubation for 5 days or more, each well is observed to confirm the presence or absence of cell cytopathic effect.
(5) The viral titer was obtained by calculating the dilution ratio in a well showing 50% infection, and is expressed in terms of a decrease in the viral titer, relative to that on wells to which the sample was not added.

As a result of the test conducted according to the method described above, the result shown in FIG. 41 was obtained for the swine Japanese encephalitis virus.

Example 13

<Antiviral Activity of the Present Peptides Against Shrimp Virus>

The antiviral effect of the present peptides MA026 and BTI-MA026 against a shrimp virus (white spot syndrome virus) was examined.

*Penaeus monodon* (black tiger shrimp) weighing about 20 g were divided at random into groups each consisting of 10 shrimps and raised separately. A viral culture fluid prepared by diluting the white spot syndrome virus (WSSV $LD_{50}$ value; $10^{-3.6}$) 2000-fold with Hank's solution was mixed with an equal volume of a diluted solution (100 μg/mL) of the present peptides MA026 and BTI-MA026. After the mixture was incubated at 25° C. for 1 hour, the solution was intramuscularly injected at a dose of 0.1 mL into each shrimp, for viral inoculation. Whether the shrimps were actually inoculated with the virus or not was determined by observing them for 2 weeks after viral infection, and pathologically examining the ones that dies. The lesion tissues were examined to detect the viral gene by the PCR method. In the control group, Hank's solution only was used.

Figure 42:
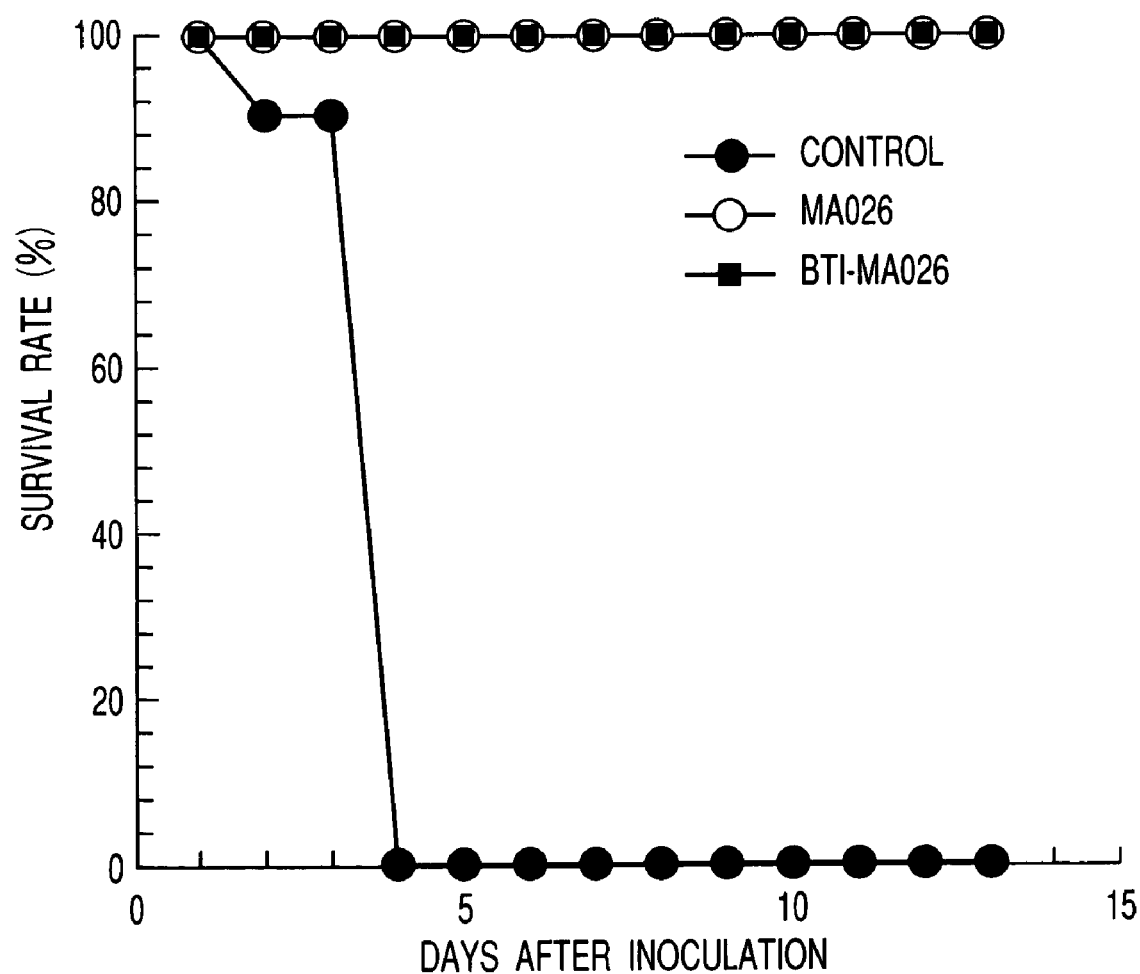
FIG. 42 is a graph showing the antiviral activity against shrimp virus.

The results are shown in FIG. 42. As is also apparent from FIG. 42, all shrimps in the control group died within 4 days after inoculation with the virus, while there was no dead shrimp in the groups treated with the present peptide MA026 and the present peptide BTI-MA026.

Example 14

<Antiviral Activity of the Present Peptides Against Hepatitis C Virus>

Using the present peptides MA026, BTI-MA026 and R2MA026 as objects, the antiviral effect against hepatitis C virus (HCV) was examined. The experiments were conducted according to the method of Mizutani et al. (Biochem. Biophys. Res. Commun. 227, 822-826, 1996) under supervision of Dr. Kunitada Shimotohno at Institute for Viral Research, Kyoto University.

(1) $1\times10^6$ gene titer per 0.1 mL of HCV was infected with $1\times10^6$ MT-2C cells per 1 mL, and cultured at 32° C. for 4 days.

(2) The infected cells of (1) were divided ($10^5$ cells per well) into a 96-well plate and incubated at 32° C. for 1 day.

(3) Each of the present peptides was added to each well so that the concentration thereof became 1 μM and 5 μM, and incubated at 32° C. for further 2 days.

(4) RNA was extracted from the test cells, and after synthesized cDNA with a reverse transcriptase, PCR of first and second round were performed to detect the HCV gene.

(5) The inhibition effect against HCV was evaluated by comparing fluorescence intensities of the PCR products originated from the HCV infected cells to which the test sample was added, assuming the fluorescence intensity of the PCR product originated from the infected cells to which no test substance was added, to be 100%.

These results are set forth in Table 14 below:

TABLE 14

| Sample | Concentration (μM) | Inhibition rate against HCV (%) |
|---|---|---|
| MA026 | 5 | 56 |
|  | 1 | 0 |
| BTI-MA02G | 5 | 59 |
|  | 1 | 23 |
| R2MA026 | 5 | 55 |
|  | 1 | 18 |

As is apparent from the results in Table 14, the present peptides MA026, BTI-MA026 and R2MA026 inhibited proliferation of hepatitis C virus.

As described above, the strain belonging to a novel species, and novel peptides of the present invention are useful as antiviral agents against viruses causing infections in mammals such as humans and domestic animals and against viruses causing infections in fishery resources such as fish and crustaceans.

Microorganisms, e.g., viruses and bacteria, are known to be factors causing various infections. Research and development of antibiotics, etc., against infections caused by bacteria are advancing, and many pharmaceutical preparations are in actual use. On the other hand, pharmaceutical preparations against infections caused by viruses are not as advanced as the antibacterial agents, under the present circumstances, although causative viruses themselves have been identified with the development in virology in recent years. Under these circumstances, the strain belonging to a novel species of the present invention and novel peptides of the present invention are expected to play an extremely important role in the pharmaceutical filed of organisms.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An isolated peptide or a salt thereof, wherein the peptide has the following formula (I):
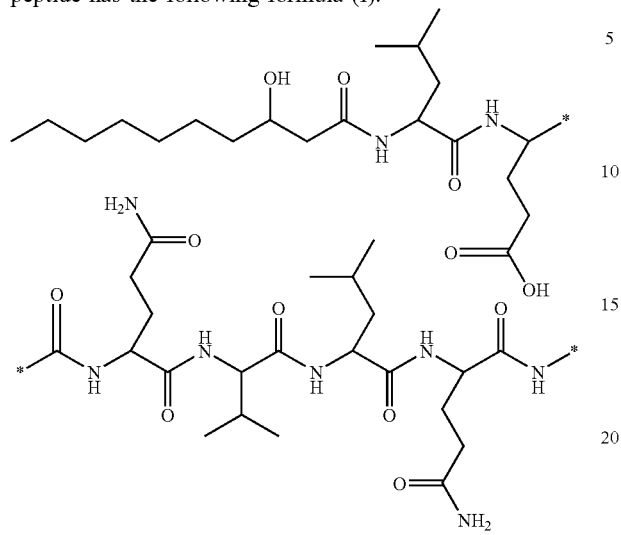
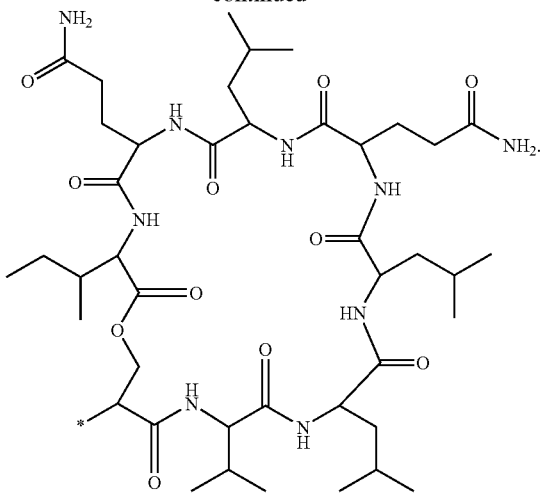
2. An isolated peptide or a salt thereof, wherein the peptide has the following formula (II):
(II)
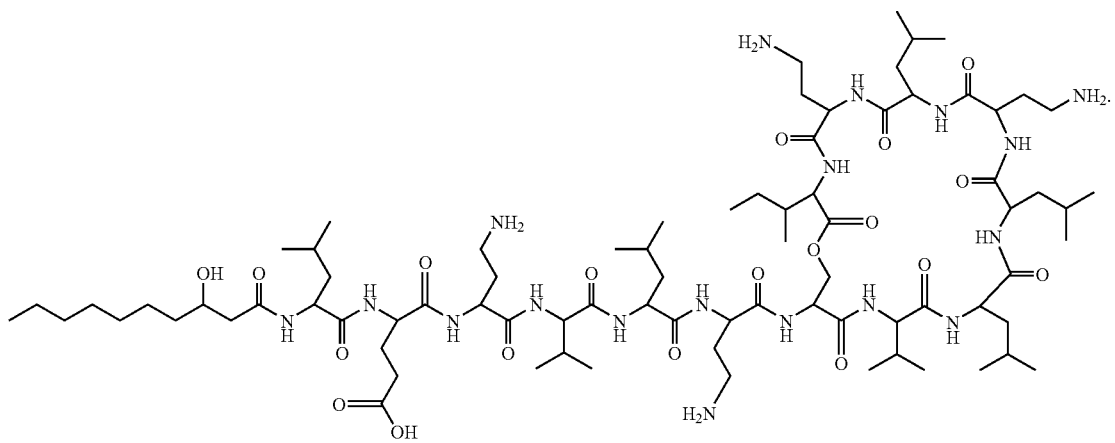
3. An isolated lower-alkylated derivative of a peptide or a salt thereof, wherein said derivative has the following formula (VI):
(VI)
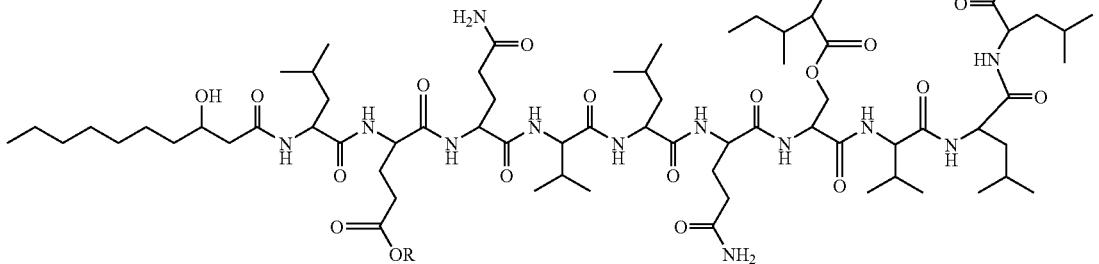
wherein R is a methyl group.

4. An isolated peptide or a salt thereof, wherein the peptide has the following formula (IV):

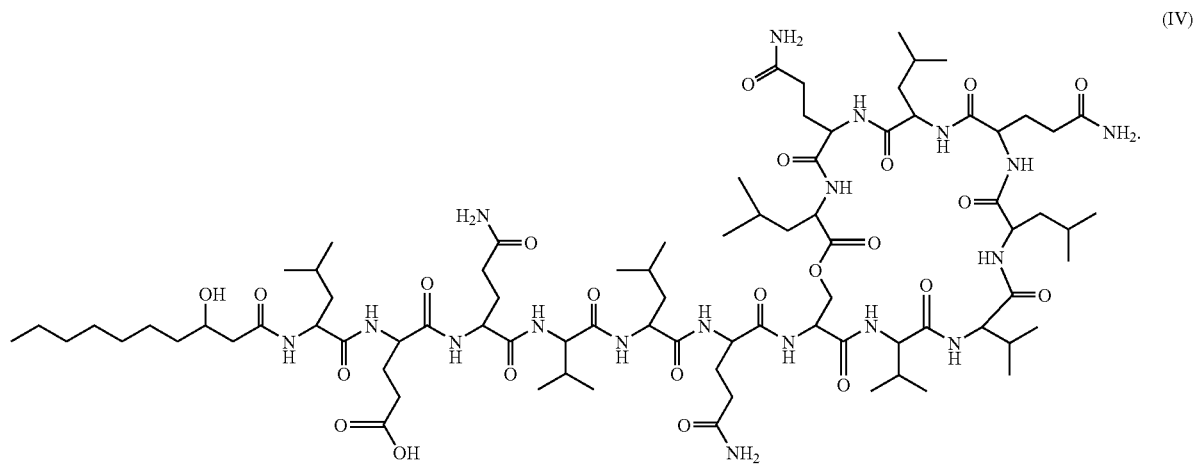

5. An isolated peptide or a salt thereof, wherein the peptide has the following formula (V):

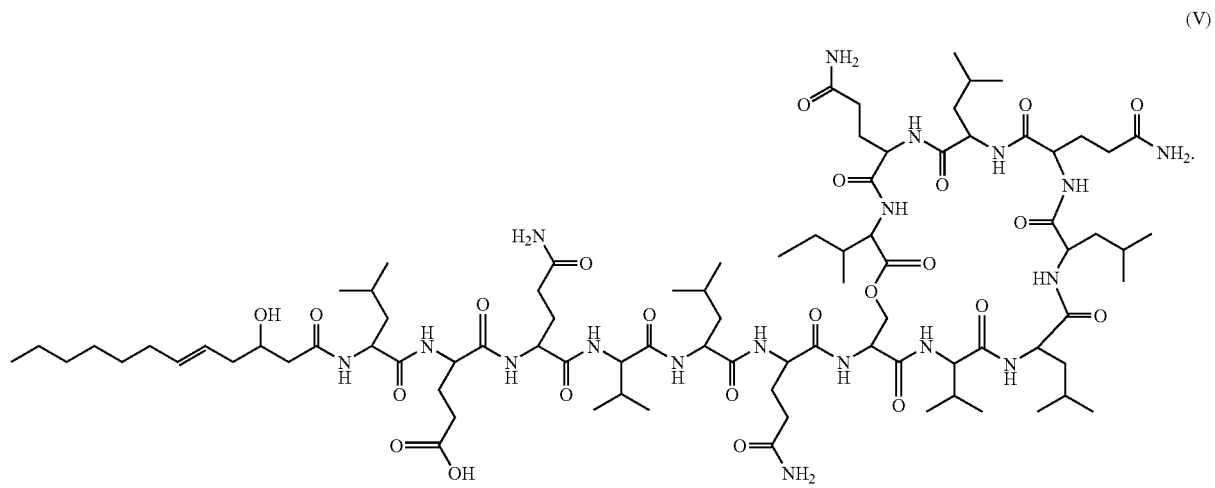

6. The peptide according to claim 1, wherein the peptide is isolated and purified from a culture of *Pseudomonas* sp. RtIB026 deposited under accession number FERM BP-7436.

7. A method of preparing the peptide according to claim 1, comprising:
culturing *Pseudomonas* sp. RtIB026 deposited under accession number FERM BP-7436,
obtaining a culture product of the microorganism; and
recovering the peptide according to claim 1 from the culture product.

8. An antiviral composition having antiviral activity against infectious hematopoietic necrosis virus (IHNV) in salmonid, rhabdovirus (EVA) in American eels, rhabdovirus (EVEX) in European eels, swine influenza virus, avian influenza virus, swine herpes virus, swine Japanese encephalitis virus, shrimp virus (white spot syndrome virus) and hepatitis C virus (HCV), the composition comprising a pharmaceutically effective amount of the peptide according to claim 1, in combination with a pharmaceutically acceptable carrier.

9. A method of treating a subject suffering from infection with a virus, comprising administering to the subject in need thereof a pharmaceutically effective amount of the peptide according to claim 1 as an effective ingredient, wherein the infection with a virus is an infection with at least one virus selected from the group consisting of infectious hematopoietic necrosis virus (IHNV) in salmonid, rhabdovirus (EVA) in American eels, rhabdovirus (EVEX) in European eels, swine influenza virus, avian influenza virus, swine herpes virus, swine Japanese encephalitis virus, shrimp virus (white spot syndrome virus) and hepatitis C virus (HCV).

10. The peptide according to claim 4, wherein the peptide is isolated and purified from a culture of *Pseudomonas* sp. RtIB026 deposited under accession number FERM BP-7436.

11. A method of preparing the peptide according to claim 4, comprising:
   culturing *Pseudomonas* sp. RtIB026 deposited under accession number FERM BP-7436,
   obtaining a culture product of the microorganism; and
   recovering the peptide according to claim 4 from the culture product.

12. An antiviral composition having antiviral activity against infectious hematopoietic necrosis virus (IHNV) in salmonid, rhabdovirus (EVA) in American eels; rhabdovirus (EVEX) in European eels, swine influenza virus, avian influenza virus, swine herpes virus, swine Japanese encephalitis virus, shrimp virus (white spot syndrome virus) and hepatitis C virus (HCV), the composition comprising a pharmaceutically effective amount of the peptide according to claim 4, in combination with a pharmaceutically acceptable carrier.

13. A method of treating a subject suffering from infection with a virus, comprising administering to the subject in need thereof a pharmaceutically effective amount of the peptide according to claim 4 as an effective ingredient, wherein the infection with a virus is an infection with at least one virus selected from the group consisting of infectious hematopoietic necrosis virus (IHNV) in salmonid, rhabdovirus (EVA) in American eels, rhabdovirus (EVEX) in European eels, swine influenza virus, avian influenza virus,swine herpes virus, swine Japanese encephalitis virus, shrimp virus (white spot syndrome virus) and hepatitis C virus (HCV).

14. The peptide according to claim 5, wherein the peptide is isolated and purified from a culture of *Pseudomonas* sp. RtIB026 deposited under accession number FERM BP-7436.

15. A method of preparing the peptide according to claim 5, comprising:
   culturing *Pseudomonas* sp. RtIB026 deposited under accession number FERM BP-7436,
   obtaining a culture product of the microorganism; and
   recovering the peptide according to claim 5 from the culture product.

16. An antiviral composition having antiviral activity against infectious hematopoietic necrosis virus (IHNV) in salmonid, rhabdovirus (EVA) in American eels, rhabdovirus (EVEX) in European eels, swine influenza virus, avian influenza virus, swine herpes virus, swine Japanese encephalitis virus, shrimp virus (white spot syndrome virus) and hepatitis C virus (HCV), the composition comprising a pharmaceutically effective amount of the peptide according to claim 5, in combination with a pharmaceutically acceptable carrier.

17. A method of treating a subject suffering from infection with a virus, comprising administering to the subject in need thereof a pharmaceutically effective amount of the peptide according to claim 5 as an effective ingredient, wherein the infection with a virus is an infection with at least one virus selected from the group consisting of infectious hematopoietic necrosis virus (IHNV) in salmonid, rhabdovirus (EVA) in American eels, rhabdovirus (EVEX) in European eels, swine influenza virus, avian influenza virus, swine herpes virus, swine Japanese encephalitis virus, shrimp virus (white spot syndrome virus) and hepatitis C virus (HCV).

18. An antiviral composition having antiviral activity against infectious hematopoietic necrosis virus (IHNV) in salmonid, rhabdovirus (EVA) in American eels, rhabdovirus (EVEX) in European eels, swine influenza virus, avian influenza virus, swine herpes virus, swine Japanese encephalitis virus, shrimp virus (white spot syndrome virus) and hepatitis C virus (HCV), the composition comprising a pharmaceutically effective amount of the peptide according to claim 2, in combination with a pharmaceutically acceptable carrier.

19. A method of treating a subject suffering from infection with a virus, comprising administering to the subject in need thereof a pharmaceutically effective amount of the peptide according to claim 2 as an effective ingredient, wherein the infection with a virus is an infection with at least one virus selected from the group consisting of infectious hematopoietic necrosis virus (IHNV) in salmonid, rhabdovirus (EVA) in American eels, rhabdovirus (EVEX) in European eels, swine influenza virus, avian influenza virus, swine herpes virus, swine Japanese encephalitis virus, shrimp virus (white spot syndrome virus) and hepatitis C virus (HCV).

20. An antiviral composition having antiviral activity against infectious hematopoietic necrosis virus (IHNV) in salmonid, rhabdovirus (EVA) in American eels, rhabdovirus (EVEX) in European eels, swine influenza virus, avian influenza virus, swine herpes virus, swine Japanese encephalitis virus, shrimp virus (white spot syndrome virus) and hepatitis C virus (HCV), the composition comprising a pharmaceutically effective amount of the peptide according to claim 3, in combination with a pharmaceutically acceptable carrier.

21. A method of treating a subject suffering from infection with a virus, comprising administering to the subject in need thereof a pharmaceutically effective amount of the peptide according to claim 3 as an effective ingredient, wherein the infection with a virus is an infection with at least one virus selected from the group consisting of infectious hematopoietic necrosis virus (IHNV) in salmonid, rhabdovirus (EVA) in American eels, rhabdovirus (EVEX) in European eels, swine influenza , avian influenza virus, swine herpes virus, swine Japanese encephalitis virus, shrimp virus (white spot syndrome virus) and hepatitis C virus (HCV).

* * * * *

SEQUENCE LISTING

<160> NUMBER OF SEQ ID NOS: 6

<210> SEQ ID NO 1
<211> LENGTH: 14
<212> TYPE: PRT
<213> ORGANISM: Pseudomonas sp.
<220> FEATURE:
<221> NAME/KEY: SITE

```
<222> LOCATION: (1)
<223> OTHER INFORMATION: a 3-hydroxy decanoyl group is bonded to the
      amino group of Leu (1)
<220> FEATURE:
<221> NAME/KEY: SITE
<222> LOCATION: (7) and (14)
<223> OTHER INFORMATION: The hydroxy group of Ser at (7) and the
      carboxylic group of Ile at (14) esterified to make a cyclic
      structure

<400> SEQUENCE: 1

Leu Gln Gln Val Leu Gln Ser Val Leu Leu Gln Leu Gln Ile
 1               5                  10

<210> SEQ ID NO 2
<211> LENGTH: 14
<212> TYPE: PRT
<213> ORGANISM: Pseudomonas sp.
<220> FEATURE:
<221> NAME/KEY: SITE
<222> LOCATION: (1)
<223> OTHER INFORMATION: a 3-hydroxy decanoyl group is bonded to the
      amino group of Leu (1)
<220> FEATURE:
<221> NAME/KEY: MUTAGEN
<222> LOCATION: (3), (6), (11), (13)
<223> OTHER INFORMATION: Each of the Gln's at (3), (6), (11), (13) is
      modified to Dbu, which is 2,4-diaminobutyric acid
<220> FEATURE:
<221> NAME/KEY: SITE
<222> LOCATION: (7) and (14)
<223> OTHER INFORMATION: The hydroxy group of Ser at (7) and the
      carboxylic group of Ile at (14) esterified to make a cyclic
      structure

<400> SEQUENCE: 2

Leu Gln Gln Val Leu Gln Ser Val Leu Leu Gln Leu Gln Ile
 1               5                  10

<210> SEQ ID NO 3
<211> LENGTH: 14
<212> TYPE: PRT
<213> ORGANISM: Pseudomonas sp.
<220> FEATURE:
<221> NAME/KEY: SITE
<222> LOCATION: (1)
<223> OTHER INFORMATION: a 3-hydroxy decanoyl group is bonded to the
      amino group of Leu (1)
<220> FEATURE:
<221> NAME/KEY: MUTAGEN
<222> LOCATION: (3), (6), (11), (13)
<223> OTHER INFORMATION: Each of the Gln's at (3), (6), (11), (13) is
      modified to Dbu, which is 2,4-diaminobutyric acid

<400> SEQUENCE: 3

Leu Gln Gln Val Leu Gln Ser Val Leu Leu Gln Leu Gln Ile
 1               5                  10

<210> SEQ ID NO 4
<211> LENGTH: 14
<212> TYPE: PRT
<213> ORGANISM: Pseudomonas sp.
<220> FEATURE:
<221> NAME/KEY: SITE
<222> LOCATION: (1)
<223> OTHER INFORMATION: a 3-hydroxy decanoyl group is bonded to the
      amino group of Leu (1)
<220> FEATURE:
<221> NAME/KEY: SITE
<222> LOCATION: (7) and (14)
<223> OTHER INFORMATION: The hydroxy group of Ser at (7) and the
      carboxylic group of Leu at (14) esterified to make a cyclic
      structure
```

```
<400> SEQUENCE: 4

Leu Glu Gln Val Leu Gln Ser Val Val Leu Gln Leu Gln Leu
 1               5                  10

<210> SEQ ID NO 5
<211> LENGTH: 14
<212> TYPE: PRT
<213> ORGANISM: Pseudomonas sp.
<220> FEATURE:
<221> NAME/KEY: SITE
<222> LOCATION: (1)
<223> OTHER INFORMATION: a 3-hydroxydodec-5-enoyl group is bonded to the
      amino group of Leu (1)
<220> FEATURE:
<221> NAME/KEY: SITE
<222> LOCATION: (7) and (14)
<223> OTHER INFORMATION: The hydroxy group of Ser at (7) and the
      carboxylic group of Ile at (14) esterified to make a cyclic
      structure

<400> SEQUENCE: 5

Leu Glu Gln Val Leu Gln Ser Val Leu Leu Gln Leu Gln Ile
 1               5                  10

<210> SEQ ID NO 6
<211> LENGTH: 14
<212> TYPE: PRT
<213> ORGANISM: Pseudomonas sp.
<220> FEATURE:
<221> NAME/KEY: SITE
<222> LOCATION: (1)
<223> OTHER INFORMATION: 3-hydroxy decanoyl group is bonded to the
      amino group of Leu (1)
<220> FEATURE:
<221> NAME/KEY: MUTAGEN
<222> LOCATION: (2)
<223> OTHER INFORMATION: Glu at (2) is alkylated
<220> FEATURE:
<221> NAME/KEY: SITE
<222> LOCATION: (7) and (14)
<223> OTHER INFORMATION: The hydroxy group of Ser at (7) and the
      carboxylic group of Ile at (14) esterified to make a cyclic
      structure

<400> SEQUENCE: 6

Leu Glu Gln Val Leu Gln Ser Val Leu Leu Gln Leu Gln Ile
 1               5                  10
```